US012697340B2

(12) United States Patent
Lopez et al.

(10) Patent No.: US 12,697,340 B2
(45) Date of Patent: *Aug. 4, 2026

(54) COMPOSITIONS AND METHODS FOR CELLULAR AGEING, STRESS RESILIENCE, AUTOPHAGY, INFLAMMATION AND LONGEVITY

(71) Applicant: JUVN3 Holdings, LLC, Millstone, NJ (US)

(72) Inventors: Hector L. Lopez, Cream Ridge, NJ (US); Tim Ziegenfuss, Carlsbad, CA (US); Matthew Titlow, Carlsbad, CA (US)

(73) Assignee: JUVN3 HOLDINGS, LLC, Millstone, NJ (US)

( * ) Notice: Subject to any disclaimer, the term of this patent is extended or adjusted under 35 U.S.C. 154(b) by 755 days.

This patent is subject to a terminal disclaimer.

(21) Appl. No.: 17/518,184

(22) Filed: Nov. 3, 2021

(65) Prior Publication Data

US 2023/0149412 A1 May 18, 2023

Related U.S. Application Data

(63) Continuation-in-part of application No. 16/718,023, filed on Dec. 17, 2019.

(60) Provisional application No. 62/849,758, filed on May 17, 2019, provisional application No. 62/769,979, filed on Nov. 20, 2018.

(51) Int. Cl.
| | |
|---|---|
| *A61K 31/522* | (2006.01) |
| *A61K 31/05* | (2006.01) |
| *A61K 31/19* | (2006.01) |
| *A61K 31/198* | (2006.01) |
| *A61K 31/22* | (2006.01) |
| *A61K 31/225* | (2006.01) |
| *A61K 31/26* | (2006.01) |
| *A61K 31/352* | (2006.01) |
| *A61K 31/353* | (2006.01) |
| *A61K 31/375* | (2006.01) |
| *A61K 31/455* | (2006.01) |
| *A61K 31/555* | (2006.01) |
| *A61K 31/7048* | (2006.01) |
| *A61K 33/04* | (2006.01) |
| *A61K 36/63* | (2006.01) |
| *A61K 36/74* | (2006.01) |
| *A61K 36/82* | (2006.01) |
| *A61K 36/87* | (2006.01) |
| *A61K 45/06* | (2006.01) |
| *A61P 39/06* | (2006.01) |

(52) U.S. Cl.
CPC ............ *A61K 31/522* (2013.01); *A61K 31/05* (2013.01); *A61K 31/19* (2013.01); *A61K 31/198* (2013.01); *A61K 31/22* (2013.01); *A61K 31/225* (2013.01); *A61K 31/26* (2013.01); *A61K 31/352* (2013.01); *A61K 31/353* (2013.01); *A61K 31/375* (2013.01); *A61K 31/455* (2013.01); *A61K 31/555* (2013.01); *A61K 31/7048* (2013.01); *A61K 33/04* (2013.01); *A61K 36/63* (2013.01); *A61K 36/742* (2024.05); *A61K 36/82* (2013.01); *A61K 36/87* (2013.01); *A61K 45/06* (2013.01); *A61P 39/06* (2018.01)

(58) Field of Classification Search
None
See application file for complete search history.

(56) References Cited

U.S. PATENT DOCUMENTS

| | | | |
|---|---|---|---|
| 6,440,436 B1 | 8/2002 | Ghosal | |
| 8,642,651 B2 | 2/2014 | Miljkovic et al. | |
| 8,759,304 B2 | 6/2014 | Harley et al. | |
| 9,327,005 B1 | 5/2016 | Pietrzkowski | |
| 2007/0037827 A1* | 2/2007 | Nunes ................. | C07D 471/04 |
| | | | 544/362 |
| 2009/0175927 A1 | 7/2009 | Gammelsaeter et al. | |
| 2009/0214607 A1 | 8/2009 | Lintner et al. | |

(Continued)

FOREIGN PATENT DOCUMENTS

| | | |
|---|---|---|
| EP | 3068240 A1 | 9/2016 |
| EP | 2731599 B1 | 10/2018 |

(Continued)

OTHER PUBLICATIONS

"NAD3TR 30 . An All Natural NAD+ BoosterTM" (a product advertisement webpage obtained from the website: https://hpnsupplements.com/products/nad3-30?srsltid=AfmBOoqvhKwGW14VG-EJx3lqQwdRh2t1b80Fj8ofU_-caRZ90417XBge). (Year: 2018).*

(Continued)

*Primary Examiner* — Sin J Lee
(74) *Attorney, Agent, or Firm* — Umberg Zipser LLP

(57) ABSTRACT

Compositions and methods are presented that that help reduce cellular ageing, improve cellular stress resilience, and/or promote increased longevity. Especially preferred compositions include a combination of a purine alkaloid, an isothiocyanate or thioglucoside, and a metal-containing antioxidant, where the purine alkaloid, the isothiocyanate or thioglucoside, and the metal-containing antioxidant may be chemically isolated compounds or extracts or other preparations from naturally occurring entities such as plants, bacteria, yeast, etc. Advantageously, contemplated compositions will be effective to reduce and repair oxidative stress, improve mitochondrial function, augment DNA repair and telomere maintenance, increase fatty acid metabolism, and modulate histone deacetylation.

6 Claims, 48 Drawing Sheets

(56) References Cited

U.S. PATENT DOCUMENTS

| | | | |
|---|---|---|---|
| 2010/0062435 A1 | 3/2010 | Claudio et al. | |
| 2011/0274773 A1 | 11/2011 | Ibraheim | |
| 2013/0303594 A1* | 11/2013 | Kappei | C07K 14/4703 |
| | | | 435/7.1 |
| 2015/0132280 A1 | 5/2015 | Lopez et al. | |
| 2015/0313950 A1* | 11/2015 | Gammelsaeter | A61Q 19/02 |
| | | | 424/523 |
| 2016/0066603 A1 | 3/2016 | Adam et al. | |
| 2017/0274370 A1 | 9/2017 | Barker et al. | |
| 2017/0296501 A1 | 10/2017 | Lowery et al. | |
| 2018/0104248 A1 | 4/2018 | Lopez et al. | |
| 2020/0384043 A1 | 12/2020 | Titlow | |
| 2023/0302033 A1* | 9/2023 | Rentko | A61K 45/06 |

FOREIGN PATENT DOCUMENTS

| | | | |
|---|---|---|---|
| JP | 2009155333 A | 7/2009 | |
| WO | WO-2020131058 A1 * | 6/2020 | A61K 36/577 |
| WO | WO-2023220567 A1 * | 11/2023 | A23P 10/00 |
| WO | WO-2025014519 A1 * | 1/2025 | A61P 43/00 |

OTHER PUBLICATIONS

Images from "NAD3TR 30 . An All Natural NAD+ BoosterTM" (a product advertisement webpage obtained from: https://hpnsupplements. com/products/nad3-30?srsltid=AfmBOoqvhKwGW14VG-EJx3lqQwdRh2t1b80Fj8ofU_-caRZ904I7XBge). (Year: 2018).*

Clement et al ("The Plasma NAD+ Metabolome Is Dysregulated in "Normal" Aging", Rejuvenation Research, vol. 22 (2) (Apr. 2019), p. 121-130) (Year: 2019).*

Holman ("Inherency in the Patenting of Biotechnology and Pharmaceutical Innovation", 39 Biotechnology Law Report 79, No. 2, 2020, p. 79-99) (Year: 2020).*

Pappas ("Under High Pressure: New Mechanism of Action Can't Save Drug Administration Claims", IP Update, Jun. 22, 2023, an internet article obtained from the website: https://www.ipupdate. com/2023/06/under-high-pressure-new-mechanism-of-action-cant-save-drug-administration-claims/) (Year: 2023).*

Chronic Fatigue Syndrome, Johns Hopkins Medicine, https://www. hopkinsmedicine.org/health/conditions-and-diseases/chronic fatigue syndrome, downloaded Jun. 18, 2022, 4 pages.

Fahy et al., "Reversal of epigenetic aging and immunosenescent trends in humans," Aging Cell. 2019, 12 pages.

Feduccia et al., "Locomotor activation by theacrine, a purine alkaloid structurally similar to caffeine: Involvement of adenosine and dopamine receptors," Pharmacology, Biochemistry and Behavior 102 (2012) 241-248, 8 pages.

Ge et al., "Theacrine protects against nonalcoholic fatty liver disease by regulating acylcarnitine metabolism," Metabolism Aug. 2018;85:227-239, 13 pages.

Li et al., "Antioxidative activities and the chemical constituents of two Chinese teas, Camellia kucha and C. ptilophylla," International Journal of Food Science & Technology 2012, 47, 1063-1071, 9 pages.

Li et al., "Differing chemical compositions of three teas may explain their different effects on acute blood pressure in spontaneously hypertensive rats," J Sci Food Agric (2014), 7 pages.

Li et al., "Theacrine, a Purine Alkaloid Obtained From Camellia assamica var. kucha, Attenuates Restraint Stress-Provoked Liver Damage in Mice," Journal of Agricultural and Food Chemistry 2013, 61, 6328-6335, 8 pages.

López-Otín et al., "The Hallmarks of Aging," Cell 153, Jun. 6, 2013 © Elsevier Inc., 24 pages.

Messerschmidt et al., "DNA methylation dynamics during epigenetic reprogramming in the germ line and breimplantation embryos," Genes & Development, 28:812-828, ISSN 0890-9369/14; www. genesdev.org, 17 pages.

PCT International Search Report and Written Opinion, International Application No. PCT/US2021/12265; International Filing Date Jan. 6, 2021, 11 pages.

Puritan's Pride, "High Performance Nutrition NAD3-NAD+ Booster" (a product information sheet (Feb. 12, 2015) obtained from the website: https://www.puritan.com/energy-244/ppniagen-nadbooster250mg6-059349) (Year: 2015), 1 page.

Sarria et al., "Copper (II) and zinc (II) complexes with flavanone derivatives: Identification of potential cholinesterase Inhibitors by on-flow assays," Journal of Inorganic Biochemistry 164 (2016) 141-149, 9 pages.

Schafer et al., "The senescence-associated secretome as an indicator of age and medical risk," JCI Insight, 2020;5(12):e133668. https:// doi.org/10.1172/jci.insight.133668, 13 pages.

Schmidt et al., "The roles of the reprogramming factors Oct4, Sox2 and Klf4 in resetting the somatic cell epigenome during induced pluripotent stem cell generation," Genome Biology 2012, 13:251, 11 pages.

Wagner W., "The Link Between Epigenetic Clocks for Aging and Senescence," Frontiers in Genetics, Apr. 3, 2019, vol. 10, Article 303, 6 pages.

Wang et al, "Theacrine, a purine alkaloid with anti-inflammatory and analgesic activities," Fitoterapia 81 (2010) 627-631, 5 pages.

Wikipedia webpage Niacin, https://en.Wikipedia.org/wiki/Niacin; downloaded Oct. 22, 2021, 24 pages.

Wikipedia webpage Wasabi, https://en.Wikipedia.org/wiki/Wasabi; downloaded Oct. 22, 2021, 11 pages.

World of Wasabi, Wasabi in a pill (100% Pure Wasabia Japonica capsules) https://wasabi.org/articles/medical-uses-of-wasabia-japonica/wasabi-in-a-pill/ downloaded Jun. 18, 2022, 3 pages.

Ray et al., "Quality of attention in chronic fatigue syndrome; subjective reports of everyday attention and cognitive difficulty, and performance on tasks of focused attention," Abstract, Br J. Clin. Psychol., Sep. 1993, vol. 32(3), p. 357-364, 1993.

Nogueiras et al., "Sirtuin 1 And Sirtuin 3: Physiological Modulators of Metabolism," Physiol Rev., Jul. 2012; 92(3):1479-1514.

Wu et al., "The effect of selenium, as selenomethionine, on genome stability and cytotoxicity in human lymphocytes measured using the cytokinesis-block micronucleus cytome assay," Mutagenesis, 2009; 24(3):225-232.

Breitzig et al., "4-Hydroxy-2-nonenal: a critical target in oxidative stress?" Am. J. Physiol. Cell Physiol., 2016; 311: C537-C543.

Chen et al., "The Roles of Autophagy and the Inflammasome during Environmental Stress-Triggered Skin Inflammation," Int. J. Mol. Sci., 2016; 17(2063); 16 pgs.

Fernandez-Marcos et al., "Regulation of PGC-1alpha, a nodal regulator of mitochondrial biogenesis," Am J Clin Nutr, 2011;93(suppl):884S-90S.

Garcia-Peterson et al., "Sirtuins in Skin and Skin Cancers," Skin Pharmacol. Physiol., 2017; 30(4):216-224.

Glueck et al., "Tributyrin Supplementation Protects Immune Responses and Vasculature and Reduces Oxidative Stress in the Proximal Colon of Mice Exposed to Chronic-Binge Ethanol Feeding," Journal of Immunology Research, 2018; vol. 2018; 13 pgs.

Haga et al., "Complete chloroplast genome sequence and phylogenetic analysis of wasabi (Eutrema japonicum) and its relatives," Scientific Reports, 2019; 9:14377; 10 pgs.

High Performance Nutrition, NAD+ Booster Information Sheet dated Dec. 19, 2018, 1 page. Retrieved from: https://hpnsupplements. com/products/nad3-60?adgroupid=63168293231&adid=303132706473 &campaignid=1598270119&gclid=EAlaIQobChMI5fDev9X-7gIVk8DACh0wAAN3EAQYAIABEgKxCvD_BwE.

International Search Report and Written Opinion for International Application No. PCT/US21/12265 dated Mar. 25, 2021; 11 pgs.

Milaeva, Elena R., "Metal-Based Antioxidants—Potential Therapeutic Candidates for Prevention the Oxidative Stress—Related Carcinogenesis: Mini-Review," Current Topics in Medicinal Chemistry, 2011; 11:2703-2713.

Mizushima et al., "How to Interpret LC3 Immunoblotting," Autophagy, 2007; 3(6):542-545.

Ruan et al., "Targeting NAD+ degradation: The therapeutic potential of flavonoids for Alzheimer's disease and cognitive frailty," Pharmacological Research, 2018; 128:345-358.

(56) References Cited

OTHER PUBLICATIONS

Sharma et al., "Chapter 40: Histone H2AX Phosphorylation: A
Marker for DNA Damage," DNA Repair Protocols, Methods in
Molecular Biology, 2012 New York, vol. 920, pp. 613-626.

* cited by examiner

# = indicates less than CTL unperturbed cells

\# = indicates less than CTL unperturbed cells

# = indicates less than CTL cells;
* = indicates greater than CTL cells.

6-h treatments, unpreturbed cells (no H2O2)

PBMC Telomere length

FIG. 13A          FIG. 13B          FIG. 13C qPCR-determined Telomere length (outliers removed)
methods from Lin et al. (Psychoneuroendocrinology 99: 271-278, 2019)

, greater than CTL at week 4 (p<0.05)

[1], trended greater than CTL at week 4 (p=0.055)

PBMC NADH concentrations

PBMC NADPH concentrations

COMPOSITIONS AND METHODS FOR CELLULAR AGEING, STRESS RESILIENCE, AUTOPHAGY, INFLAMMATION AND LONGEVITY

This application is a continuation-in-part of and claims priority to co-pending U.S. Non-provisional application Ser. No. 16/718,023, filed on Dec. 17, 2019, which claims priority to U.S. Provisional Application No. 62/769,979, filed on Nov. 20, 2018, and U.S. Provisional Application No. 62/849,758, filed on May 17, 2019, the entire contents of which are herein incorporated by reference in their entirety.

FIELD OF THE INVENTION

The present disclosure relates to compositions and methods of use of various nutraceutical compositions, particularly as they relate to methods of reducing cellular ageing, improving cellular stress resilience, autophagy/mitophagy, functional restoration, cellular regenerative potential, regulating inflammation and/or longevity.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Numerous compositions and methods are known in the art to modulate one or more metabolic parameters in mammals (e.g., insulin or metformin to modulate glucose), however, most commonly such compositions are pharmaceutical agents that often have adverse effects. Moreover, most pharmaceutical compounds are target-specific to a particular receptor or enzyme and as such, provide only isolated effects to a system. Distal effects on other metabolic parameters or pathways are typically unintentional.

In a nutraceutical approach, various compounds are known with pleiotropic effect that can be given in isolation or together with a pharmaceutical or second nutraceutical to increase (in some cases synergistically) a desired effect on a pathway or signaling cascade. For example, quercetin alone, or leucine with low-dose metformin can be administered to stimulate sirtuin pathway output as described in EP 2731599. In another known approach as described in US 2018/0104248, synergistic combinations of theacrine and caffeine or wasabi extract are used to modulate mood, energy, focus, sexual desire, anxiety, or fatigue. While such combination is desirable in at least some instances, such combinations were only effective on a subjective level and were not shown to have substantial impact on one or more aspects of cellular ageing, cellular stress resilience, and/or longevity.

To address at least some aspects of ageing, various telomerase activating compounds were tested and some of them even used in a nutritional supplement as taught in U.S.

Pat. No. 8,759,304. Here, selected compounds related to astragalosides and ginsenosides were used to increase telomerase. However, no further pleiotropic effects were reported. On the other hand, increased oxygen consumption rate, extracellular acidification rate, and ATP production was reported in vivo by administering a cold-water extract of humic shale and/or an extract of the apple fruit or skin of the apple fruit as taught in U.S. Pat. No. 9,327,005. Once more, however, while desirable, the biological effects were confined to a relatively narrow effect.

Thus, even though various nutraceuticals are known in the art that provide one or more beneficial effects to cells and organisms, all or almost all of them suffer from various disadvantages. Consequently, there is a need to provide improved compositions and methods that have a wide spectrum of pleiotropic activity, and especially to reduce cellular ageing, improve cellular stress resilience, autophagy/mitophagy, functional restoration, cellular regeneration, regulating inflammation and/or increase longevity.

SUMMARY OF THE INVENTION

Various compositions and methods that presented that help reduce cellular ageing, improve cellular stress resilience, autophagy/mitophagy, functional restoration, cellular regeneration, regulating inflammation and/or provide increased longevity. Advantageously, such compositions are nutraceutical compositions that comprise pharmaceutically or nutraceutically acceptable ingredients that can be formulated into a variety of formats for oral administration as well as topical administration.

In one aspect of the inventive subject matter, the inventors contemplate a method of reducing primary hyperlipidemia in a mammal. The method includes administering a cytoprotective composition to the mammal in an amount effective to reduce primary hyperlipidemia in a mammal. The cytoprotective composition includes a cytoprotective formulation including a combination of (a) a purine alkaloid, (b) an isothiocyanate or thioglucoside, and (c) a metal-containing antioxidant. The cytoprotective formulation is formulated for oral administration with a nutritionally or pharmaceutically acceptable carrier.

In exemplary embodiments, the purine alkaloid is theacrine, the isothiocyanate or thioglucoside is isothiocyanate, and the metal-containing antioxidant is a copper-(I)-nicotinate complex. The inventors surprisingly discovered that the cytoprotective composition provides a significant decrease in total cholesterol, VLDL cholesterol, LDL cholesterol, and LDL:HDL to the mammal after 4 weeks, 8 weeks, and 12 weeks.

In another aspect of the inventive subject matter, the inventors contemplate a method of increasing telomere length in a cell of a mammal. The method includes administering a cytoprotective composition to the mammal in an amount effective to increase telomere length in a cell of a mammal. The cytoprotective composition includes a cytoprotective formulation including a combination of (a) a purine alkaloid, (b) an isothiocyanate or thioglucoside, (c) a metal-containing antioxidant, and optionally (d) one or more additional ingredients including selenium, a polyphenol, olive leaf extract, tributyrin, and/or BHB. The cytoprotective formulation is formulated for oral administration with a nutritionally or pharmaceutically acceptable carrier.

In exemplary embodiments, the purine alkaloid is theacrine, the isothiocyanate or thioglucoside is isothiocyanate, the metal-containing antioxidant is a copper-(I)-nicotinate complex, and the optional one or more additional ingredients optionally includes tributyrin. The inventors surprising discovered that that the cytoprotective composition provides an increase in telomere length in the cells of the mammal after 4 weeks.

In yet another aspect of the inventive subject matter, the inventors contemplate a method of increasing the expression of the sirtuin gene in a mammal. The method includes administering a cytoprotective composition to the mammal in an amount effective to increase the expression of the sirtuin gene in a mammal. The cytoprotective composition includes a cytoprotective formulation including a combination of (a) a purine alkaloid, (b) an isothiocyanate or thioglucoside, (c) a metal-containing antioxidant, and (d) one or more additional ingredients including selenium, a polyphenol, olive leaf extract, tributyrin, and/or BHB. The cytoprotective formulation is formulated for oral administration with a nutritionally or pharmaceutically acceptable carrier.

In exemplary embodiments, the purine alkaloid is theacrine, the isothiocyanate or thioglucoside is isothiocyanate, the metal-containing antioxidant is a copper-(I)-nicotinate complex, and the one or more additional ingredients includes tributyrin. The inventors surprising discovered that that the cytoprotective composition provides an upregulation of a sirtuin gene (e.g., at least one of sirtuin 1-7) of the mammal after 4 weeks, 8 weeks, and 12 weeks.

In yet another aspect of the inventive subject matter, the inventors contemplate a method of increasing at least one of the level of NAD+ or the ratio of NAD+/NADH, in a mammal. The method includes administering a cytoprotective composition to the mammal in an amount effective to increase at least one of the level of NAD+ or the ratio of NAD+/NADH, in a mammal. The cytoprotective composition includes a cytoprotective formulation including a combination of (a) a purine alkaloid, (b) an isothiocyanate or thioglucoside, (c) a metal-containing antioxidant, and optionally (d) one or more additional ingredients including selenium, a polyphenol, olive leaf extract, tributyrin, and/or BHB. The cytoprotective formulation is formulated for oral administration with a nutritionally or pharmaceutically acceptable carrier.

In exemplary embodiments, the purine alkaloid is theacrine, the isothiocyanate or thioglucoside is isothiocyanate, the metal-containing antioxidant is a copper-(I)-nicotinate complex, and the optional one or more additional ingredients includes tributyrin. The inventors surprising discovered that that the cytoprotective composition provides an increase in the level of NAD+ and the ratio of NAD+/NADH in the mammal after 12 weeks.

In another aspect of the inventive subject matter, the inventors contemplate a composition for reducing cellular ageing, improving cellular stress resilience, optimizing cellular autophagy/mitophagy, regulating inflammation, and/or increasing longevity that comprises a cytoprotective formulation that includes a combination of (a) a purine alkaloid, (b) an isothiocyanate or thioglucoside, and (c) a metal-containing antioxidant. Most typically, the cytoprotective formulation is formulated for oral administration with a nutritionally or pharmaceutically acceptable carrier.

Therefore, and viewed form a different perspective, the inventors also contemplate a method of reducing cellular ageing and inflammation, improving cellular stress resilience, autophagy/mitophagy and/or increasing longevity in a mammal that includes a step of administering a cytoprotective composition to the mammal in an amount effective to reduce cellular ageing, improve cellular stress resilience, and/or increase longevity in a mammal. Preferably, the cytoprotective composition includes a cytoprotective formulation comprising a combination of (a) a purine alkaloid, (b) an isothiocyanate or thioglucoside, and (c) a metal-containing antioxidant. It is further preferred in such methods that the cytoprotective formulation is formulated for oral administration with a nutritionally or pharmaceutically acceptable carrier.

In another aspect of the inventive subject matter, the inventors contemplate a method of supporting mitochondrial function in a mammal that includes a step of administering a cytoprotective composition to the mammal in an amount effective to support mitochondrial function, wherein the cytoprotective composition includes a cytoprotective formulation comprising a combination of (a) a purine alkaloid, (b) an isothiocyanate or thioglucoside, and (c) a metal-containing antioxidant.

In a further aspect of the inventive subject matter, the inventors contemplate a method of reducing oxidative stress in a cell of a mammal that includes a step of administering a cytoprotective composition to the mammal in an amount effective to reduce oxidative stress, wherein the cytoprotective composition includes a cytoprotective formulation comprising a combination of (a) a purine alkaloid, (b) an isothiocyanate or thioglucoside, and (c) a metal-containing antioxidant.

In yet another aspect of the inventive subject matter, the inventors also contemplate a method of reducing inflammation in a mammal that includes a step of administering a cytoprotective composition to the mammal in an amount effective to reduce inflammation, wherein the cytoprotective composition includes a cytoprotective formulation comprising a combination of (a) a purine alkaloid, (b) an isothiocyanate or thioglucoside, and (c) a metal-containing antioxidant.

Thus, the inventors also contemplate a method of stimulating metabolism in a mammal that has a step of administering a cytoprotective composition to the mammal in an amount effective to stimulate metabolism. Preferably, the cytoprotective composition includes a cytoprotective formulation comprises a combination of (a) a purine alkaloid, (b) an isothiocyanate or thioglucoside, and (c) a metal-containing antioxidant.

For example, in some embodiments, the purine alkaloid is present in and provided as a Camilla sp., *Theobroma* sp. or *Coffea* sp. extract, the isothiocyanate or thioglucoside is present in and provided as a *Brassica* sp. extract, and/or the metal-containing antioxidant comprises copper or zinc as a ligand to an organic moiety. In other embodiments, the purine alkaloid is theacrine, methylliberine, liberine, theobromine, theophylline, or caffeine, the isothiocyanate or thioglucoside is allyl isothiocyanate or 2-phenylethyl isothiocyanate, and/or the metal-containing antioxidant is a copper-(I)-nicotinate complex (or a nutritionally acceptable copper-II-complex or chelate, and less preferably cuprous oxide). In still further embodiments, the purine alkaloid is present in and provided as a Camilla sp., *Theobroma* sp. or *Coffea* sp. extract, the isothiocyanate or thioglucoside is present in and provided as a *Brassica* sp. extract, and the metal-containing antioxidant comprises copper or zinc as a ligand to an organic moiety. In still other embodiments, the purine alkaloid is theacrine, methylliberine, liberine, theobromine, theophylline, or caffeine, the isothiocyanate or thioglucoside is allyl isothiocyanate or 2-phenylethyl isothiocyanate, and the metal-containing is a copper-(I)-nicotinate complex (or a nutritionally acceptable copper-II-complex or chelate). In further preferred embodiments, the purine alkaloid is theacrine (TeaCrine®), the isothiocyanate or thioglucoside is present in and provided as an extract from *Eutrema japonicum*, and the metal-containing is a copper-(I)-nicotinate complex. Additionally, contemplated compositions may further include fulvate or fulvic acid (and its derivatives), and/or *Aronia* (e.g., as a powder, expressed juice, or extract).

As will be appreciated, all ingredients can be synthetic, nature-identical, or of natural origin in crude, partially processed, refined, or purified form. For example, purine alkaloids may be synthesized from a precursor, or isolated from a plant part such as a tea leaf, coffee bean and/or coffee fruit. Likewise, the isothiocyanate or thioglucoside may be fully synthetic, or isolated from various plant materials. Moreover, it should be noted that all ingredients may be disposed in a nutritionally acceptable matrix (e.g., within original plant material, fermented material that may or may not include a microorganism) or otherwise suitable carrier. Therefore, contemplated ingredients may be or be derived from natural materials and extracts, recombinant DNA technology, microbial fermentation, total organic synthesis, and any reasonable combination thereof. Of course, it should be appreciated that contemplated compositions may further comprise additional nutritional ingredients, including one or more exogenous gut-supporting and/or ketogenic amplifying compounds (e.g., acetoacetate, beta-hydroxybutyrate, octanoic acid, decanoic acid, tributyrin, butyrate, acetate), SIRT enhancing agents (e.g., butyrate, medium- and short-chain fatty acids, fisetin, resveratrol, quercetin, various catechins, curcumin, tyrosol, berberine, ferulic acid), the non-metal (metalloid) selenium, NAD enhancing agents (e.g., niacinamide, nicotinamide mononucleotide (NMN), or niacin), one or more phytocannabinoids (e.g., cannabidiol (CBD), cannibigerol, cannabidiolic acid, tetrahydrocannabinol acid), gingerol, shoagol, and/or triterpenes, diterpenes and sesquiterpenes, as well as tea extracts, and especially green or black tea extracts (which may or may not be standardized to have a specific threaflavin and/or thearubigin content).

Notably, the inventive subject matter includes a composition (e.g., a cytoprotective composition) for reducing cellular ageing, improving cellular stress resilience, and/or increasing longevity, wherein the composition includes a cytoprotective formulation including a combination of (a) a purine alkaloid, (b) an isothiocyanate or thioglucoside, and (c) a metal-containing antioxidant; and wherein the cytoprotective formulation is formulated for oral administration with a nutritionally or pharmaceutically acceptable carrier. As disclosed, the purine alkaloid may be present in and provided as a Camilla sp., *Theobroma* sp., or *Coffea* sp. extract. Also, the metal-containing antioxidant includes copper or zinc as a ligand to an organic moiety. Additionally, or alternatively, the non-metal (metalloid) selenium may also be included in the composition.

In typical embodiments, the purine alkaloid of the composition for reducing cellular ageing, improving cellular stress resilience, and/or increasing longevity is theacrine, liberine, methylliberine, theobromine, theophylline, or caffeine. In other typical embodiments, the isothiocyanate or thioglucoside is allyl isothiocyanate or 2-phenylethyl isothiocyanate. In still other typical embodiments, the metal-containing antioxidant is a copper-(I)-nicotinate complex or a nutritionally acceptable copper-II-complex or chelate.

Preferably, the contemplated composition for reducing cellular ageing, improving cellular stress resilience, and/or increasing longevity also includes one or more additional nutritional ingredients. Examples of one or more additional nutritional ingredients include a ketogenic compound.

Exemplary ketogenic compounds include acetoacetate, tributyrin, beta-hydroxybutyrate (BHB), butyrate, polyhydroxybutyrate (PHB).

The contemplated composition for reducing cellular ageing, improving cellular stress resilience, and/or increasing longevity may also include a SIRT enhancing agent as one or more nutritional ingredients. Exemplary SIRT enhancing agents include fisetin, resveratrol, quercetin, and/or a catechin.

As disclosed in more detail herein, the contemplated composition may include a combination of additional ingredients conferring a combinatorial or even a synergistic effect. Additional nutritional ingredients also include a NAD enhancing agent.

For improved efficacy the contemplated composition for reducing cellular ageing, improving cellular stress resilience, and/or increasing longevity includes a cytoprotective formulation of a combination of (a) a purine alkaloid, (b) an isothiocyanate or thioglucoside, and (c) a metal-containing antioxidant, and (d) additional nutritional ingredients including selenium tributryin, and/or BHB; and wherein the cytoprotective formulation is formulated for oral administration with a nutritionally or pharmaceutically acceptable carrier.

The inventive subject matter also includes methods of reducing cellular ageing, improving cellular stress resilience, and/or increasing longevity in a mammal, in which the mammal is administered the presently contemplated cytoprotective composition as disclosed in various embodiments herein. The method may include administering the cytoprotective composition to the mammal in an amount effective to reduce cellular ageing, inflammation, improve cellular stress resilience, and/or increase longevity in a mammal; wherein the cytoprotective composition includes a cytoprotective formulation comprising a combination of (a) a purine alkaloid, (b) an isothiocyanate or thioglucoside, (c) a metal-containing antioxidant, and optionally (d) one or more additional ingredients including selenium, tributyrin, and/or BHB; wherein the cytoprotective formulation is formulated for oral administration with a nutritionally or pharmaceutically acceptable carrier.

Additionally, the contemplated subject matter includes a method of reducing oxidative stress, autophagy, and/or increasing or maintaining antioxidant activity in a cell of a mammal. This method includes administering a cytoprotective composition to the mammal in an amount effective to reduce oxidative stress; wherein the cytoprotective composition includes a cytoprotective formulation comprising a combination of (a) a purine alkaloid, (b) an isothiocyanate or thioglucoside, (c) a metal-containing antioxidant, and optionally (d) one or more additional ingredients including selenium, tributyrin, and/or BHB.

The inventive subject matter also includes methods and compositions for increasing nicotinamide adenine dinucleotide (NAD+) enzyme activity in a cell of a mammal, including administering the cytoprotective composition as disclosed herein to the mammal in an amount effective to increase increasing nicotinamide adenine dinucleotide (NAD+) enzyme activity. Contemplated methods for increasing NAD+ activity also include inhibiting NAD+ degradation. Typical methods for inhibiting NAD+ degradation include inhibiting CD38 and/or CD157 activity in the cell Most typically, but not necessarily, the composition may be formulated as a capsule, a tablet, or as a powder, and/or delivers between 25-1,500 mg of the cytoprotective formulation in a single dosage unit. For example, the at least 50 wt % of the composition may be the cytoprotective formulation or a single dosage unit comprises at least 50 mg of the cytoprotective formulation. In other examples, the purine alkaloid may be present in an amount of between 5-500 mg in a single dosage unit, the isothiocyanate or thioglucoside may be present in an amount of between 25-1,000 mg in a single dosage unit, and/or the metal-containing antioxidant may be present in an amount of between 1 mcg-100 mg in a single dosage unit.

Various objects, features, aspects, and advantages will become more apparent from the following detailed description of preferred embodiments, along with the accompanying drawing in which like numerals represent like components.

8

Figure 6A:
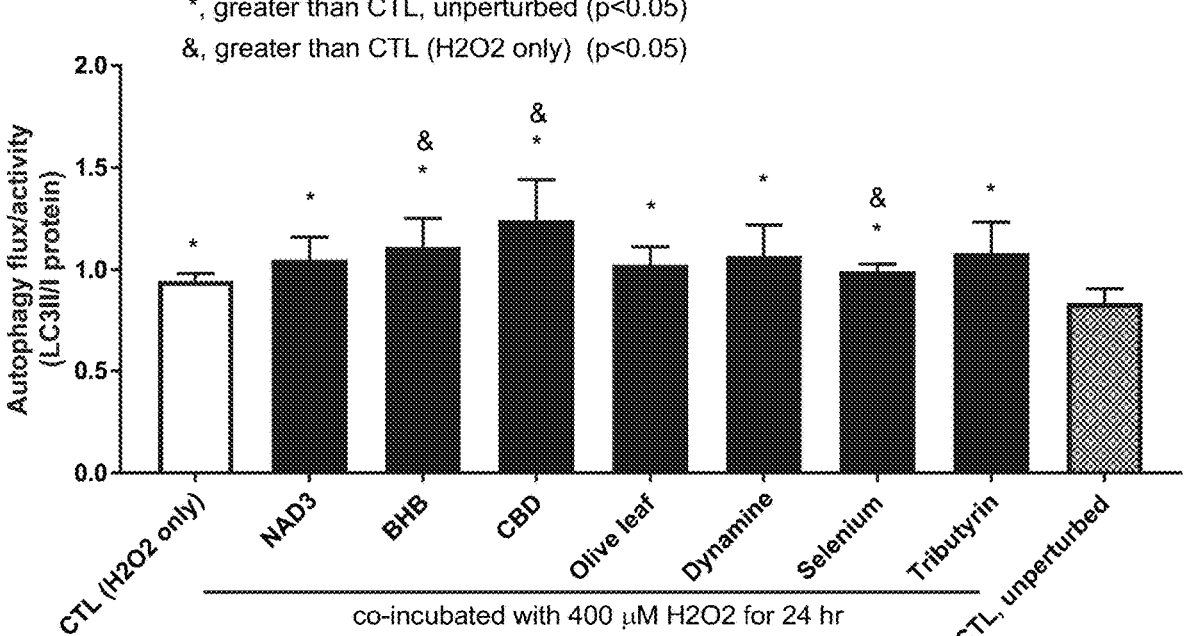
FIG. 6A depicts exemplary results for autophagy for cells incubated without hydrogen peroxide (H2O2) (CTL, unperturbed), cells incubated with H2O2, and cells co-incubated with NAD3, BHB, CBD, olive leaf, dynamine, selenium, or tributyrin as indicated.
Figure 6B:
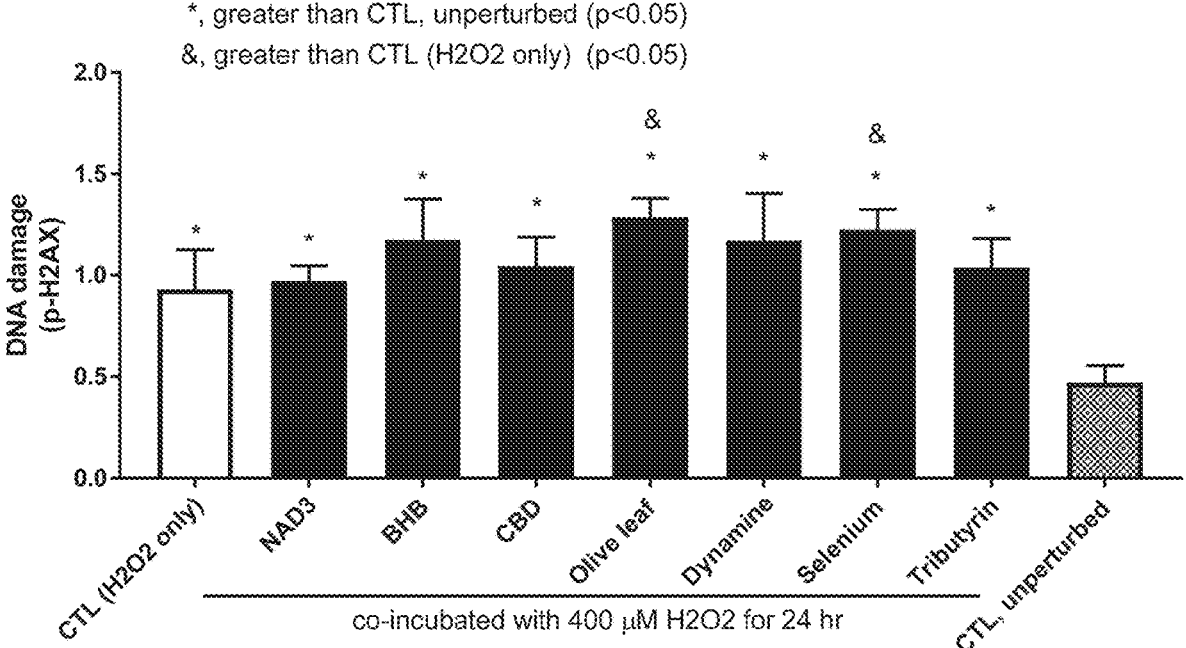

FIG. 6B depicts exemplary results for DNA damage for cells incubated without hydrogen peroxide (H2O2) (CTL, unperturbed), cells incubated with H2O2, and cells co-incubated with NAD3, BHB, CBD, olive leaf, dynamine, selenium, or tributyrin as indicated.

Figure 6C:
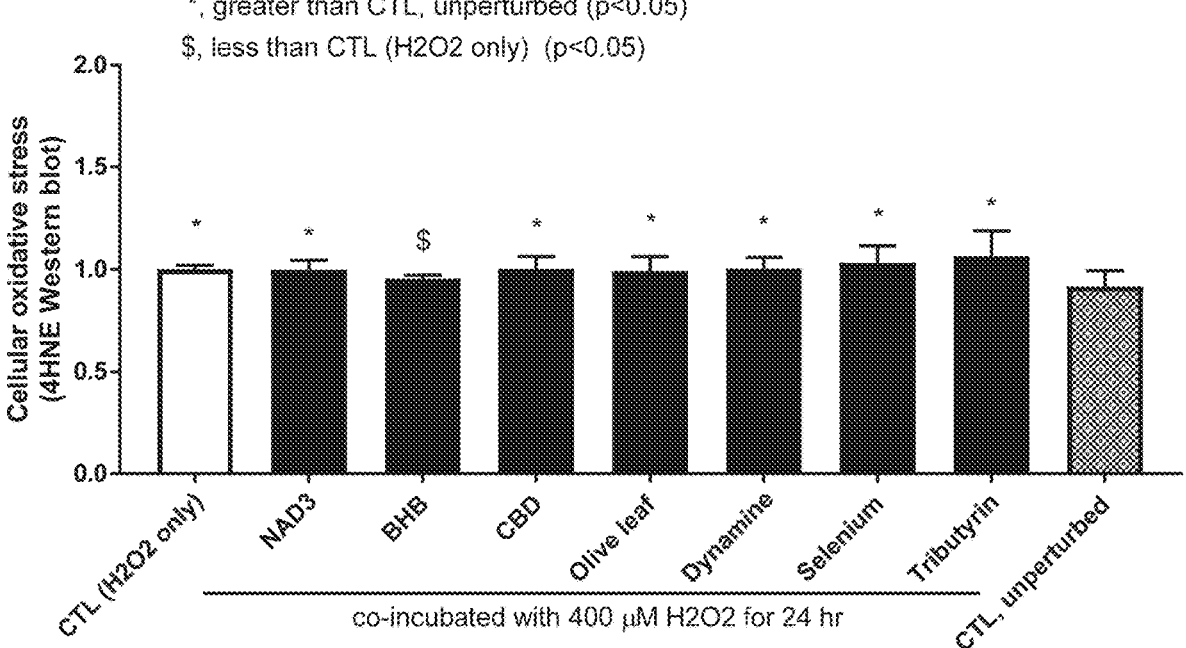

FIG. 6C depicts exemplary results for cellular oxidative stress for cells incubated without hydrogen peroxide (H2O2) (CTL, unperturbed), cells incubated with H2O2, and cells co-incubated with NAD3, BHB, CBD, olive leaf, dynamine, selenium, or tributyrin as indicated.

Figure 7A:
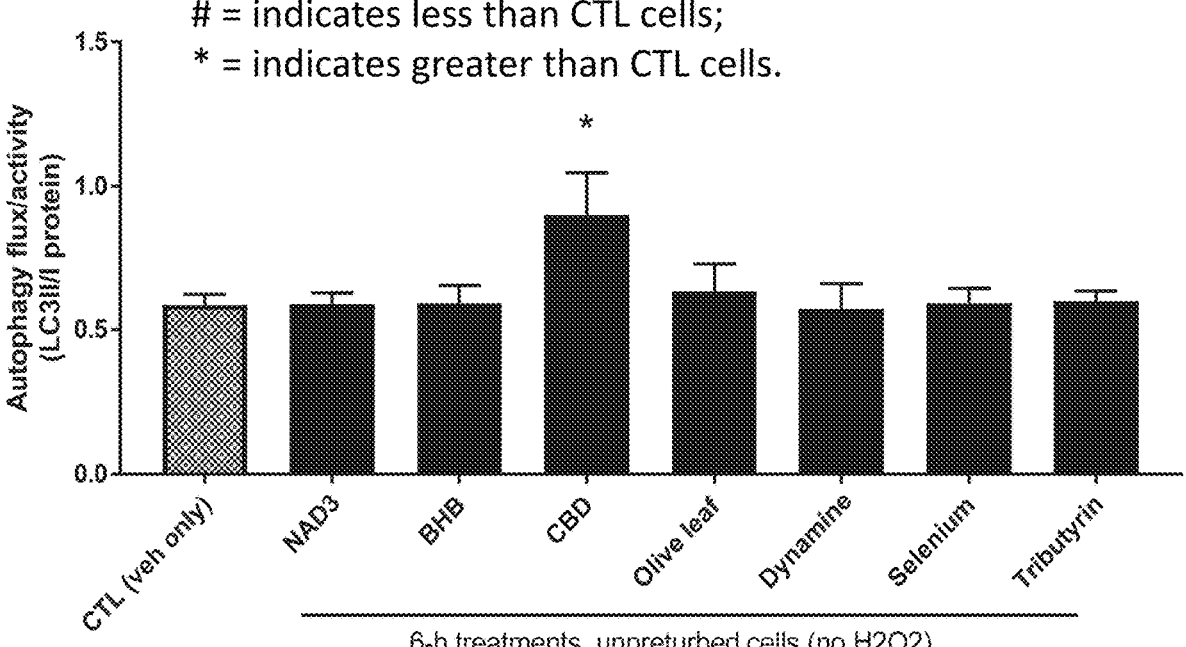

FIG. 7A depicts exemplary results for autophagy for cells incubated for 6 hours without hydrogen peroxide (H2O2) (CTL, vehicle (veh) only), and cells incubated with NAD3, BHB, CBD, olive leaf, dynamine, selenium, or tributyrin as indicated.

Figure 7B:
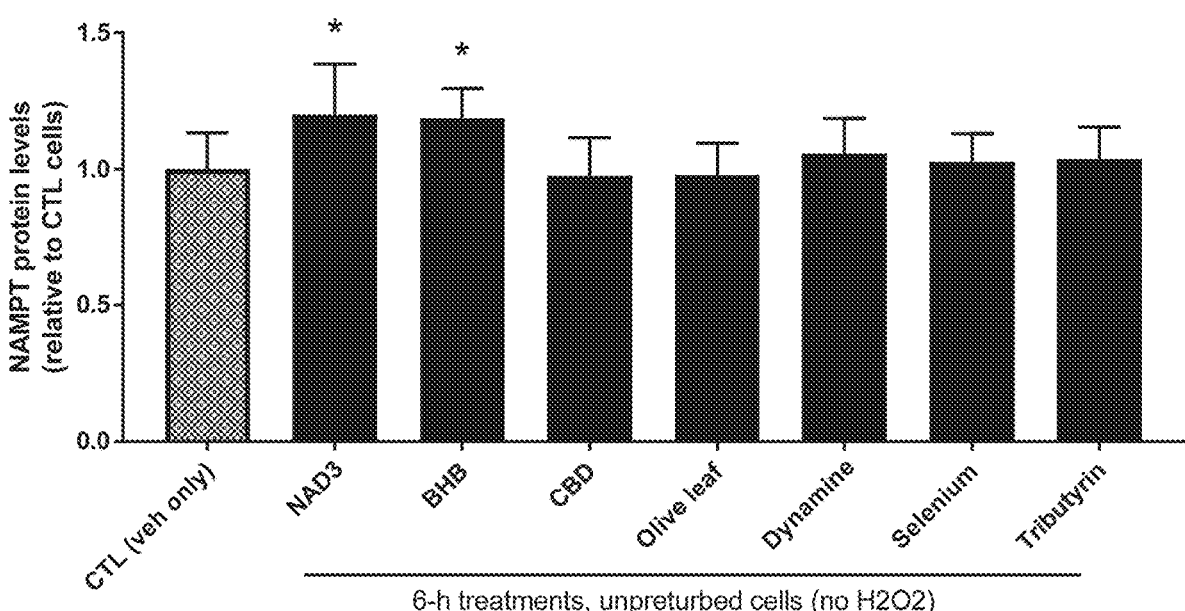

FIG. 7B depicts exemplary results for quantifying NAMPT protein levels in cells incubated for 6 hours without hydrogen peroxide (H2O2) (CTL, vehicle (veh) only), and cells incubated with NAD3, BHB, CBD, olive leaf, dynamine, selenium, or tributyrin as indicated.

Figure 7C:
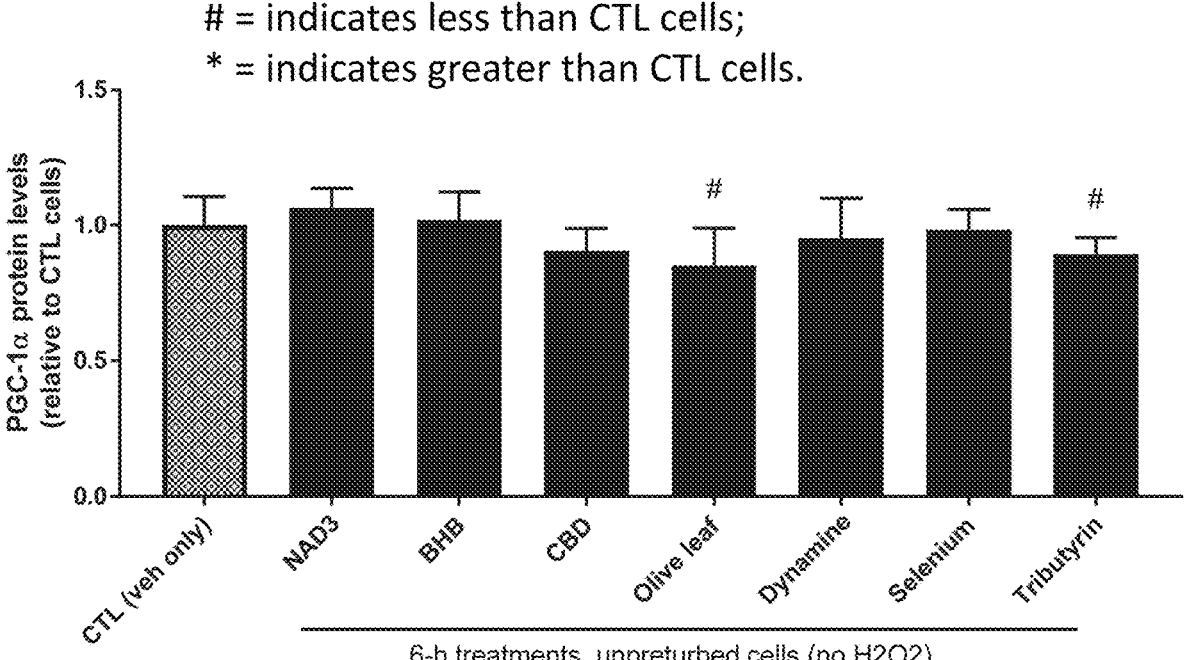

FIG. 7C depicts exemplary results for quantifying PGC1α protein levels in cells incubated for 6 hours without hydrogen peroxide (H2O2) (CTL, vehicle (veh) only), and cells incubated with NAD3, BHB, CBD, olive leaf, dynamine, selenium, or tributyrin as indicated.

Figure 8A:
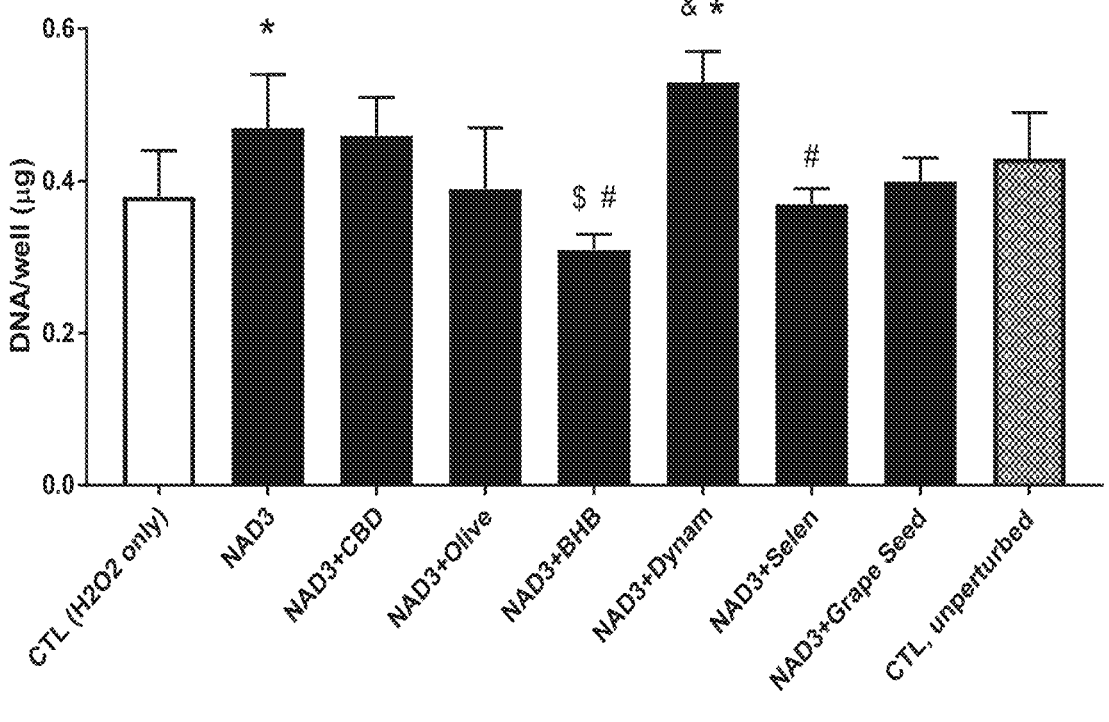

FIG. 8A depicts exemplary results for cell viability (DNA/well (ug)) for cells incubated without hydrogen peroxide (CTL, unperturbed), cells incubated with hydrogen peroxide (H2O2), and cells co-incubated with NAD3, NAD3+CBD, NAD3+olive leaf, NAD3+BHB, NAD3+dynamine, NAD3+selenium, or NAD3+grape seed, as indicated.

Figure 8B:
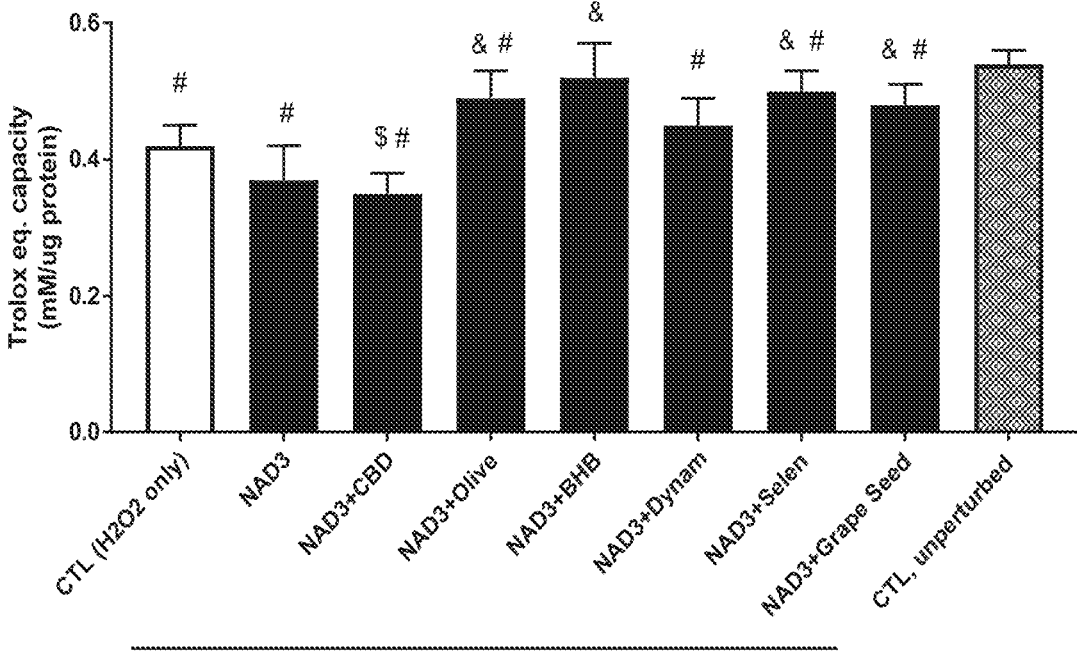

FIG. 8B depicts exemplary results for total antioxidant capacity (Trolox) for cells incubated without hydrogen peroxide (H2O2) (CTL, unperturbed), cells incubated with H2O2, and cells co-incubated with NAD3, NAD3+CBD, NAD3+olive leaf, NAD3+BHB, NAD3+dynamine, NAD3+selenium, or NAD3+grape seed, as indicated.

Figure 9A:
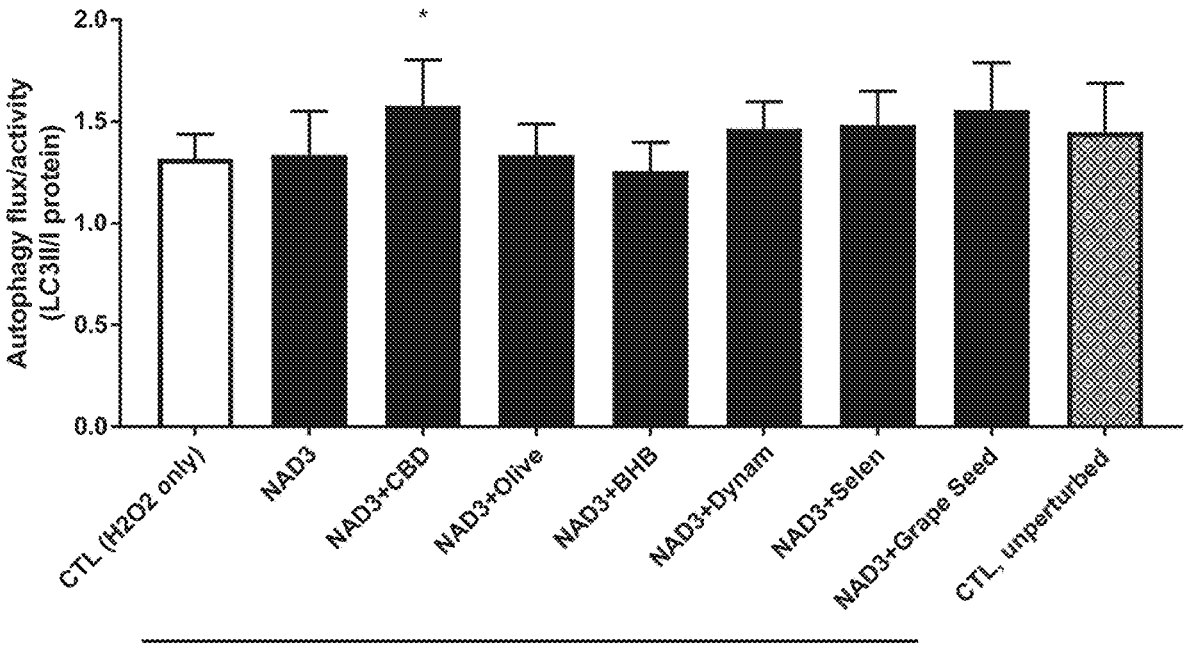

FIG. 9A depicts exemplary results for autophagy for cells incubated without hydrogen peroxide (H2O2) (CTL, unperturbed), cells incubated with H2O2, and cells co-incubated with NAD3, NAD3+CBD, NAD3+olive leaf, NAD3+BHB, NAD3+dynamine, NAD3+selenium, or NAD3+grape seed, as indicated.

Figure 9B:
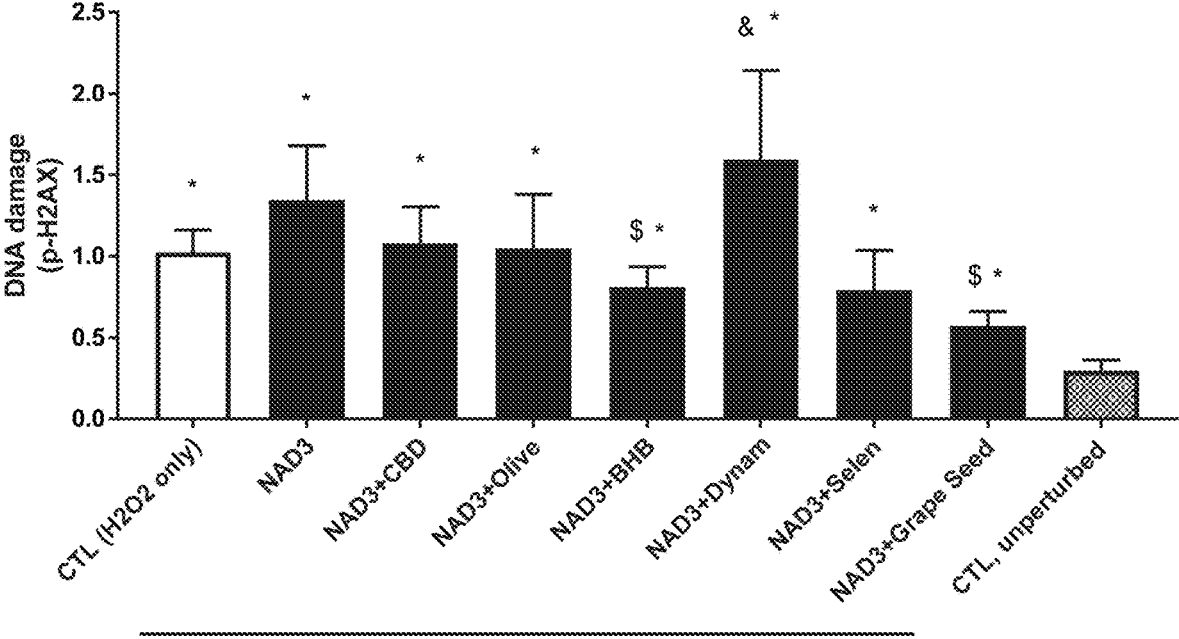

FIG. 9B depicts exemplary results for DNA damage for cells incubated without hydrogen peroxide (H2O2) (CTL, unperturbed), cells incubated with H2O2, and cells co-incubated with NAD3, NAD3+CBD, NAD3+olive leaf, NAD3+BHB, NAD3+dynamine, NAD3+selenium, or NAD3+grape seed, as indicated.

Figure 9C:
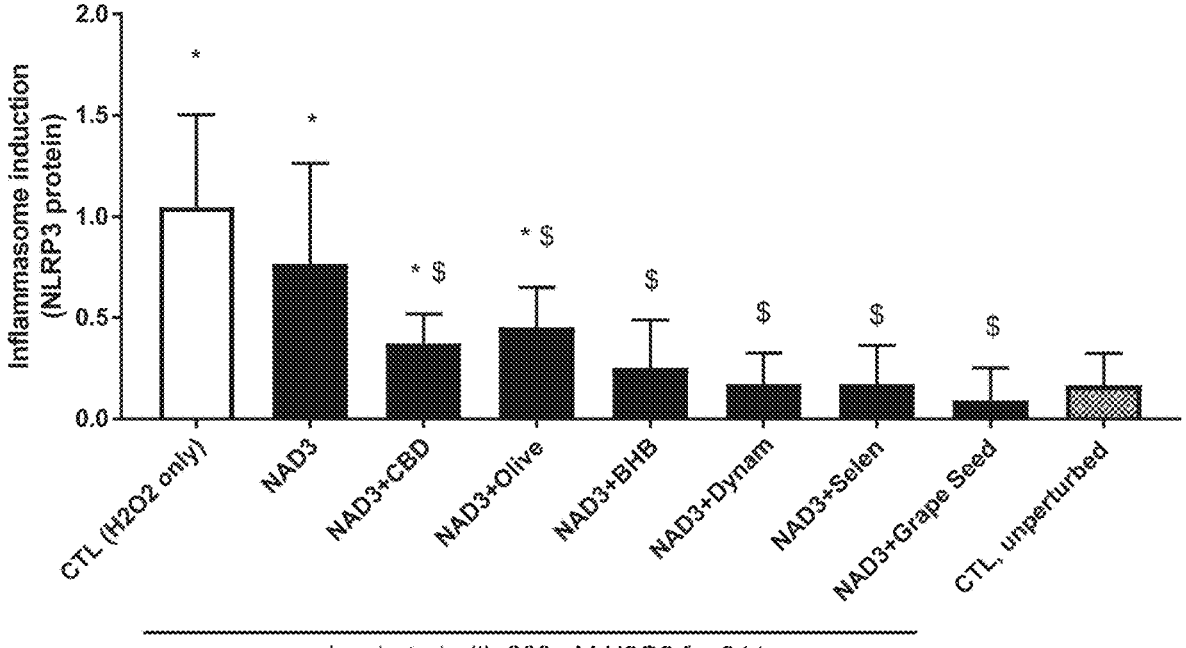

FIG. 9C depicts exemplary results for quantifying inflammasome induction by measuring the amount of NLRP3 protein in cells incubated without hydrogen peroxide (H2O2) (CTL, unperturbed), cells incubated with H2O2, and cells co-incubated with NAD3, NAD3+CBD, NAD3+olive leaf, NAD3+BHB, NAD3+dynamine, NAD3+selenium, or NAD3+grape seed, as indicated.

Figure 10A:
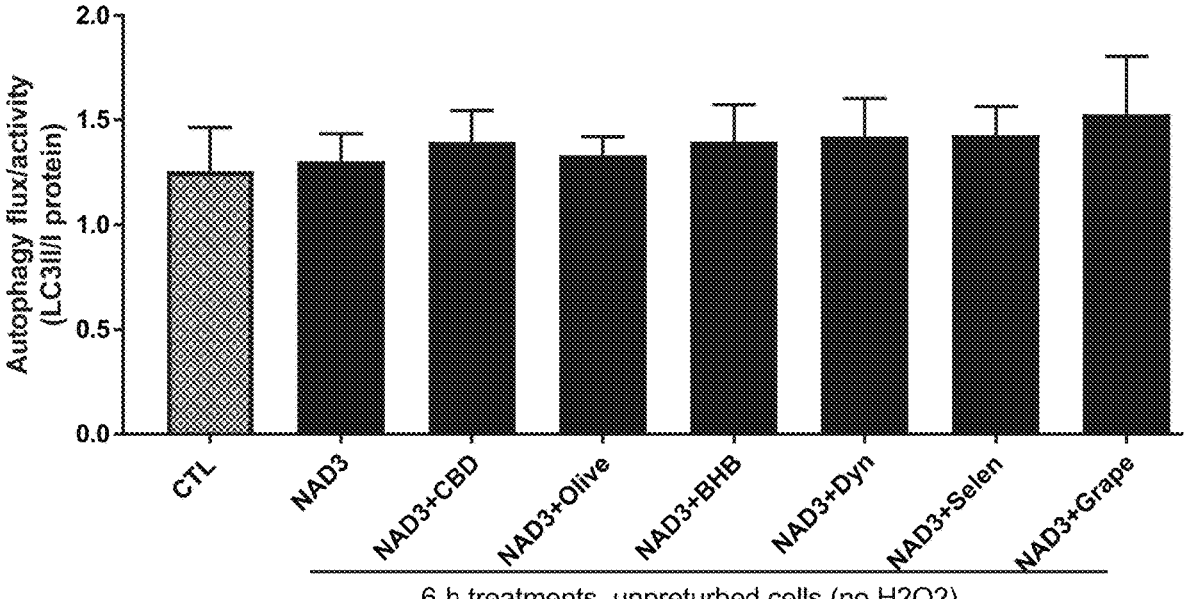

FIG. 10A depicts exemplary results for autophagy for cells incubated for 6 hours without hydrogen peroxide (H2O2) (CTL), and cells incubated with NAD3, NAD3+CBD, NAD3+olive leaf, NAD3+BHB, NAD3+dynamine, NAD3+selenium, or NAD3+grape seed, as indicated.

Figure 10B:
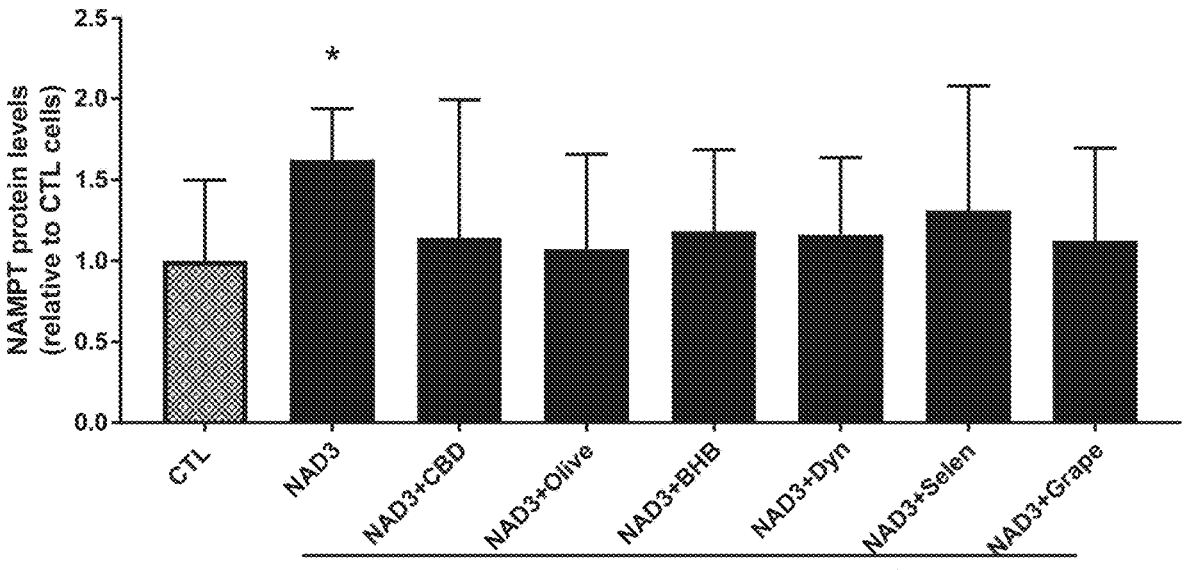

FIG. 10B depicts exemplary results for quantifying NAMPT protein levels in cells incubated for 6 hours without hydrogen peroxide (H2O2) (CTL), and cells incubated with NAD3, NAD3+CBD, NAD3+olive leaf, NAD3+BHB, NAD3+dynamine, NAD3+selenium, or NAD3+grape seed, as indicated.

Figure 10C:
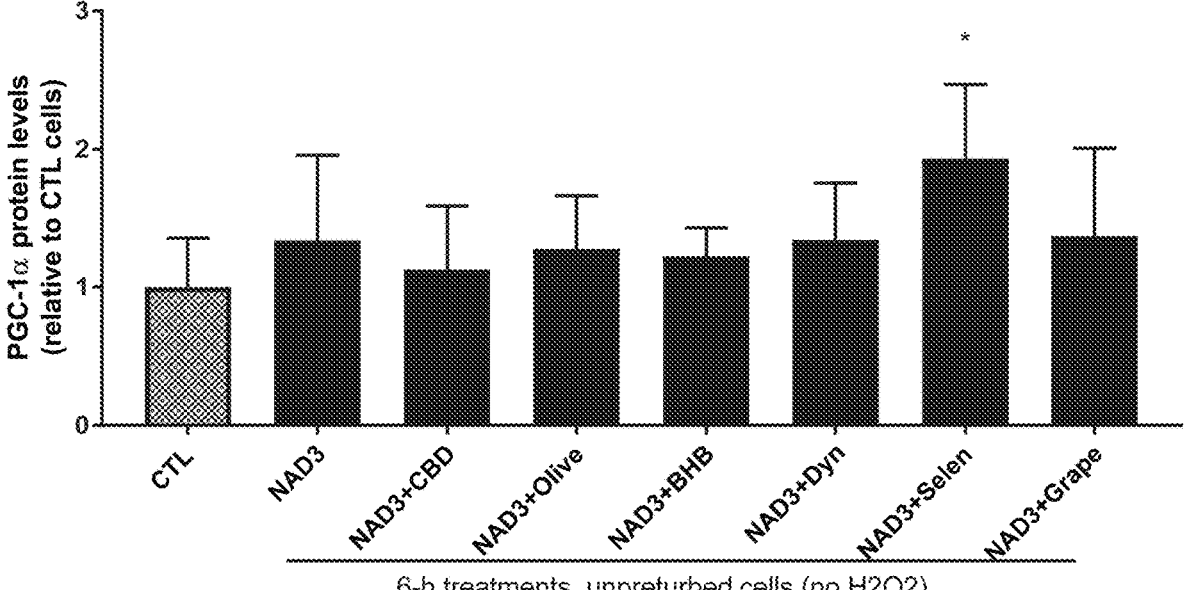

FIG. 10C depicts exemplary results for quantifying PGC1α protein levels in cells incubated for 6 hours without hydrogen peroxide (H2O2) (CTL), and cells incubated with NAD3, NAD3+CBD, NAD3+olive leaf, NAD3+BHB, NAD3+dynamine, NAD3+selenium, or NAD3+grape seed, as indicated.

Figure 10D:
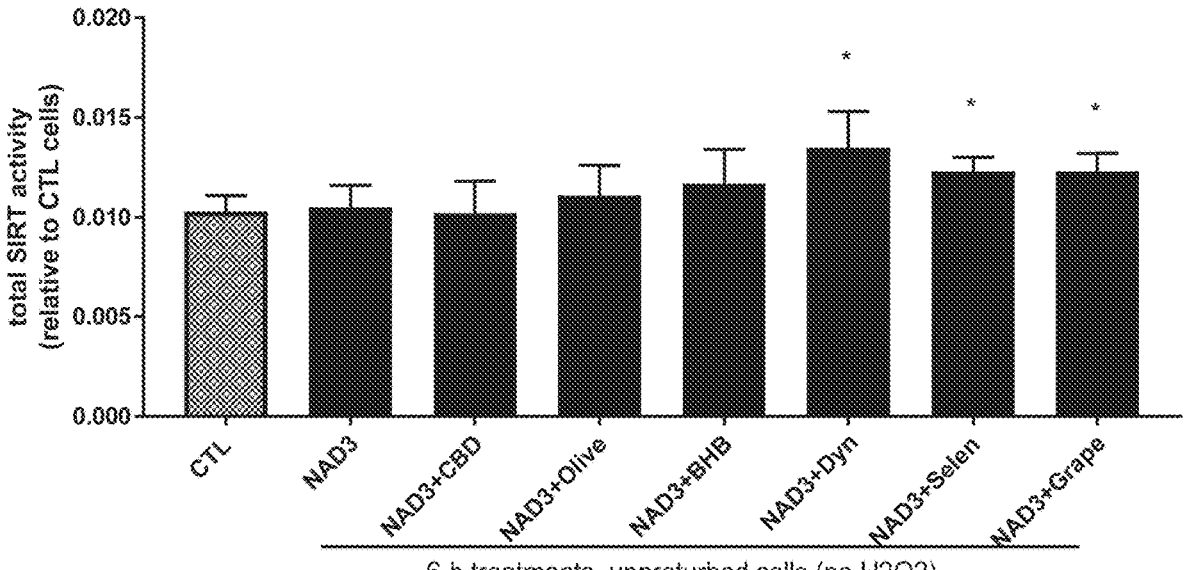

FIG. 10D depicts exemplary results for quantifying total SIRT activity in cells incubated for 6 hours without hydrogen peroxide (H2O2) (CTL), and cells incubated with NAD3, NAD3+CBD, NAD3+olive leaf, NAD3+BHB, NAD3+dynamine, NAD3+selenium, or NAD3+grape seed, as indicated.

Figure 11A:
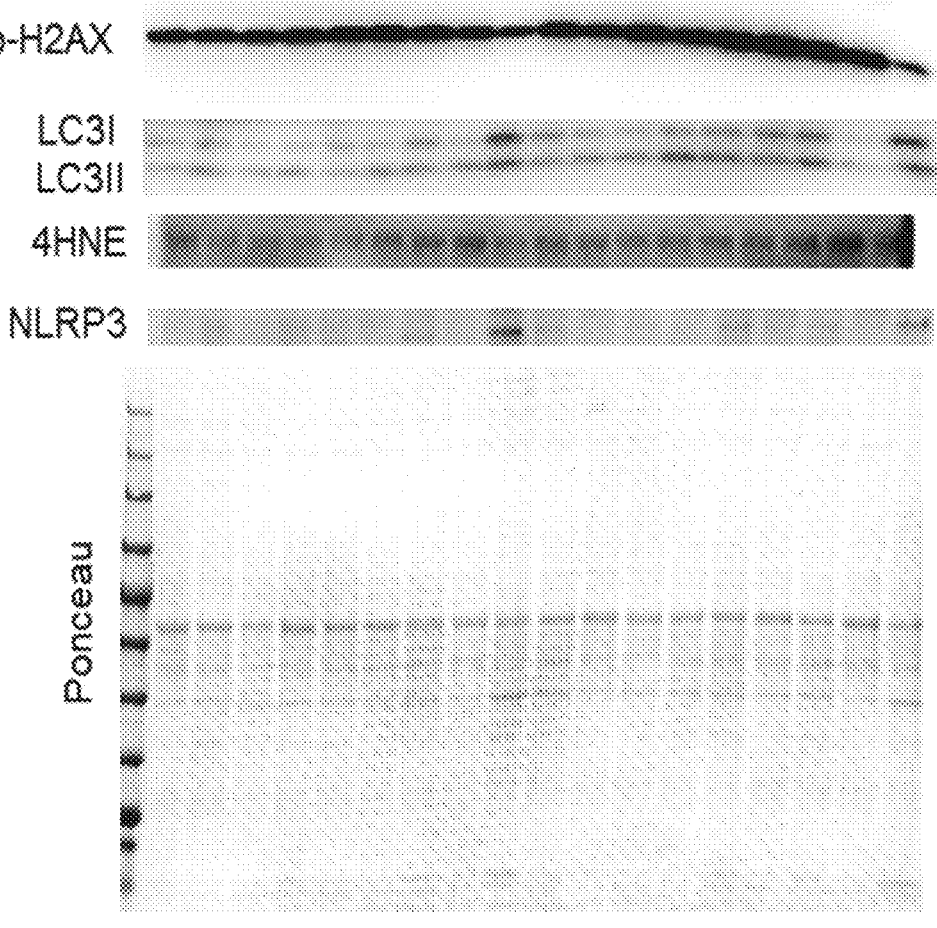

FIG. 11A depicts representative protein gels of C2C12 (muscle cells) with Western blotting analysis shown for p-H2AX, LC3I, LC3II, 4HNE, and NLRP3, and Ponceau protein staining, as indicated.

Figure 11B:
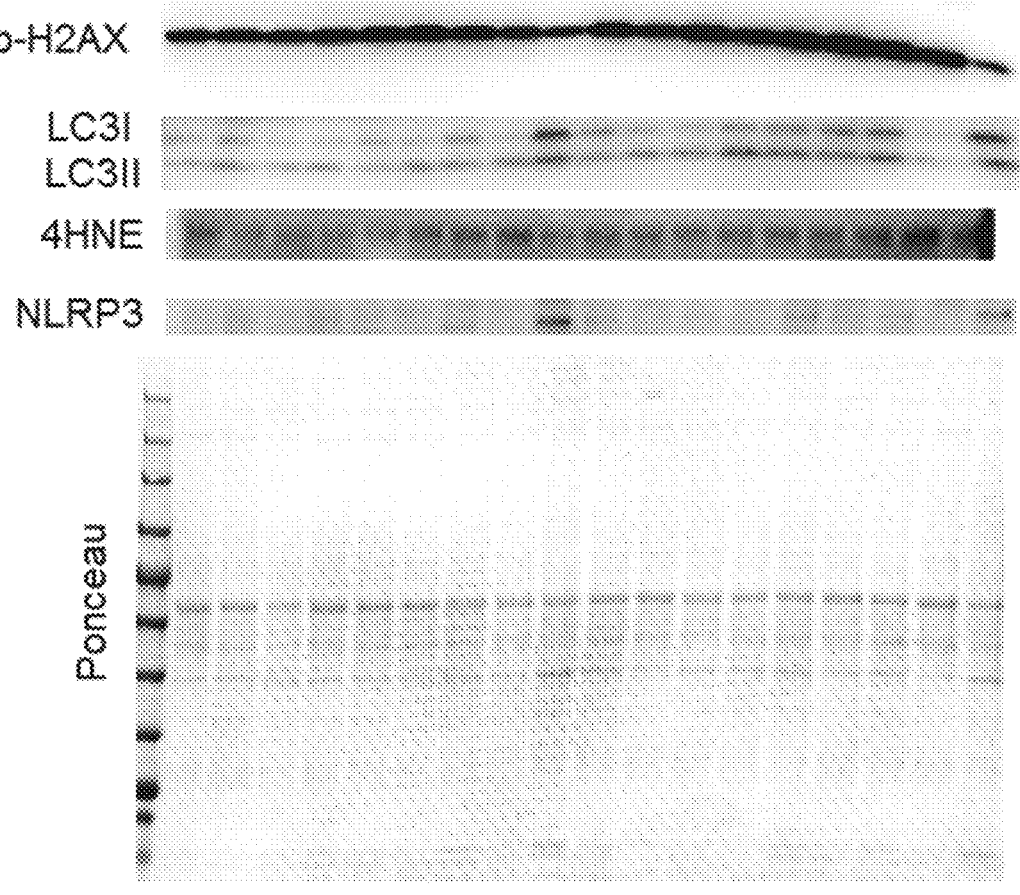

FIG. 11B depicts representative protein gels of EOMA (endothelial cells) with Western blotting analysis shown for p-H2AX, LC3I, LC3II, 4HNE, and NLRP3, and Ponceau protein staining, as indicated.

Figure 12A:
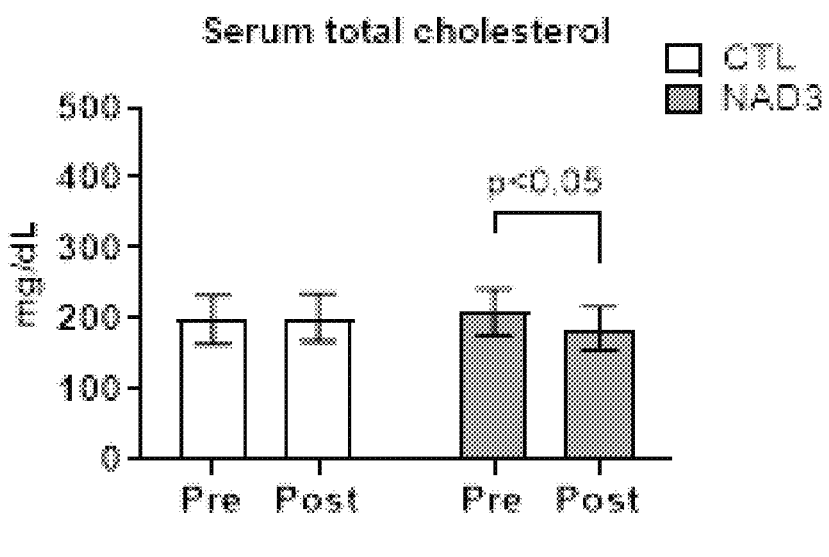

FIG. 12A depicts exemplary results for serum total cholesterol of subjects with and without NAD3 supplementation after 12 weeks.

Figure 12B:
Figure 12B:
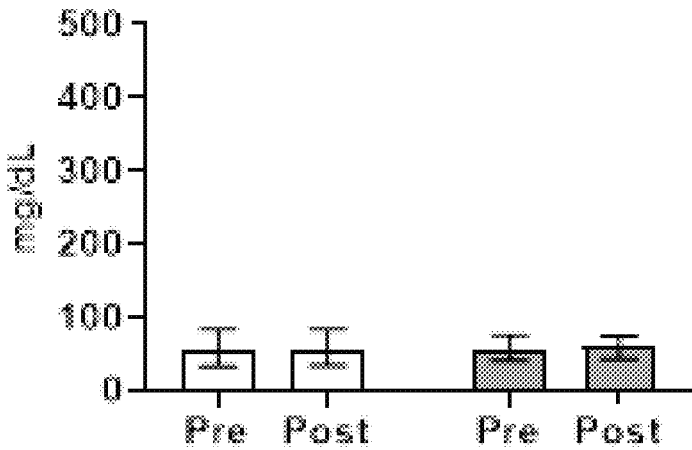

FIG. 12B depicts exemplary results for serum HDL cholesterol of subjects with and without NAD3 supplementation after 12 weeks.

Figure 12C:
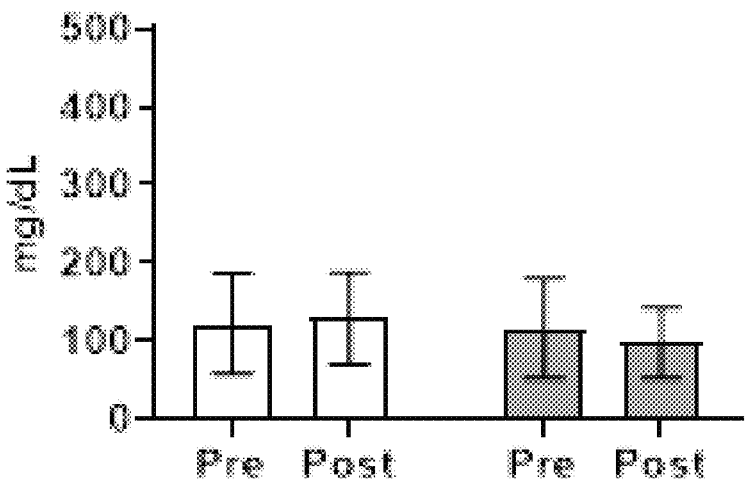

FIG. 12C depicts exemplary results for serum triglycerides of subjects with and without NAD3 supplementation after 12 weeks.

Figure 12D:
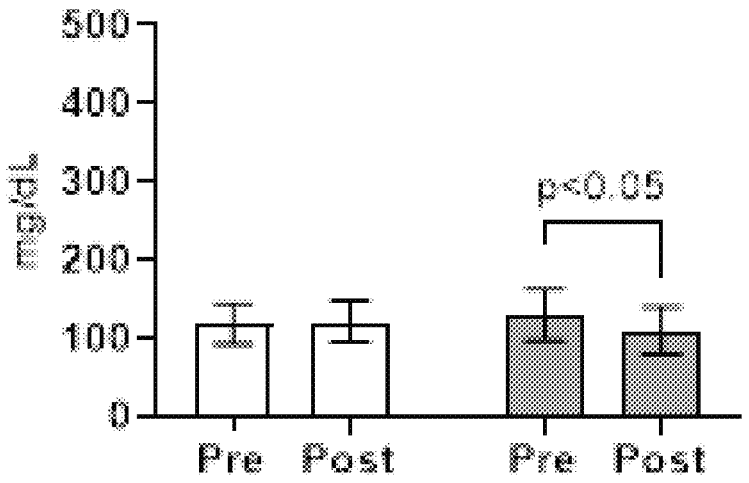

FIG. 12D depicts exemplary results for serum LDL cholesterol of subjects with and without NAD3 supplementation after 12 weeks.

FIG. 13A depicts exemplary results for PBMC telomere lengths of subjects without supplementation after 4 weeks.

FIG. 13B depicts exemplary results for PBMC telomere lengths of subjects with NAD3 supplementation after 4 weeks.

FIG. 13C depicts exemplary results for PBMC telomere lengths of subjects with NAD3-TB supplementation after 4 weeks.

Figure 13D:
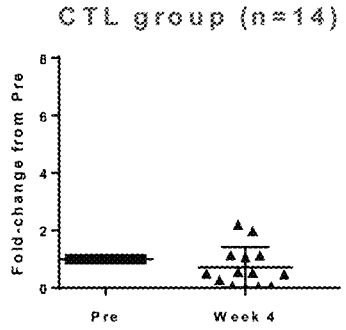
Figure 13D:
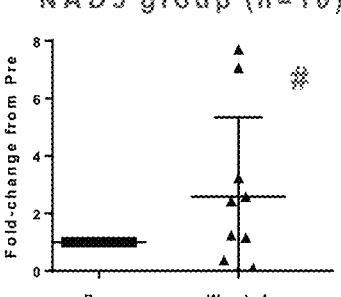
Figure 13D:
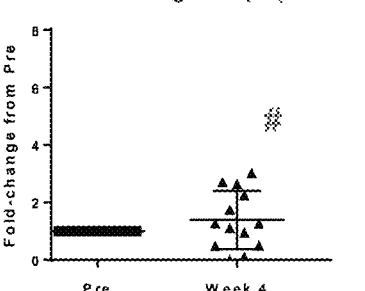
Figure 13D:
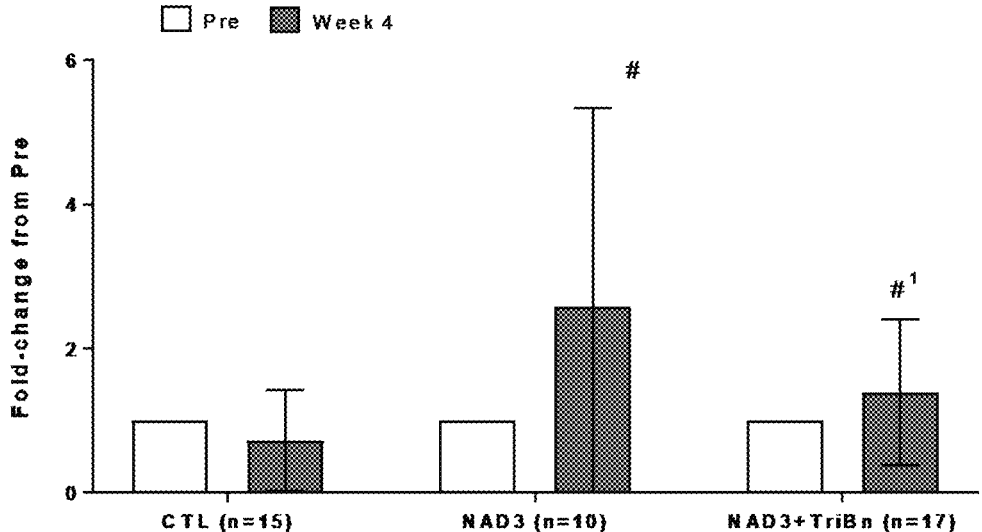

FIG. 13D depicts exemplary results for PBMC telomere lengths of subjects with NAD3 supplementation, with NAD3-TB supplementation, or without either supplementation after 4 weeks.

Figure 14A:
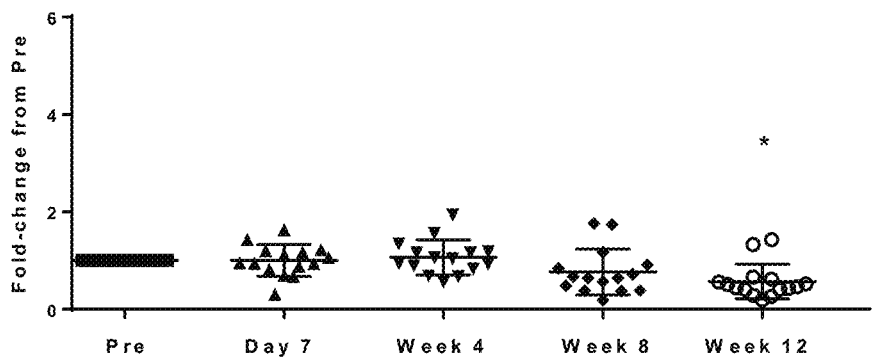

FIG. 14A depicts exemplary results for PBMC global SIRT activity of subjects without supplementation after 1 week, 4 weeks, 8 weeks, and 12 weeks.

Figure 14B:
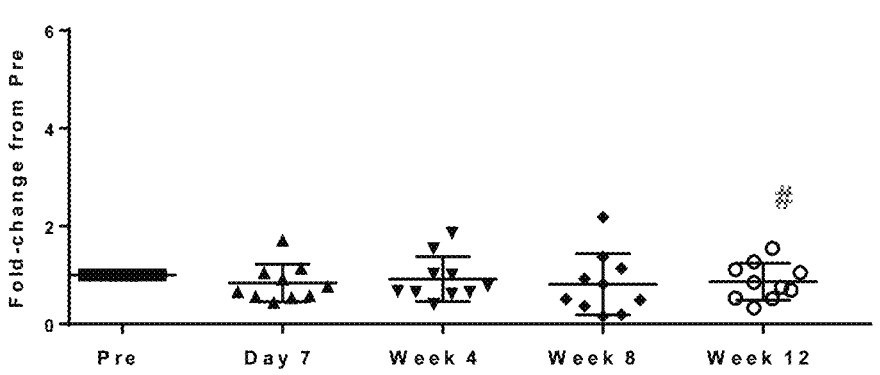

FIG. 14B depicts exemplary results for PBMC global SIRT activity of subjects with NAD3 supplementation after 1 week, 4 weeks, 8 weeks, and 12 weeks.

Figure 14C:
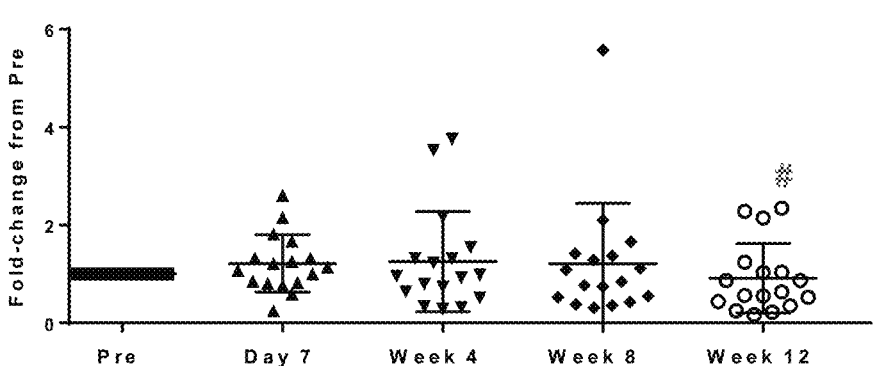

FIG. 14C depicts exemplary results for PBMC global SIRT activity of subjects with NAD3-TB supplementation after 1 week, 4 weeks, 8 weeks, and 12 weeks.

Figure 14D:
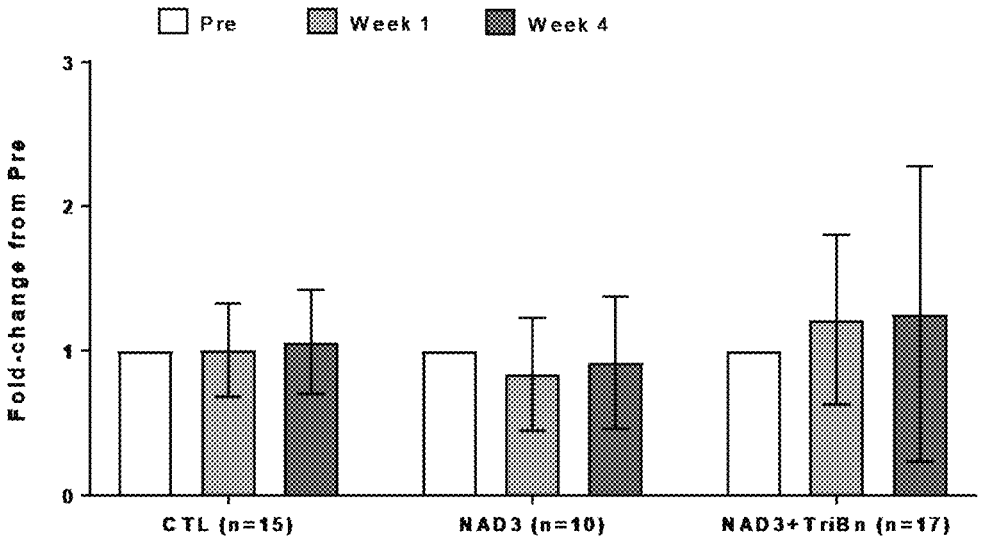

FIG. 14D depicts exemplary results for PBMC global SIRT activity of subjects with NAD3 supplementation, with NAD3-TB supplementation, or without either supplementation, after 1 week and 4 weeks.

Figure 15:
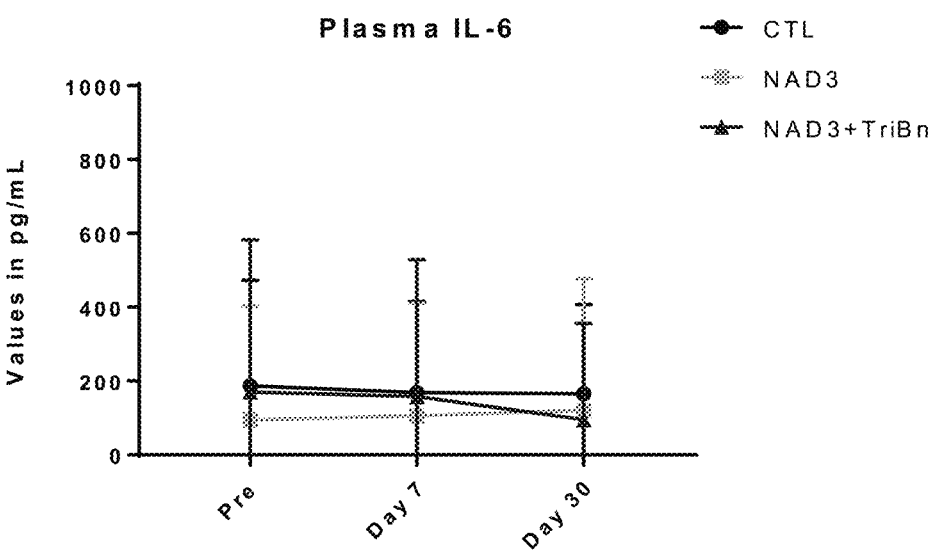

FIG. 15 depicts exemplary results for plasma IL-6 expression in subjects with NAD3 supplementation, with NAD3-TB supplementation, or without either supplementation, after 1 week and 4 weeks.

Figure 16:
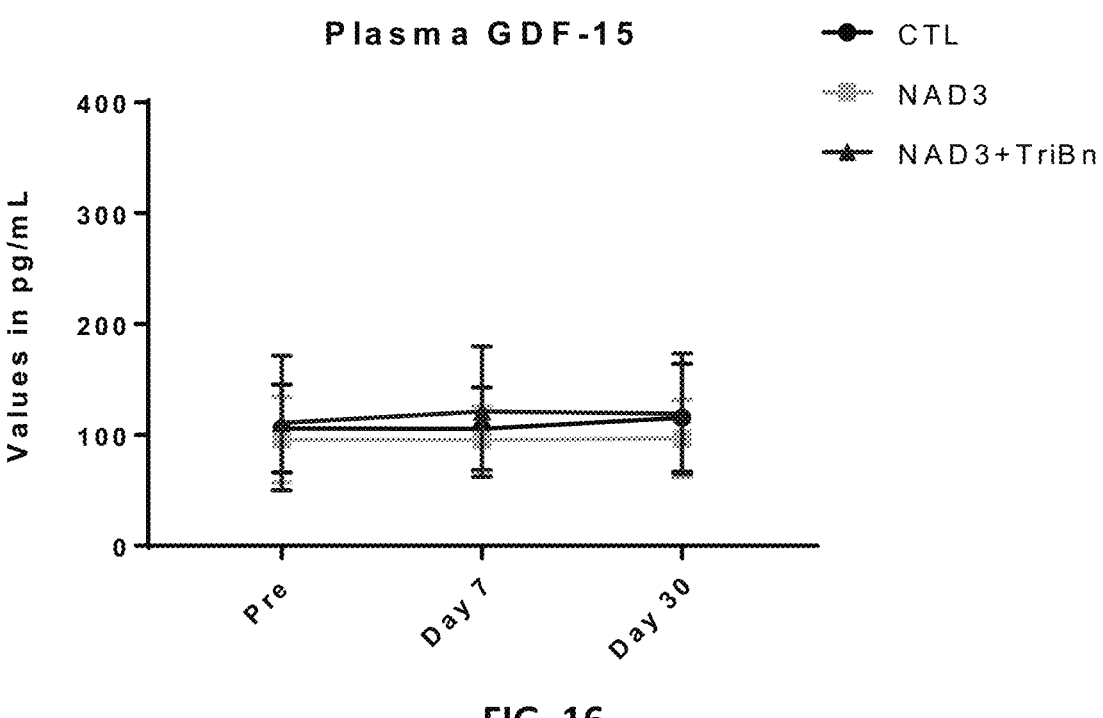

FIG. 16 depicts exemplary results for plasma GDF-15 expression in subjects with NAD3 supplementation, with NAD3-TB supplementation, or without either supplementation, after 1 week and 4 weeks.

Figure 17:
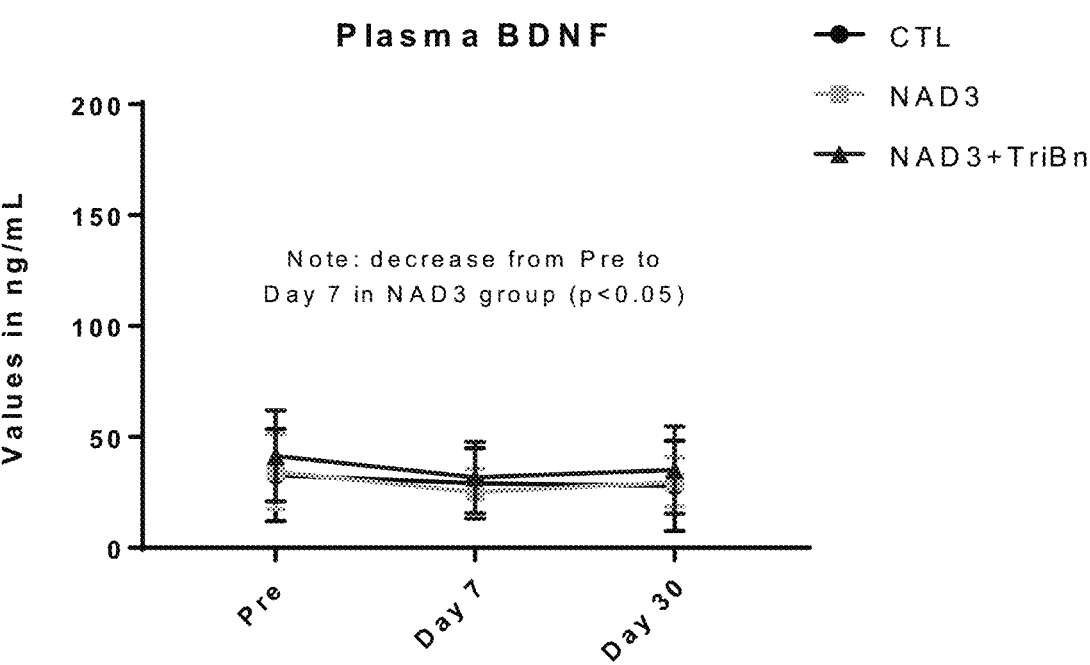

FIG. 17 depicts exemplary results for plasma BDNF expression in subjects with NAD3 supplementation, with NAD3-TB supplementation, or without either supplementation, after 1 week and 4 weeks.

Figure 18:
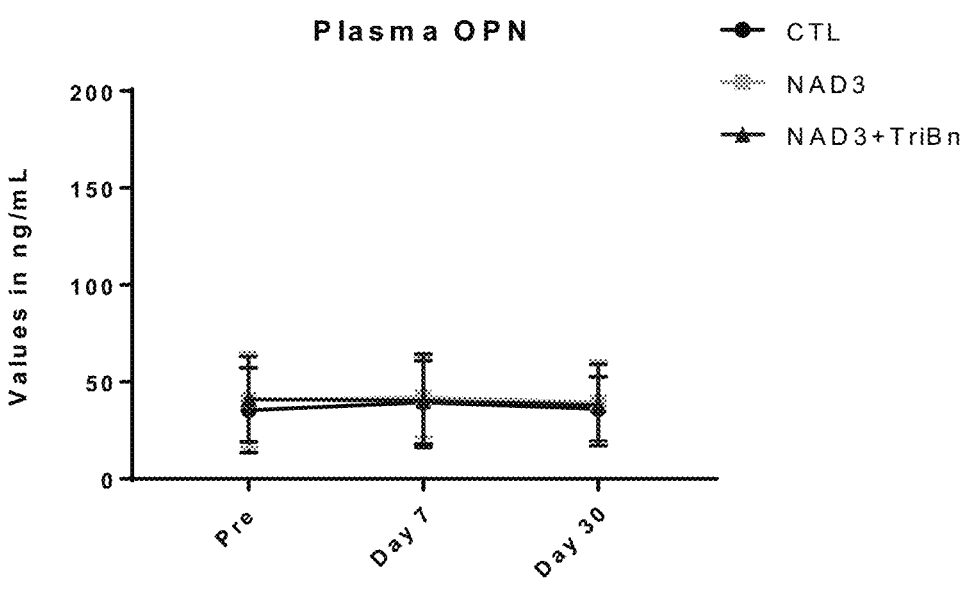

FIG. 18 depicts exemplary results for plasma OPN expression in subjects with NAD3 supplementation, with NAD3-TB supplementation, or without either supplementation, after 1 week and 4 weeks.

Figure 19:
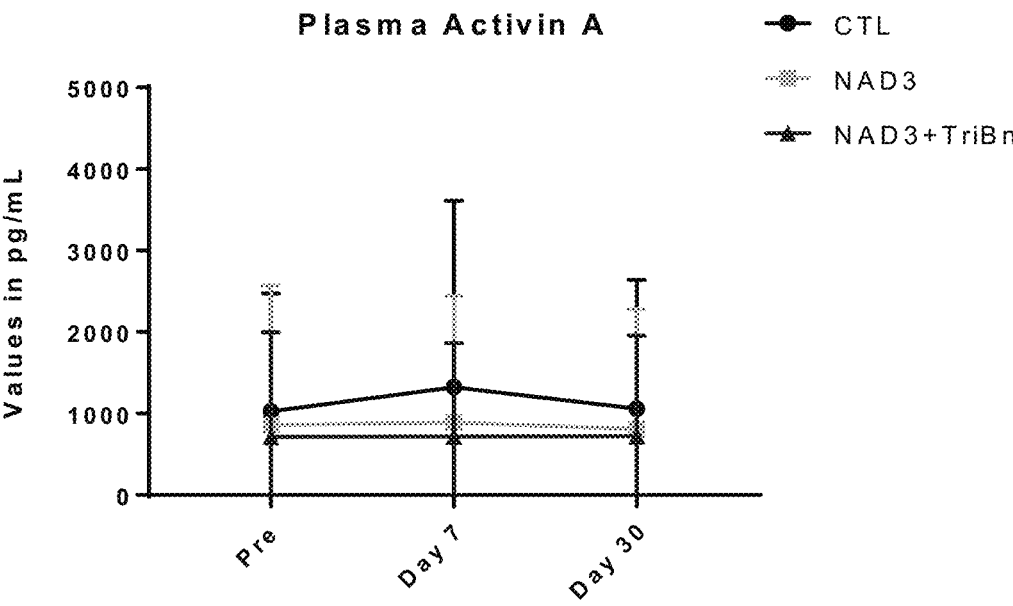

FIG. 19 depicts exemplary results for plasma Activin A expression in subjects with NAD3 supplementation, with NAD3-TB supplementation, or without either supplementation, after 1 week and 4 weeks.

Figure 20:
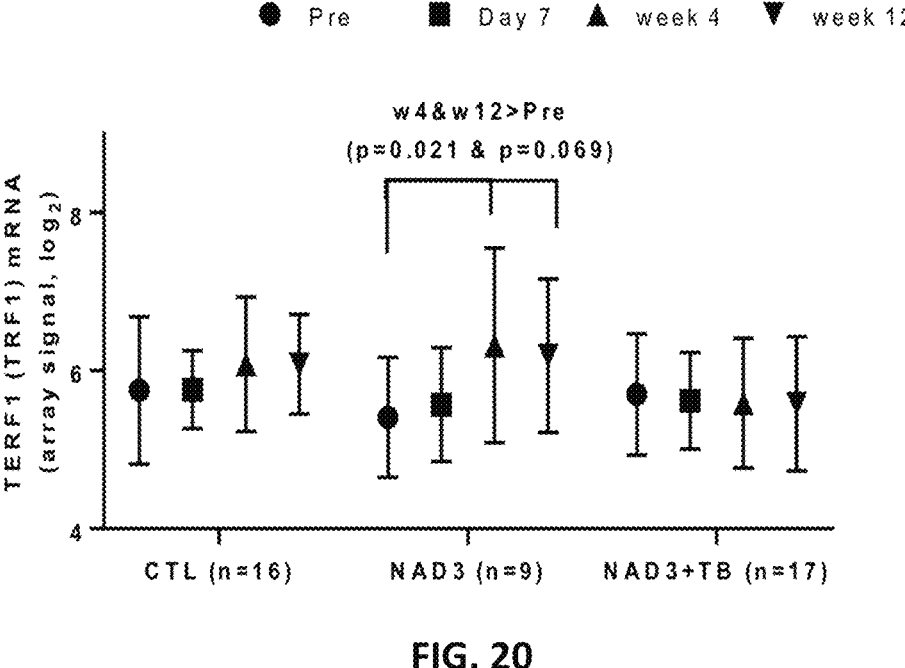

FIG. 20 depicts exemplary results for TRF1 mRNA expression in subjects with NAD3 supplementation, with NAD3-TB supplementation, or without either supplementation, after 1 week, 4 weeks, and 12 weeks.

Figure 21:
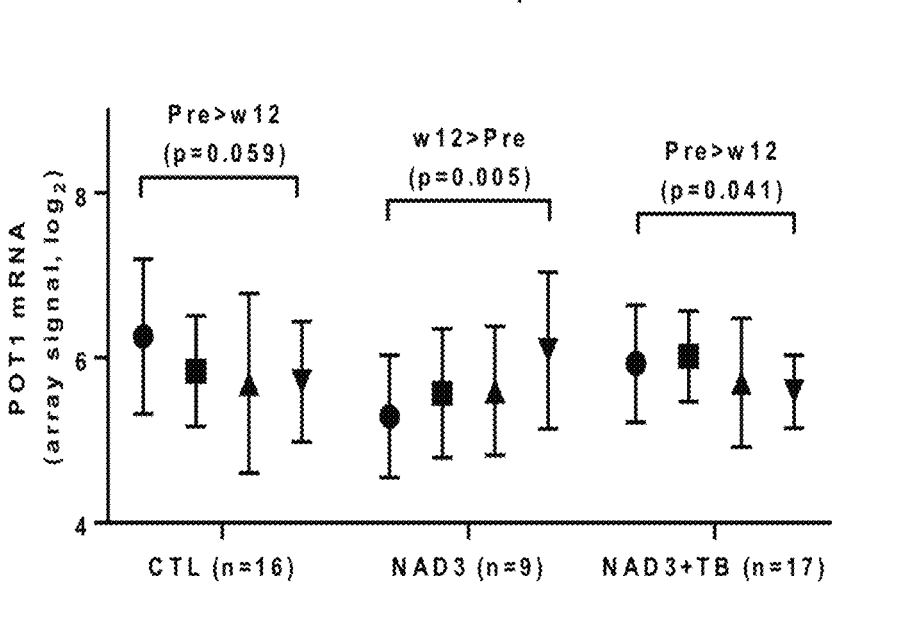

FIG. 21 depicts exemplary results for POT1 mRNA expression in subjects with NAD3 supplementation, with NAD3-TB supplementation, or without either supplementation, after 1 week, 4 weeks, and 12 weeks.

Figure 22:
Figure 22:
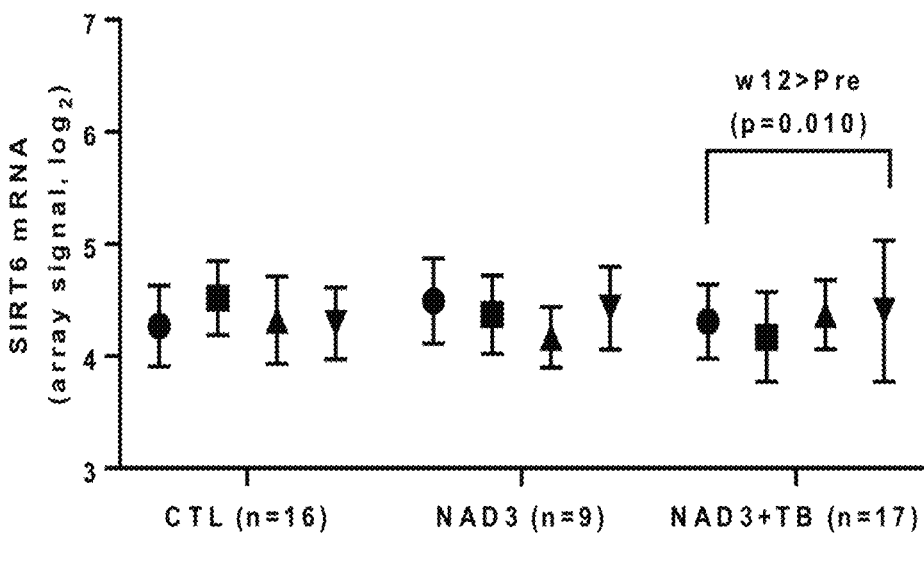

FIG. 22 depicts exemplary results for SIRT6 mRNA expression in subjects with NAD3 supplementation, with NAD3-TB supplementation, or without either supplementation, after 1 week, 4 weeks, and 12 weeks.

Figure 23:
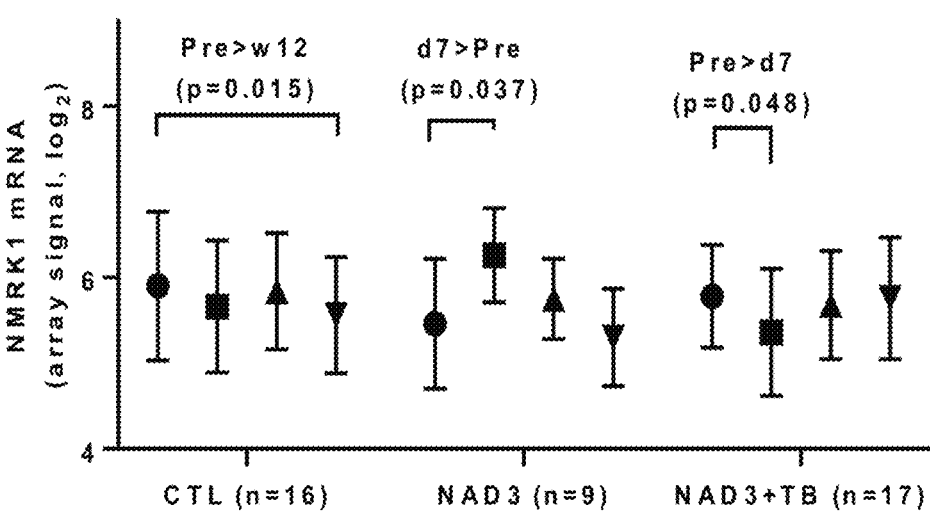

FIG. 23 depicts exemplary results for NMRK1 mRNA expression in subjects with NAD3 supplementation, with NAD3-TB supplementation, or without either supplementation, after 1 week, 4 weeks, and 12 weeks.

Figure 24:
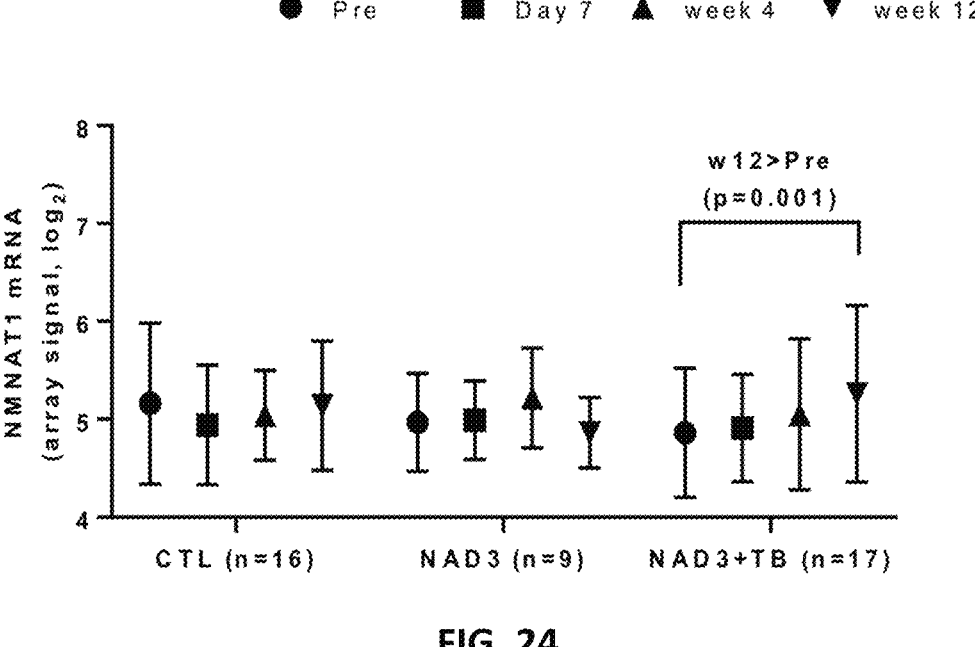

FIG. 24 depicts exemplary results for NMNAT1 mRNA expression in subjects with NAD3 supplementation, with NAD3-TB supplementation, or without either supplementation, after 1 week, 4 weeks, and 12 weeks.

Figure 25:
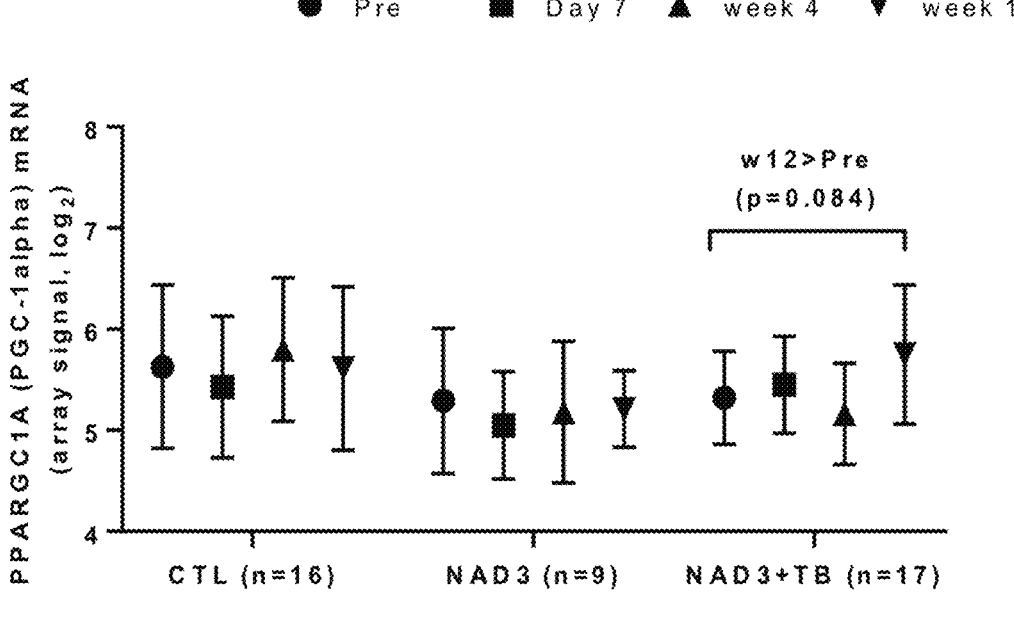

FIG. 25 depicts exemplary results for PGC-1 alpha mRNA expression in subjects with NAD3 supplementation, with NAD3-TB supplementation, or without either supplementation, after 1 week, 4 weeks, and 12 weeks.

Figure 26:
Figure 26:
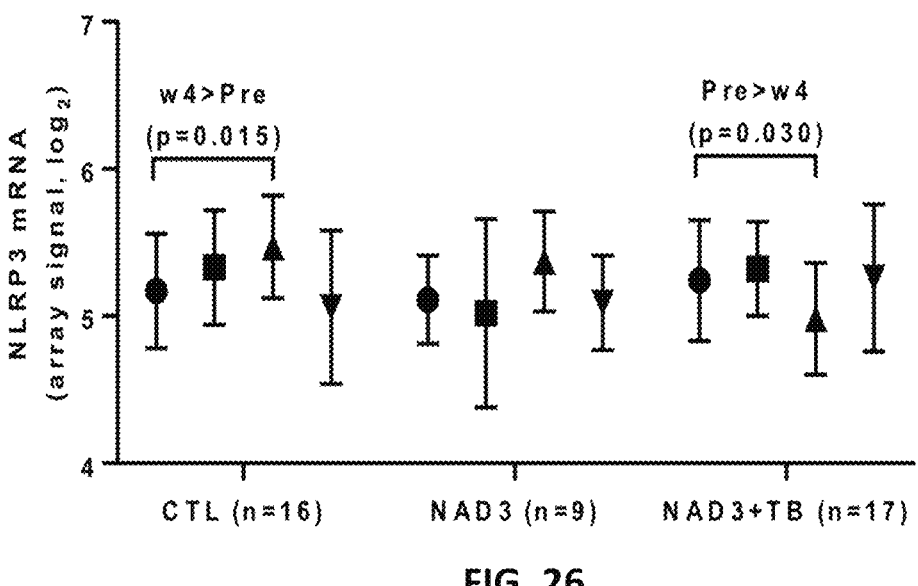

FIG. 26 depicts exemplary results for NLRP3 mRNA expression in subjects with NAD3 supplementation, with NAD3-TB supplementation, or without either supplementation, after 1 week, 4 weeks, and 12 weeks.

Figure 27:
Figure 27:
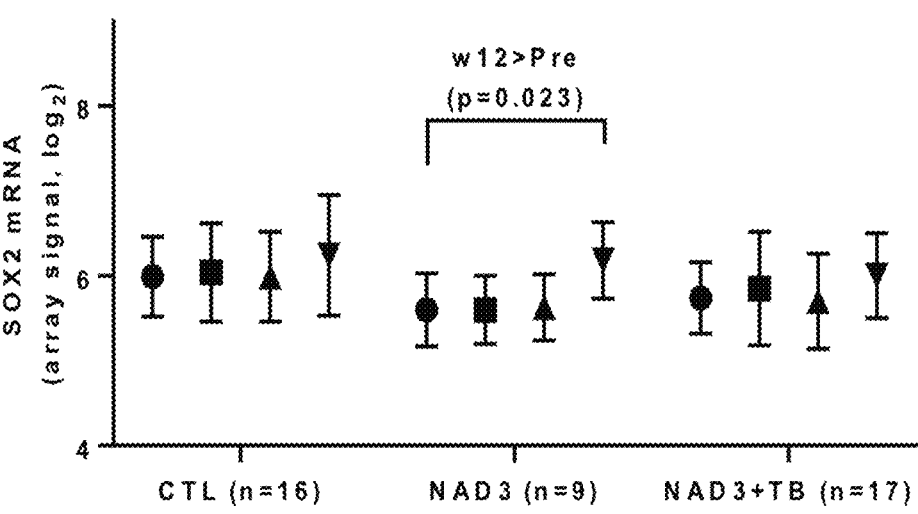

FIG. 27 depicts exemplary results for SOX2 mRNA expression in subjects with NAD3 supplementation, with NAD3-TB supplementation, or without either supplementation, after 1 week, 4 weeks, and 12 weeks.

Figure 28:
Figure 28:
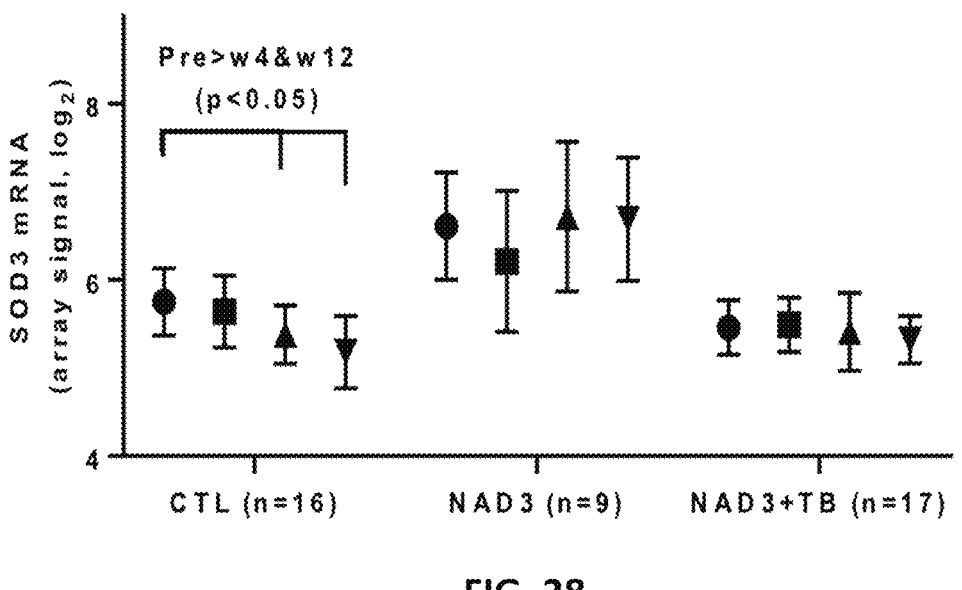

FIG. 28 depicts exemplary results for SOD3 mRNA expression in subjects with NAD3 supplementation, with NAD3-TB supplementation, or without either supplementation, after 1 week, 4 weeks, and 12 weeks.

Figure 29:
Figure 29:
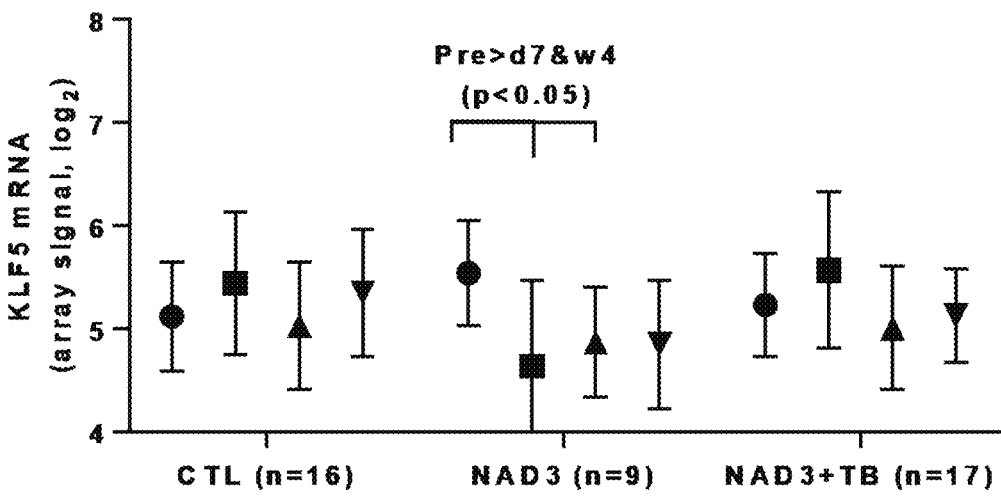

FIG. 29 depicts exemplary results for KLF5 mRNA expression in subjects with NAD3 supplementation, with NAD3-TB supplementation, or without either supplementation, after 1 week, 4 weeks, and 12 weeks.

Figure 30:
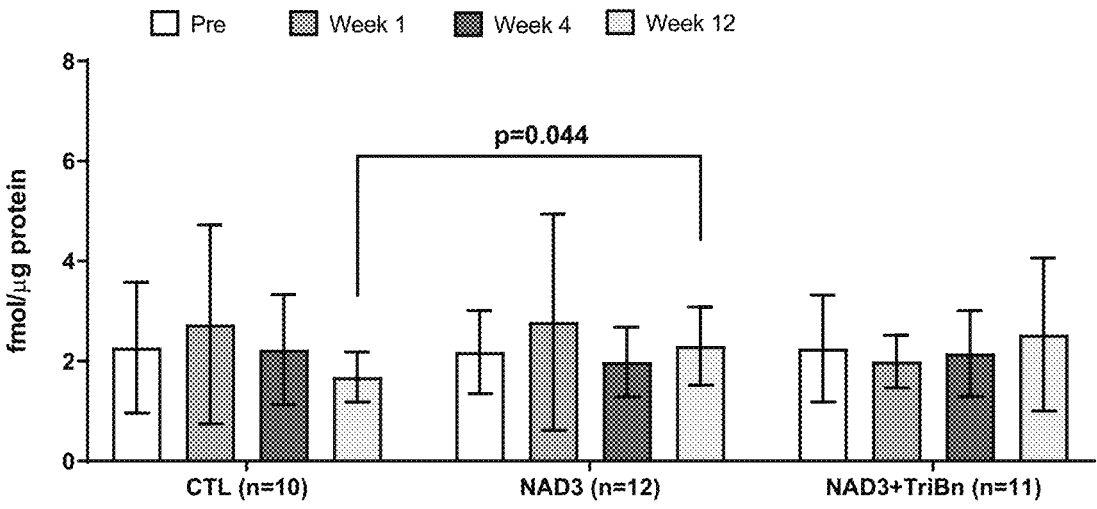

FIG. 30 depicts exemplary results for PBMC NAD+ concentrations in subjects with NAD3 supplementation, with NAD3-TB supplementation, or without either supplementation, after 1 week, 4 weeks, and 12 weeks.

Figure 31:
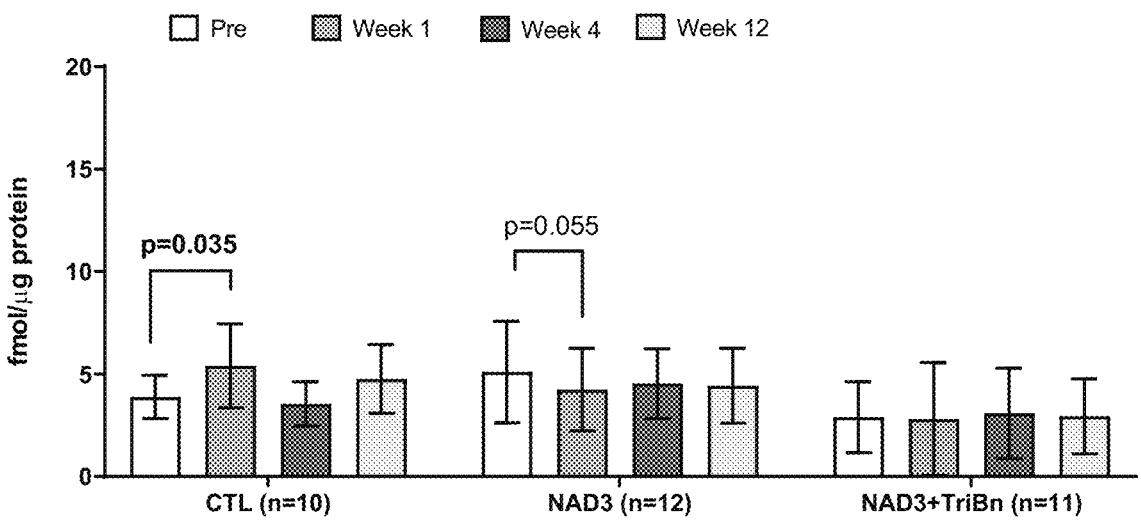

FIG. 31 depicts exemplary results for PBMC NADP+ concentrations in subjects with NAD3 supplementation, with NAD3-TB supplementation, or without either supplementation, after 1 week, 4 weeks, and 12 weeks.

Figure 32:
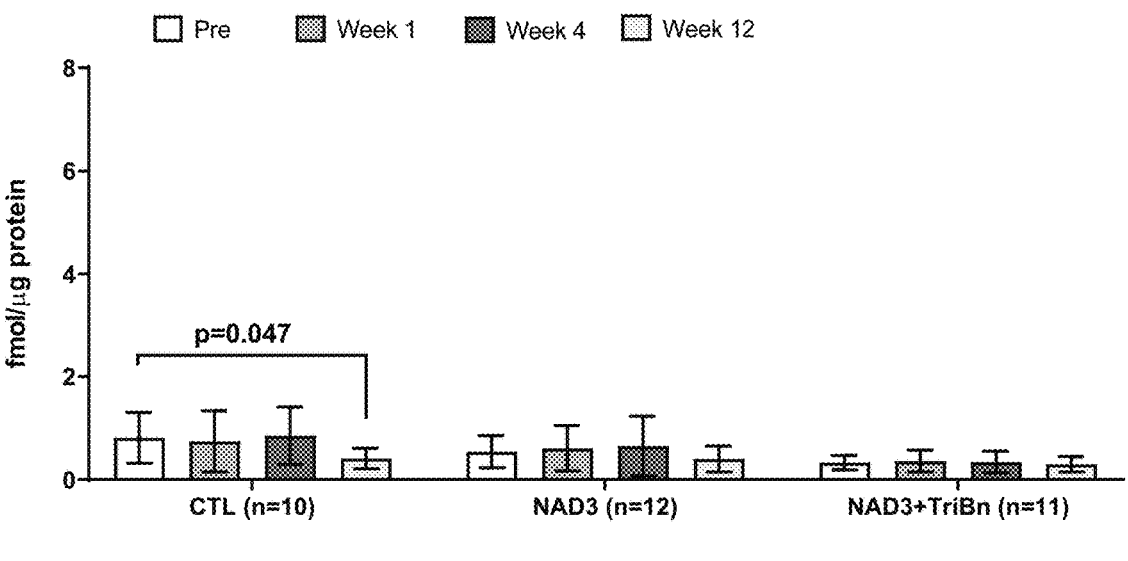

FIG. 32 depicts exemplary results for PBMC NADH concentrations in subjects with NAD3 supplementation, with NAD3-TB supplementation, or without either supplementation, after 1 week, 4 weeks, and 12 weeks.

Figure 33:
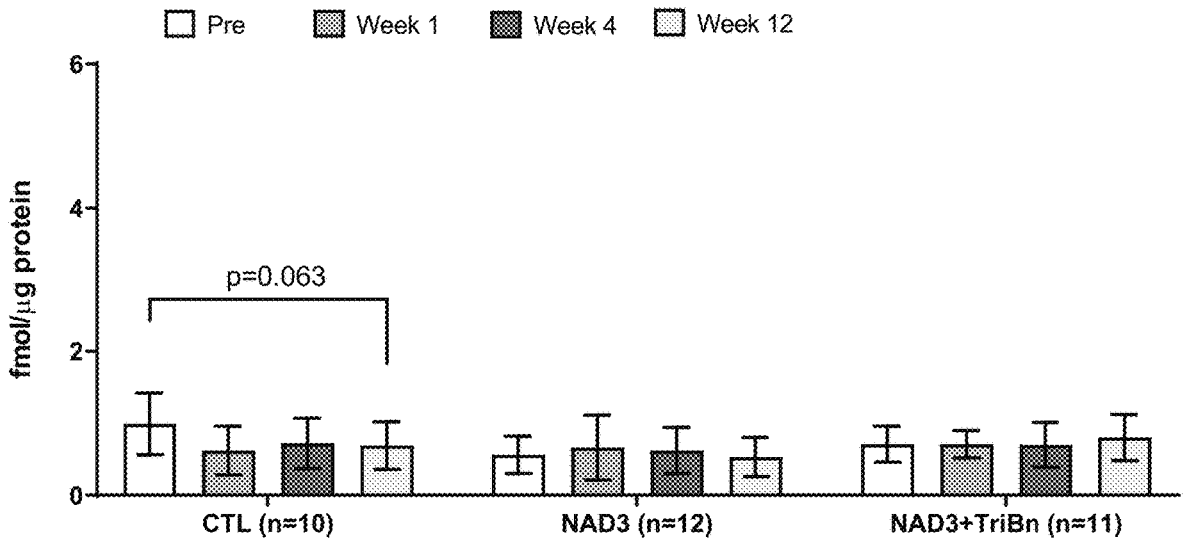

FIG. 33 depicts exemplary results for PBMC NADPH concentrations in subjects with NAD3 supplementation, with NAD3-TB supplementation, or without either supplementation, after 1 week, 4 weeks, and 12 weeks.

Figure 34:
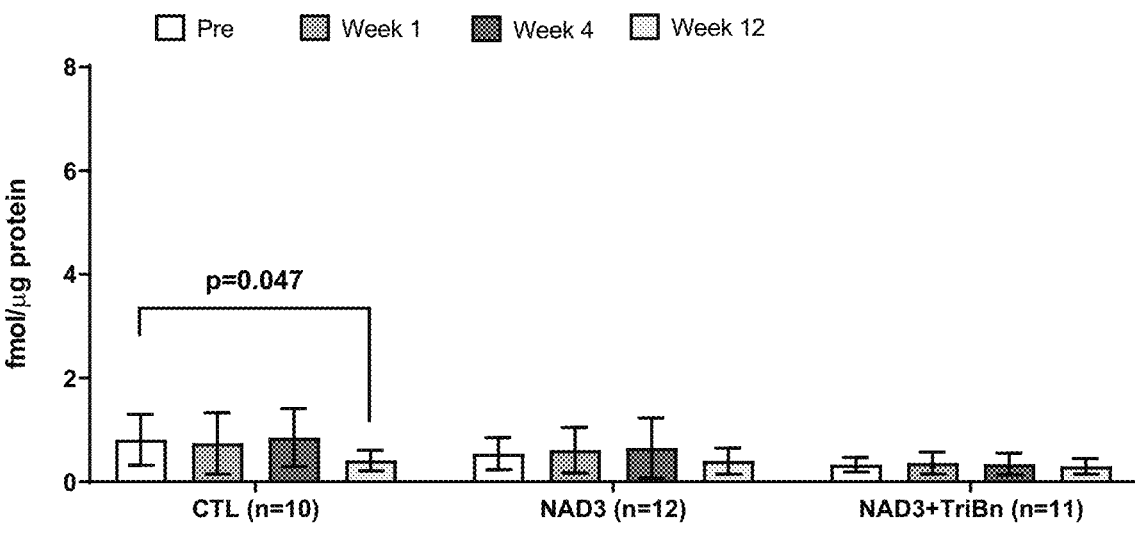

FIG. 34 depicts exemplary results for PBMC NAAD concentrations in subjects with NAD3 supplementation, with NAD3-TB supplementation, or without either supplementation, after 1 week, 4 weeks, and 12 weeks.

Figure 35:
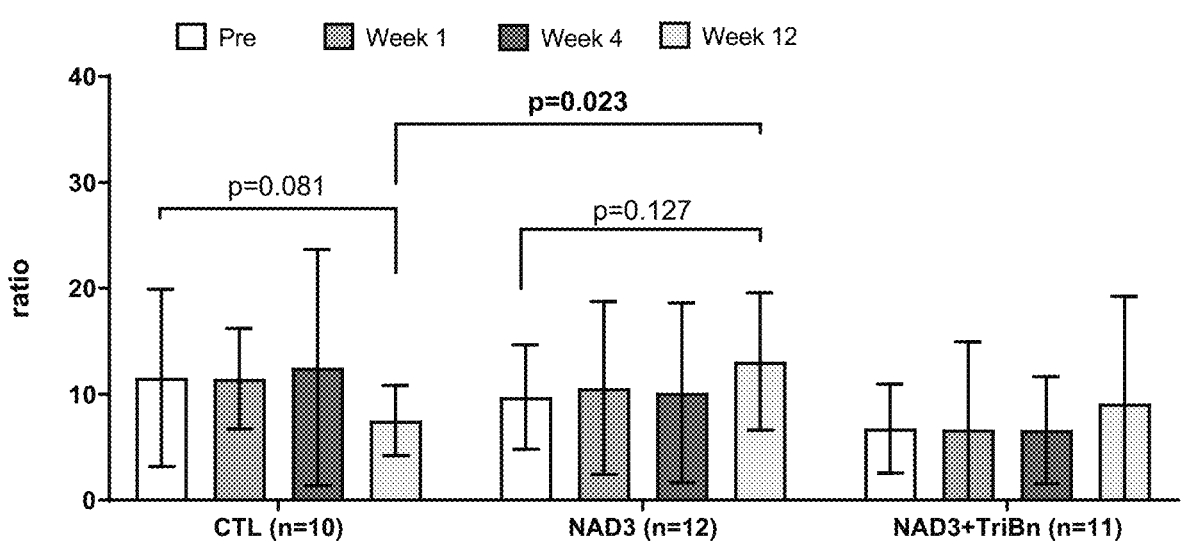

FIG. 35 depicts exemplary results for PBMC NAD+/ NADH ratios in subjects with NAD3 supplementation, with NAD3-TB supplementation, or without either supplementation, after 1 week, 4 weeks, and 12 weeks.

DETAILED DESCRIPTION

The inventors have now discovered that nutraceutical compositions can be prepared that have significant impact on cellular ageing, cellular stress resilience, longevity, and pathways and pathway elements associated therewith. In especially preferred aspects, contemplated compositions will include a cytoprotective formulation that comprises a combination of (a) a purine alkaloid, (b) an isothiocyanate or thioglucoside, and (c) a metal-containing antioxidant, where such ingredients can be isolated and/or purified (e.g., having chemical purity of at least 90 mol %) or where such ingredients can be present or be provided in form of an extract or other preparation from a plant, yeast, or animal.

For example, in some preferred embodiments, the purine alkaloid is present in and provided as a Camilla sp., *Theobroma* sp., or *Coffea* sp. extract, or extract from the Cupuacu plant, or seeds of *Herrania* species, while in other preferred embodiments the purine alkaloid is theacrine, theobromine, theophylline, or caffeine. Likewise, in some preferred embodiments the isothiocyanate or thioglucoside is present in and provided as a *Brassica* sp. extract (e.g., wasabi extract), while in other preferred embodiments the isothiocyanate or thioglucoside is allyl isothiocyanate or 2-phenylethyl isothiocyanate. Furthermore, in some preferred embodiments, the metal-containing antioxidant comprises copper (or other transition metal) or zinc as a ligand to an organic moiety, while in further preferred embodiments the metal-containing antioxidant is a copper-(I)-nicotinate complex (of course, in alternative embodiments copper-II-complexes or chelates with orotate, amino acids, etc. and even colloidal copper are also deemed appropriate).

Thus, and as is described in more detail below, one exemplary composition for reducing cellular ageing, improving cellular stress resilience, and/or increasing longevity will include a cytoprotective formulation comprising a combination of (a) theacrine, (b) a wasabi extract as source of an isothiocyanate or thioglucoside, and (c) a copper-(I)-nicotinate complex as antioxidant. Where theacrine is used, various sources may be employed. However, a particularly preferred form of theacrine is TeaCrine™ (generic name theacrine, commercially available). As noted herein, all ingredients can be synthetic, nature-identical, or of natural origin in crude, partially processed, refined, or purified form. For example, purine alkaloids may be synthesized from a precursor, or isolated from a plant part such as a tea leaf, coffee bean and/or coffee fruit. Likewise, the isothiocyanate or thioglucoside may be fully synthetic, or isolated from various plant materials. Moreover, it should be noted that all ingredients may be disposed in a nutritionally acceptable matrix (e.g., within original plant material, fermented material that may or may not include a microorganism) or otherwise suitable carrier. Therefore, contemplated ingredients may be or be derived from natural materials and extracts, recombinant DNA technology, microbial fermentation, total organic synthesis, and any reasonable combination thereof.

Based on experimental findings and data as presented in more detail below, the components of the cytoprotective formulation are deemed to have multiple desirable and pleiotropic effects that address multiple biological systems. Particularly, contemplated compositions and methods are thought to support and improve mitochondrial function and integrity (e.g., via SIRT1, SIRT4, global SIRT1-7 activity, PGC-1α, TOMM40 upregulation), provide anti-inflammatory effects and immunomodulation (e.g., by NLRP3/inflammasome downregulation), stimulate longevity gene expression/activity (e.g., by upregulation of SIRT proteins), optimize NAD metabolic pathways to increase energy metabolism (e.g., via upregulation of PGC-1α), improve DNA repair processes (e.g., via SIRT1 and SIRT6 upregulation), and/or increase telomere stability/length (e.g., via SIRT1 and SIRT6 upregulation).

More particularly, contemplated compositions and methods will advantageously affect one or more physiological markers that are associated with pathways regulating mitochondrial integrity and function, inflammation and cellular stress response, energy metabolism, and especially fatty acid oxidation, longevity, DNA repair, and/or telomere maintenance/lengthening. For example, and as described in more detail below, contemplated compositions are advantageously capable to modulate various stress response mechanisms and pathways that control cytointegrity. Among other pathways, contemplated compositions may affect stress response proteins such as Hsp70, Hsp16, Hsp90, and/or SOD3 as well as Wnt/beta-catenin or Lin-44/Wnt signaling pathways, ageing related pathways that include ELT-3 transcription factors, or may downregulate pathways that include Mom-2/Wnt or Cwn-2/Wnt signaling. Therefore, and viewed from a system perspective, contemplated compositions will beneficially regulate autophagy and/or mitophagy, increase stress resistance and stress response, help maintain DNA integrity and repair, and promote telomere integrity, all of which are deemed hallmarks of longevity. Moreover, due to the pleiotropic nature of the compositions presented herein, signaling pathways are affected that interact with one another and so provide a multimechanistic cytoprotective effect that drives cellular metabolism and repair and stress response towards a profile associated with health and longevity. Such effects are believed to operate on a cellular level, tissue level, and even systemic level.

In a first embodiment, the marker is SIRT1, which is a NAD-dependent protein deacetylase that links transcriptional regulation directly to intracellular energetics and is also known to participate in the coordination of several separated cellular functions, including cell cycle, response to DNA damage, metabolism, apoptosis, and autophagy. Moreover, SIRT1 can modulate chromatin function through deacetylation of histones and can thereby promote alterations in the methylation of histones and DNA, leading to transcriptional repression of genes affected by methylation or other epigenetic changes. In addition, SIRT1 is known to deacetylate a broad range of transcription factors and coregulators, thereby regulating target gene expression positively and negatively. For example, SIRT1 was shown to de-acetylate and affect the activity of both members of the PGC1-alpha/ERR-alpha complex, which are essential metabolic regulatory transcription factors.

With regard to SIRT1 function on energy metabolism it should be appreciated that SIRT1 serves as a sensor of the cytosolic ratio of NAD(+)/NADH, which is altered by glucose deprivation and metabolic changes associated with caloric restriction. Moreover, SIRT1 is also a component of the eNoSC (energy-dependent nucleolar silencing complex), a complex that mediates silencing of rDNA in response to intracellular energy status and acts by recruiting histone-modifying enzymes. The eNoSC complex is able to sense the energy status of cell: upon glucose starvation, elevation of NAD(+)/NADP(+) ratio activates SIRT1

With regard to DNA repair it was proposed that SIRT1 also contributes to genomic integrity via positive regulation of telomere length, and that SIRT1 is involved in DNA damage response by repressing genes which are involved in DNA repair, such as XPC and TP73, deacetylating XRCC6/Ku70, and facilitating recruitment of additional factors to sites of damaged DNA. For example, SIRT1-deacetylated NBN can recruit ATM to initiate DNA repair and SIRT1-deacetylated XPA can interacts with RPA2. Moreover, SIRT1 also deacetylates WRN, thereby regulating its helicase and exonuclease activities and regulates WRN nuclear translocation in response to DNA damage. Additionally, SIRT1 deacetylates APEX1 and stimulates cellular AP (apurinic site) endonuclease activity by promoting the association of APEX1 to XRCC1. Finally, SIRT1 is also thought to deacetylate XRCC6/Ku70 at Lys-539 and Lys-542 causing it to sequester BAX away from mitochondria thereby inhibiting stress-induced apoptosis.

In a second embodiment, the marker is SIRT4, which is typically located in the cytoplasm, mitochondria, and nucleus of a cell and which is ubiquitously expressed. SIRT4 is thought to have multiple catalytic functions and was reported to operate as an NAD-dependent protein lipoamidase, an ADP-ribosyl transferase, and a deacetylase. In most cases, SIRT4 catalyzes more efficiently removal of lipoyl- and biotinyl-than acetyl-lysine modifications. As a consequence, the pyruvate dehydrogenase complex (PDH) activity can be inhibited via the enzymatic hydrolysis of the lipoamide cofactor from the E2 component, DLAT, in a phosphorylation-independent manner. SIRT4 also catalyzes the transfer of ADP-ribosyl groups onto target proteins, including mitochondrial GLUD1 (glutamate dehydrogenase 1), inhibiting GLUD1 enzyme activity. As such, SIRT4 can act as a negative regulator of mitochondrial glutamine metabolism by mediating mono ADP-ribosylation of GLUD1: expressed in response to DNA damage and negatively regulates anaplerosis by inhibiting GLUD1, leading to block metabolism of glutamine into tricarboxylic acid cycle and promoting cell cycle arrest. In response to mTORC1 signal, SIRT4 expression is repressed, promoting anaplerosis and cell proliferation. Moreover, SIRT4 also acts as a NAD-dependent protein deacetylase, mediating deacetylation of Lys-471 of MLYCD, inhibiting its activity, thereby acting as a regulator of lipid homeostasis. Finally, SIRT4 was also reported to control fatty acid oxidation by inhibiting PPARA transcriptional activation.

In a third embodiment, the marker is SIRT6. As the name implies, SIRT6 is a member of the sirtuin family of NAD-dependent enzymes that are implicated in cellular stress resistance, genomic stability, aging and energy homeostasis. SIRT6 is localized to the nucleus, exhibits ADP-ribosyl transferase and histone deacetylase activities, and plays a role in DNA repair, maintenance of telomeric chromatin, inflammation, lipid and glucose metabolism. Moreover, SIRT6 was also reported as a stress responsive protein deacetylase and as a mono-ADP ribosyltransferase.

With regard to DNA repair, SIRT6 was reported as a chromatin-associated protein that is required for normal base excision repair of DNA damage in mammalian cells. Moreover, SIRT6 has deacetylase activity towards histone H3K9Ac and H3K56Ac and modulates acetylation of histone H3 in telomeric chromatin during the S-phase of the cell cycle. Notably, SIRT6 was also reported to deacetylate histone H3K9Ac at NF-kappa-B target promoters and may therefore downregulate the expression of a subset of NF-kappa-B target genes. Additionally, SIRT6 may also act as a corepressor of the transcription factor HIF1A to so control expression of multiple glycolytic genes to regulate glucose homeostasis, which has substantial impact on energy metabolism.

Therefore, on a functional level, SIRT6 can be viewed as a required factor for genomic stability, as a regulator for the production TNF, and as a modulator of cellular senescence and apoptosis.

In a fourth embodiment, the marker is NRF2 (nuclear factor (erythroid-derived 2)-like 2), that is known to regulate the expression of various antioxidant proteins that protect against oxidative damage triggered by injury and inflammation. As such the systemic and local function of NRF2 is substantial in cytoprotection against oxidative stress and inflammatory mediator signals and inflammation. Mechanistically, NRF2 acts as a transcription activator that binds to antioxidant response (ARE) elements in the promoter regions of target genes with such elements. Consequently, NRF2 is a critical mediator for coordinated up-regulation of genes required for response to oxidative stress.

In a fifth embodiment, the marker is p27 (cyclin-dependent kinase inhibitor 1B) that acts as a regulator of cell cycle progression. More specifically p27 is thought to inhibit the kinase activity of CDK2 bound to cyclin A, but thought to have little inhibitory activity on CDK2 bound to SPDYA. P27 is also a potent inhibitor of cyclin E- and cyclin A-CDK2 complexes, forms a complex with cyclin type D-CDK4 complexes, and is involved in the assembly, stability, and modulation of CCND1-CDK4 complex activation. Notably, p27 can act either as an inhibitor or an activator of cyclin type D-CDK4 complexes, depending on its phosphorylation state and/or stoichiometry. On a functional level, p27 is considered a tumor suppressor because of its function as a regulator of the cell cycle, and as such helps maintain cellular homeostasis and integrity.

In a sixth embodiment, the marker is CDKN2B/p15. This protein acts as a cyclin-dependent kinase 4 inhibitor B (cyclin-dependent kinase inhibitor), which forms a complex with CDK4 or CDK6, and so prevents the activation of the CDK kinases. Consequently, and on a functional level, CDKN2B functions as a cell growth regulator that controls cell cycle G1 progression, and as such helps maintain cellular homeostasis and integrity.

In a seventh embodiment, the marker is ATG12 (also known as autophagy-related protein 12). ATG12 is a ubiquitin-like protein that is involved in autophagy vesicle formation. Autophagy is a process of bulk protein degradation in which cytoplasmic components, including organelles, are enclosed in double-membrane structures called autophagosomes and delivered to lysosomes or vacuoles for degradation. Conjugation with ATG5 through a ubiquitin-like conjugating system involving also ATG7 as an E1-like activating enzyme (ATG10 as an E2-like conjugating enzyme is essential for its function). The ATG12-ATG5 conjugate acts as an E3-like enzyme which is required for lipidation of ATG8 family proteins and their association to the vesicle membranes. Thus, ATG12 is involved in cell maintenance, support of cellular integrity, and protein turnover. Moreover, ATG12 conjugation to ATG3 is also reported to help regulate mitochondrial homeostasis (possibly through interaction with Bcl-2) and cell death. In that context, further suitable markers include those related to regulation of mitophagy/autophagy, and especially transcription factors, co-activators, and regulatory proteins such as HMGB1, BNIP3, NIX, ACAA2, GABARAPL1, etc.

In an eighth embodiment, the marker is LCB3 (SPTLC3): LCB3 is a serine palmitoyltransferase, and the heterodimer formed with LCB1/SPTLC1 constitutes the catalytic core. The composition of the serine palmitoyltransferase (SPT) complex determines the substrate preference. The SPTLC1-SPTLC3-SPTSSA isozyme uses both C14-CoA and C16-CoA as substrates, while the SPTLC1-SPTLC3-SPTSSB has the ability to use a broader range of acyl-CoAs without apparent preference. As such, LCB3 is an important regulator in sphingolipid metabolism. Notably, sphingolipid metabolites, such as ceramide and sphingosine-1-phosphate, have been shown to be important mediators in the signaling cascades involved in apoptosis, proliferation, stress responses, necrosis, inflammation, autophagy, senescence, and differentiation. Consequently, LCB3 is a substantial factor in pathways regulating stress response, autophagy, and senescence. With reference to FIG. 6A, increased autophagy was observed in cells incubated with beta hydroxybutyrate (BHB), cannabidiol (CBD), or selenium.

In a ninth embodiment, the marker is NLRP3 (cryoporin). NLRP is traditionally viewed as a PRP (pathogen recognition receptor) and is predominantly expressed in macrophages. Moreover, NLRP3 is also a component of the inflammasome, and detects products of damaged cells such as extracellular ATP. As the sensor component of the NLRP3 inflammasome, NLRP3 plays a critical role in innate immunity and inflammation. In response to pathogens and other damage-associated signals, NLRP3 initiates the formation of the inflammasome polymeric complex, made of NLRP3, PYCARD and CASP1 (and possibly CASP4 and CASP5). Recruitment of proCASP1 to the inflammasome promotes its activation and CASP1-catalyzed IL1B and IL18 maturation and secretion in the extracellular milieu. Inflammasomes can also induce pyroptosis, an inflammatory form of programmed cell death. Under resting conditions, NLRP3 is autoinhibited. NLRP3 activation stimuli include extracellular ATP, reactive oxygen species, K(+) efflux, crystals of monosodium urate or cholesterol, amyloid-beta fibers, environmental or industrial particles and nanoparticles, cytosolic dsRNA, etc. Independently of inflammasome activation, regulates the differentiation of T helper 2 (Th2) cells and has a role in Th2 cell-dependent asthma and tumor growth. Consequently, NLRP3 is an important player in stress response of a cell to cell damage and oxidative stress.

In a tenth embodiment, the marker is PGC-1α (peroxisome proliferator-activated receptor gamma coactivator 1-alpha). PGC-1α operates as a transcriptional coactivator for steroid receptors and nuclear receptors and as such increases the transcriptional activity of PPARG and thyroid hormone receptor on the uncoupling protein promoter. Moreover, PGC-1α can regulate key mitochondrial genes that contribute to the program of adaptive thermogenesis and further plays an essential role in metabolic reprogramming in response to dietary availability through coordination of the expression of a wide array of genes involved in glucose and fatty acid metabolism. Therefore, PGC-1α is a significant marker for regulation of genes involved in energy metabolism (and may be viewed as master regulator of mitochondrial biogenesis). Notably, PGC-1α is also thought to be involved in the integration of the circadian rhythms, and with that in energy metabolism (as PGC-1α is required for oscillatory expression of clock genes, such as ARNTL/BMAL1 and NR1D1).

In an eleventh embodiment, the marker is TOMM40 (translocase of outer mitochondrial membrane 40 homolog (yeast)). TOMM40 is a protein that is localized in the outer membrane of the mitochondria and is the channel-forming subunit of the translocase of the mitochondrial outer membrane (TOM) complex that is essential for import of protein precursors into mitochondria. Thus, TOMM40 may be used as a suitable marker for mitochondrial function and health.

Of course, it should be appreciated that the contemplated compositions and methods presented herein will advantageously affect not only one marker as noted above, but may modulate two, three, four, five, six, seven, eight, nine, ten, or all of the markers noted above, possibly in a synergistic manner to so exert the pleiotropic effect.

Consequently, contemplated compositions will be formulated to affect not only one marker as noted above, but may modulate two, three, four, five, six, seven, eight, nine, ten, or all of the markers noted above, possibly in a synergistic manner. Thus, multiple pathways can be addressed to achieve (preferably synergistic) effects with regard to at least one of mitochondrial integrity and function, inflammation and cellular stress response, energy metabolism, and especially fatty acid oxidation, longevity, DNA repair, and/or telomere maintenance/lengthening.

To that end the inventors contemplate that a composition will include a cytoprotective formulation that comprises a combination of (a) a purine alkaloid, (b) an isothiocyanate or thioglucoside, and (c) a metal-containing antioxidant, preferably in quantities and proportions that are effective to improve at least one of mitochondrial integrity and function, inflammation and cellular stress response, energy metabolism, and especially fatty acid oxidation, autophagy/mitophagy, regenerative stem cell potential, longevity, DNA repair, and/or telomere maintenance/lengthening.

In view of the foregoing embodiments, the inventors surprising discovered that mammals (e.g., humans) supplemented with the composition exhibit: (1) a significant increase in leukocyte telomere lengths relative to placebo supplementation over 4 weeks, (2) upregulation of TERF1 and POT1 gene expression in human white blood cells over 8 weeks and 12 weeks, respectively, (3) increased NMRK1 (NRK1) gene expression over 7 days, (4) significant upregulation of SOX2 gene expression and modulation of KLF gene expression after 12 weeks, (5) elevations of SOD3 gene expression after 12 weeks, (6) increased global (overall) SIRTUIN1-7 enzyme activity in human white blood cells after 12 weeks, (7) significant decrease in total cholesterol (e.g., 12% (23 mg/dL)) after 12 weeks, (8) significant decrease in LDL-cholesterol (e.g., 16% (20 mg/dL)) after 12 weeks, (9) significant decrease in VLDL-cholesterol (e.g., 19%) after 12 weeks, (10) significant upregulation of SIRT6 gene expression after 12 weeks, (12) significant upregulation of NMNAT1 gene expression after 12 weeks, (13) significant downregulation of NLRP3 gene expression after 4 weeks, (14) significant elevation of SOD3 gene expression after 12 weeks, (15) improved PGC1-alpha gene expression, and (16) significant reduction in body weight and blood triglycerides after 8 weeks.

For example, one exemplary composition will include theacrine (e.g., purity at least 90 mol %, and more preferably at least 95 mol %), a wasabi extract (preferably standardized to isothiocyanates) as a source of isothiocyanates or thioglucosides, and cuprous nicotinate as the a metal-containing antioxidant. In further preferred examples, the composition is formulated for oral administration (e.g., as a capsule or tablet as dosage unit) and includes theacrine in an amount of between 10-500 mg in a single dosage unit, the wasabi extract in an amount of between 50-1,000 mg in a single dosage unit, and the cuprous nicotinate in an amount of between 1 mcg-100 mg in a single dosage unit.

The inventors also contemplate a composition that includes a cytoprotective formulation comprising a combination of a purine alkaloid, an isothiocyanate or thioglucoside, a metal containing antioxidant, nicotinamide riboside alternative (NAD3), and one or more of the following: the non-metal or metalloid selenium (Se), tributyrin, beta hydroxybutyrate (BHB), beta hydroxybutyric acid, butyrate, poly hydroxybutyrate (PHB), humic shale extracts, fulvate or fulvic acid (and its derivatives such as those described in US2016/0066603 or U.S. Pat. No. 6,440,436), triproprionin, triacetin, palmitoleic acid, and/or gamma linolenic acid (GLA). The inventors have surprisingly found that the addition of tributyrin and NAD3 in the composition of a purine alkaloid, an isothiocyanate or thioglucoside, and a metal containing antioxidant gives additional beneficial effect with regards to inflammation and aging. Tributyrin helps create tighter junctions in the colon epithelium leading to less gut waste circulating in the blood and less systemic inflammation, which in turn leads to reduced aging. The inventors surprisingly found that this particular composition has a synergistic effect and is ideal for the gut-brain-heart vagus nerve trifecta as Cu(I) improves heart health and theacrine acts on the brain cells to improve mood, energy, and focus.

As shown in exemplary results in the present disclosure (e.g., FIGS. and Tables)—notably, increased levels of NAMPT protein and decreased induction of NLRP3, the presently disclosed methods and compositions support nicotinamide adenine dinucleotide (NAD+) enzyme activity. Accordingly, contemplated methods and compositions for reducing cellular ageing, improving cellular stress resilience, and/or increasing longevity include the disclosed cytoprotective composition having a cytoprotective formulation including a combination of (a) a purine alkaloid, (b) an isothiocyanate or thioglucoside, (c) a metal-containing antioxidant, and optionally (d) one or more additional ingredients including selenium, a polyphenol, tributyrin, and/or BHB. In addition to methods and compositions which increase NAD+, the inventive subject matter also includes decreasing NAD+ degradation. Typically, cytoprotective methods and compositions inhibit NAD+ degradation by inhibiting CD38 and/or CD157 activity. See, e.g., Wang et al., 2019, *Front Physiol.*, 10:1-10 and Ruan et al., 2018, *Pharmacol Res.* 128:345-358.

In addition to tributyrin, butyrate, BHB, and PHB, other fatty acids are contemplated to be present in the composition as well. Examples of such fatty acids are triproprionin and triacetin. Furthermore, a short chain fatty acid such as palmitoleic acid or gamma linolenic acid (GLA), may improve skin conditions such as eczema, atopic dermatitis.

However, it should be appreciated that numerous alternative compounds may be included in the cytoprotective formulation in addition to or as an alternative to the above compounds. For example, theacrine may be replaced by (or supplemented with) one or more theacrine prodrug, a theacrine metabolite, and/or a theacrine analogs. For example such compounds include liberine or methylliberine, caffeine, methylated or acetylated theacrine, etc. Likewise, the wasabi extract may be replaced or supplemented with various alternative extracts or preparations (e.g., dried, powderized, etc.) of portions of a plant or sprout belonging to the family Brassicaceae (such as *Armoracia rusticana*). Other suitable plant preparations include *Aronia*, which may be in form of expressed juice (which may be further processed), a dried powder, or in form of an extract. Alternatively, or additionally, the isothiocyanate or thioglucoside may also be a chemically isolated or synthetic isothiocyanate or thioglucoside. For example, suitable isothiocyanates especially include allyl isothiocyanate and or 2-phenylethyl isothiocyanate. Of course, it should be appreciated that suitable compounds may also be present as precursors, most typically those cleavable by myrosinase such as various thioglucosides (esp. gluosinolates). Likewise, the metal-containing antioxidant need not be limited to a copper-(I)-nicotinate complex, but all nutritionally acceptable forms of copper such as copper-I/II-complexes and chelates (e.g., defined complexes with orotate, amino acids, etc., or undefined as in a complex food matrix (e.g., U.S. Pat. No. 8,642,651)) are also expressly contemplated. Moreover, various other antioxidants containing a (transition) metal portion are deemed suitable for use herein (see e.g., Curr Top Med Chem. 2011; 11(21):2703-13). Especially suitable metal antioxidants will not only provide antioxidant capacity but also deliver desirable quantities of the metal to the mitochondria in a cell and/or to various enzymes (such as SIRT) as a co-factor. Thus, contemplated (transition) metals especially include copper, zinc, iron, and manganese. In this context, it should be noted that copper, zinc, manganese, and other metals may be co-administered (or even replace cuprous nicotinate), and administration of such metals will typically follow known dosages and quantities.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.).

In typical embodiments, a cytoprotective composition for oral or topical administration is disclosed herein wherein the composition includes a cytoprotective formulation comprising a combination of (a) a purine alkaloid, (b) an isothiocyanate or thioglucoside, (c) a metal-containing antioxidant, and optionally (d) one or more additional ingredients including selenium, a polyphenol, tributyrin, and/or BHB.

For topical administration, the inventive subject matter includes topical (e.g., nutracosmeceutical) cytoprotective compositions. In general, compositions for topical and oral administration are understood by those skilled in the art. For example, NAD3 enhancement compositions for skin and skin cancer therapy as well as topical therapies for inflammasome activation are known in the art. See, e.g., Garcia-Peterson et al., 2017, *Skin Pharmacol Physiol.*, 30:216-224 and Rong-Jane Chen et al., 2016, *Int. J. Mol. Sci*, 17:1-16.

Most typically, contemplated compositions will deliver between 10-500 mg, or between 10-800 mg, or between 20-1,000 mg, or between 30-1,200 mg, or between 50-1,500 mg, or between 100-2,000 or even more of the cytoprotective formulation in a single dosage unit. Viewed from a different perspective, at least 20 wt %, or at least 30 wt %, or at least 40 wt %, or at least 50 wt %, or at least 60 wt %, or at least 70 wt %, or at least 80 wt %, or at least 90 wt % of the composition will be the cytoprotective formulation. Consequently, preferred oral single dosage units (or recommended daily uptake) will be between 20-200 mg, or between 40-400 mg, or between 60-600 mg, or between 80-800 mg, or between 100-1,000 mg, or between 200-2,000 mg, and in some cases even higher.

Preferably, the purine alkaloid is present in an amount of between 10-400 mg, such as between 10-100 mg, or between 20-200 mg, or between 30-300 mg, or between 40-400 mg, or between 50-500 mg, or between 50-750 mg, or between 100-1,000 mg, or between 200-2,000 mg in a single dosage unit. Likewise, the isothiocyanate or thioglucoside is present in an amount of between 10-150 mg, or between 20-400 mg, or between 50-750 mg, or between 75-1,000 mg, or between 100-1,500 mg, or between 250-2,500 mg, in a single dosage unit where an extract or plant preparation is used. Where isolated isothiocyanates or thioglucosides are used, the isothiocyanate or thioglucoside is present in an amount of between 1-15 mg, or between 2-40 mg, or between 5-75 mg, or between 10-100 mg, or between 20-150 mg, or between 50-250 mg, or even higher in a single dosage unit. Depending on the type of metal-containing antioxidant, the metal-containing antioxidant may be present in an amount of between 1 mcg-1 mg, or between 10 mcg-100 mcg, or between 100 mcg to 1 mg, or between 1-20 mg, or between 5-75 mg, or between 10-100 mg, or between 20-150 mg, or between 50-250 mg, or even higher in a single dosage unit.

Moreover, it should be appreciated that contemplated oral and topical compositions may further include additional functional ingredients that may provide further enhancement of the desired effects as presented herein. For example, suitable longevity enhancing ingredients include acetoacetate, and beta-hydroxybutryate, while compounds that contribute to enhancing SIRTs and SIRT Targets include trans-resveratrol, quercetin, honokiol, oroxylin-A, EGCG, berberine, hydroxy-tyrosol (all of which cross-modulate targets that help preserve mitochondrial function, metabolic flexibility, endothelial/vascular function, while inhibiting systemic inflammation, apoptosis, and fibrosis). Additional ingredients include berberine, curcumine, various stilbenoids such as picetannol, one or more chalcones, catechins, and flavonols such as butein phytocannabinoids and NAD precursors. Moreover, suitable additional ingredients may also be added as absorption enhancers and therefore include various vanilloids, piperine, ascorbic acid, etc. Where desired, additional ingredients also include various enzymes, and particularly those that support antioxidant systems. Therefore, superoxide dismutase is contemplated as an exemplary additional ingredient.

Therefore, additional ingredients besides the compounds in the cytoprotective formulation include more bioavailability enhancers, including for example polyphenols, bioperine, piperine, black pepper, bergamottin, dihydroxybergamottin (CYP3A4 inhibitors), flavonoids (including hesperidin, naringin, tangeritin, quercetin and nobiletin both in isolation and in combination), turmeric, triterpenoids (e.g., beta-caryophyllene, d-limonene, limonol, myrcene, etc.), pterostilbenes, fisetin. Suitable analgesics and anti-inflammatory agents include ibuprofen, salicylic acid, salicin, fish oil (omega-3 fatty acids and specialized, small lipid pro-resolving derivatives), cannabidiol (CBD), tart cherry extract or concentrate, krill oil, astaxanthin, proteolytic enzymes, glucosamine sulfate, chondroitin sulfate, MSM (methylsulfonylmethane), SAMe (S-adenosylmethionine), and/or triterpenoids.

For the polyphenol, a variety of possible polyphenols are contemplated. Polyphenols include flavonoids, phenolic acids, stilbenes, and lignans. In particular aspects, proanthocyandins may be added to the tributyrin-containing composition. Proanthocyandins include procyanidins, prodelphinidins and propelargonidins which are found in many plants, most notably apples, maritime pine bark and that of most other pine species, cinnamon, *aronia* fruit, cocoa beans, grape seed, grape skin, some red wines, bilberry, cranberry, pomegranate, black currant, green tea, and black tea. Cocoa beans contain the highest concentrations, and grape seed extract is a readily available source. The amount of proanthocyandin in each single dose may be of between 50-500 mg.

Contemplated compositions may further include extracts from one or more of *Acacia catechu, Andrographis paniculata, Scutalleria baicalensis*, agmatine sulfate, Stinging Nettle, Sea Buckthorn, curcumin, *Cissus Quadrilangularis, Boswellia Serrata*, Emu Oil, *Arnica, Mangifera indica* L. (Anacardiaceae), *Lagenaria breviflora*, and/or *Zingiber officinale* (ginger and gingerols/shogaols). Such additional agents may be used in, for example, methods of augmenting and enhancing pain modulation, and/or controlling inflammatory responses. Contemplated extracts suitable for use herein may also provide antioxidant properties, and especially preferred extracts include green tea and/or black tea extracts. While not necessary, it is typically preferred that such extracts will be standardized to a specific component or component class, and particularly to theaflavins, thearubigins, monomeric or polymeric forms of catechins, etc. For example, a black tea extract may standardized to theaflavins.

Still further contemplated compositions may include one or more metabolic enhancers including hoodia *gordonii*, yohimbine, synephrine, theobromine, flavonoids, flavanone glycosides such as naringin and hesperidin, chromium (e.g., as picolinate or glycinate, or in association with a complex food matrix), tocopherols, theophylline, alpha-yohimbine, conjugated linoleic acid (CLA), octopamine, evodiamine, passion flower, red pepper, cayenne, raspberry ketone, guggul, green tea, guarana, kola nut, beta-phenethylamines, *Acacia rigidula*, and/or forskolin (*Coleus forskohlli*). Such additional ingredients may be used in, for example, methods of enhancing 1) thermogenesis/fat and carbohydrate metabolism; 2) fat loss, weight management and improving body composition (loss of body fat, while retaining or sparing lean body mass/fat free mass/muscle); and/or 3) appetite control/appetite modulation Yet further contemplated compositions may include anti-fatigue, focusing, and/or energy enhancing ingredients such as creatine, theobromine, theophylline, synephrine, yohimbine, *rhodiola*, ashwagandha, *ginseng, Ginkgo biloba*, siberian *ginseng, astragalus*, licorice, green tea, reishi, dehydroepiandrosterone (DHEA), pregnenolone, tyrosine, N-acetyl-tyrosine, glucuronolactone, taurine, choline, CDP-choline, alpha-GPC, acetyl-L-carnitine, 5-hydroxytryptophan, tryptophan, beta-phenethylamines, Sceletium *tortuosum* (Mesembrine alkaloids), *Dendrobium* sp., *Acacia rigidula*, PQQ (Pyroloquinoline quinone), Ubiquinone(ol), nicotinamide riboside, picamilon, Huperzine A (Chinese clubmoss) or *Huperzia serrata*, L-dopa, *Mucuna pruriens*, forskolin (*Coleus forskohlli*). Such additional ingredients may be used in, for example, methods for enhancing cognitive function, including focus, concentration, sustained attention, working memory, choice and non-choice reaction time, executive function, verbal and non-verbal learning, visuospatial memory and verbal fluency.

With respect to suitable formulations, it is typically preferred that the compositions according to the inventive subject matter are formulated for oral delivery, and all known formulations for oral delivery are deemed suitable for use herein. For example, oral formulations include tablets, dragees, capsules, powders, aqueous or non-aqueous solutions or suspensions, syrup, etc. Most typically, such formulations will include at least one pharmaceutically or nutraceutically acceptable carrier, and are typically prepared to allow administration of a recommended daily dosage in a single dosage unit form. Alternatively, where desired, the dosage unit may also be chosen such that multiple dosage units per day will provide the recommended daily dosage. Alternatively, contemplated compositions may also be included in already known oral formulations. Consequently, contemplated formulations include multi-vitamin preparations and all known preparations are deemed suitable for use herein.

Moreover, contemplated compositions may also be included into an edible carrier to so increase actual or perceived nutritional value of the edible carrier. Most preferably, such edible carrier is in a ready-to-consume format and may be an energy drink, a bottled water product, a carbonated drink, etc., or a snack bar, a cereal, a confectionary item, a plant fiber-containing product etc. In less preferred aspects, parenteral administration is also contemplated and preferably includes injection, transmucosal delivery, and sublingual administration.

EXAMPLES

Example Set 1: In Vitro Analysis

In a set of experiments, the inventors exposed muscle cells in various in vitro assays where the cells were treated them with a combination of theacrine (commercially available as TeaCrine™), wasabi extract, and copper(I) nicotinate as described in more detail below. All cells were exposed for 3 hr and 24 hr, and cells were analyzed for the following markers: SIRT 1, 4, and 6 as markers for global SIRT activity; TOMM4 as marker for telomere stabilizing complex gene activity; Nrf2 mRNA expression as marker for antioxidant protein status; p27 mRNA expression as marker for cell cycle and apoptosis/autophagy; citrate synthase as marker for mitochondrial volume/capacity; NLRP3 as a marker for inflammasome presence/activity; CDK2, TOMM, ATG mRNA expression as downstream markers for cell cycle, global inflammation, autophagy activation; NAD Metabolome is currently under investigation.

Exemplary Protocols for FIGS. 1A-1F, 2A-2F, 3, and 4:

Passage 6 C2C12 myoblasts, were grown in growth medium (DMEM, 10% FBS, 1% penicillin/streptomycin, and 0.1% gentamycin) on 8 six-well plates at a seeding density of 3×105 under standard culture conditions (37° C. in a 5% CO2 atmosphere). Once myoblast growth reached 80-90% confluency ~48 h after seeding, differentiation was induced by removing growth medium and replacing it with differentiation medium [DM; DMEM, 2% (vol/vol) horse serum, 1% penicillin/streptomycin, and 0.1% gentamycin]. DM was then replaced every 24 h for 7 days to allow for myotube growth.

Treatment conditions A, B, C and D was mixed into differentiation media and administered to myotubes during differentiation on day 4 for 24 hour treatments (n=6 wells per treatment or 1 plate). The following day treatment conditions A, B, C and D were also administered to myotubes for 3 hours. Hence, this resulted in transient 3-h, acute treatments as well as 24-h, longer-term treatments.

After all treatments, differentiation/treatment media was removed and cells were washed once with phosphate-buffered saline (PBS). Thereafter, PBS was siphoned off and then a subset of cells were scraped from plate and transferred into 250 μL of Trizol for RNA isolation. Following Trizol-based RNA isolation methods, total RNA concentrations were analyzed using a Nanodrop Lite spectrophotometer (Thermo Fisher Scientific), and 1 μg of cDNA were synthesized using a commercial qScript cDNA SuperMix (Quanta Biosciences, Gaithersburg, MD) per the manufacturer's recommendations. Real-time PCR was performed using gene-specific primers and SYBR green chemistry, and all PCR reactions were confirmed to produce only one melt product. Relative expression values were performed using the 2-ΔΔCT method where 2-ACT [housekeeping gene CT—gene of interest CT] and 2-AACT (or fold change)= [2-ACT value/2-ACT average of CTL treatment]. Cyclophilin (CYCLO) was used as a housekeeping gene.

After the RNA scrape described above, 250 μl of ice-cold cell lysis buffer was applied to each well [20 mM TrisHCl (pH 7.5), 150 mM NaCl, 1 mM Na-EDTA, 1 mM EGTA, 1% Triton, 20 mM sodium pyrophosphate, 25 mM sodium fluoride, 1 mM β-glycerophosphate, 1 mM Na3VO4, and 1 μg/ml leupeptin; Cell Signaling; Danvers, MA]. Plates were then scraped and supernatant was removed. Cells were homogenized via micropestles and homogenates were centrifuged at 500 g for 5 min. After centrifugation, insoluble proteins were removed and supernatants containing solubilized cell material were stored at −80° C. This procedure was used in order to perform metabolomics profiling, identify global SIRT activity and quantify citrate synthase activity.

Treatments were grouped in four groups (A-D) and the results are shown in FIGS. 1a-1f. More specifically, Group A is one exemplary combination of TeaCrine™ (Theacrine), a wasabi extract (extract from *Wasabia japonica* standardized for isothiocynates), and cuprous niacin. Group B is as Group A, but the wasabi extract was replaced with quercetin dihydrate. Group C is nicotinamide riboside (as comparator) at a concentration and active dose 60% ABOVE group A to help demonstrate not just additive, but synergistic benefits as well results above and beyond the main comparator. Group D is silica as negative control with only excipients.

Exemplary Protocols for FIGS. 5A-5B, 6A-6C, and 7A-7C:

Treatments and cells. 6-hour and 24-hour cell culture treatments were with one of the following compounds: 1. Control or "vehicle" (DMSO+phosphate-buffered saline only); 2. Niagen (5 μg/mL); 3. BHB (beta hydroxybutyrate) (30 ug/mL); 4. CBD (cannabidiol) (5 ug/mL); 5. Olive leaf (5 ug/mL); 6. Dynamine (1 ug/mL); 7. Selenium (2 ug/mL); 8. Tributyrin (5 ug/mL)

Treatment materials and methods. C2C12 cells were treated with compounds 1-8 as listed above for 6 hours without hydrogen peroxide (H2O2) (termed "unperturbed cells" throughout); or cells were treated with compounds 1-8 above for 24 hours with a concomitant 400 uM hydrogen peroxide (H2O2).

The C2C12 line resembles mature muscle cells given that they are multinucleated and are past the rapid growth/proliferation phase.

Molecular markers and assays.

Autophagy flux (or activity) was assessed by assaying the LC3II/I ratio. This assay has been deemed the "gold standard" in autophagy monitoring (see e.g., *Autophagy,* 2007 Nov.-Dec.; 3(6):542-5).

Total antioxidant capacity was assessed using a Trolox equivalent antioxidant capacity (TEAC) assay.

DNA damage was assessed using a phosphorylation assay for H2AX. This assay has been deemed as a commonly assayed biomarker where increases in this marker have been related to increased DNA damage (see e.g., *Methods Mol Biol.* 2012; 920:613-26).

Oxidative stress was assessed using the 4HNE assay which is a product of cellular lipid oxidation (see e.g., *Am J Physiol Cell Physiol.* 2016 Oct. 1; 311(4): C537-0543).

Cell viability was assayed measuring DNA content per well where lower values indicate more cell death and decreased cell viability.

Mitochondrial biogenesis was assessed by assaying PGC-1α protein levels; PGC-1α is a master regulator of mito-chondrial biogenesis (see e.g., *Am J Clin Nutr.* 2011 April; 93(4): 884S-890S).

NAMPT protein levels were assessed to examine a key endogenous regulator of the NAD salvage pathway.

Exemplary Protocols for FIGS. 8A-8B, 9A-9C, and 10A-10D:

Treatments and cells. 6-hour and 24-hour cell culture treatments were with one of the following compounds: 1. Control or "vehicle" (DMSO+phosphate-buffered saline only); 2. NAD3 (5 μg/mL); 3. NAD3 (5 μg/mL) and CBD (cannabidiol) (1.25 ug/mL); 4. NAD3 (5 μg/mL) and Olive leaf (2.5 ug/mL); 5. NAD3 (5 μg/mL) and BHB (beta hydroxybutyrate) (30 ug/mL); 6. NAD3 (5 μg/mL) and Dynamine (1 ug/mL); 7. NAD3 (5 μg/mL) and Selenium (2 ug/mL); 8. NAD3 (5 μg/mL) and Grape Seed Extract (5 ug/mL).

Treatment materials and methods. EOMA (endothelial) cells were treated with compounds 1-8 as listed above for 6 hours without hydrogen peroxide (H2O2) (termed "unper-turbed cells" throughout); or cells were treated with com-pounds 1-8 above for 24 hours with a concomitant 200 uM hydrogen peroxide (H2O2).

The EOMA line resembles vascular endothelial cells.

Molecular markers and assays.

Autophagy flux (or activity) was assessed in EOMA cells by assaying the LC3II/I ratio. This assay has been deemed the "gold standard" in autophagy monitoring (see e.g., *Autophagy,* 2007 Nov.-Dec.; 3(6):542-5).

Total antioxidant capacity was assessed in the EOMA cells using a Trolox equivalent antioxidant capacity (TEAC) assay.

DNA damage was assessed using a phosphorylation assay for H2AX. This assay has been deemed as a commonly assayed biomarker where increases in this marker have been related to increased DNA damage (see e.g., *Methods Mol Biol.* 2012; 920:613-26).

Oxidative stress was assessed using the 4HNE assay which is a product of cellular lipid oxidation (see e.g., *Am J Physiol Cell Physiol.* 2016 Oct. 1; 311(4): C537-0543).

Cell viability was assayed measuring DNA content per well where lower values indicate more cell death and decreased cell viability.

Mitochondrial biogenesis was assessed by assaying PGC-1α protein levels; PGC-1α is a master regulator of mito-chondrial biogenesis (see e.g., *Am J Clin Nutr.* 2011 April; 93(4): 884S-890S).

NAMPT and NLRP3 protein levels were assessed in the EOMA cells to examine a key endogenous regulator of the NAD salvage pathway.

All conditions were statistically compared back to the control condition.

Western blot analysis was performed using antibodies that detected p-H2AX protein, LC3I, LC3II, 4HNE, and NLRP3 proteins in both the C2C12 and EOMA cells. Ponceau stain was used for protein staining.

Exemplary Results

FIGS. 1A-1F depict exemplary results for mRNA data of SIRT6, SIRT1, NRF2, p27, CDKN2B, ATG12, LCB3, NLRP3, PGC1α, Tomm40, and SIRT4, as indicated, for 3-hour (hr) treatments with Group A, B, C, or D treatments as indicated and as described herein. One-way analysis of variances (ANOVAs) were performed to determine if the treatments significantly differed, and least significant differ-ence (LSD) post hoc tests were performed in order to determine where the significance occurred. Treatments with different superscript letters (a, b, c, or d) indicate treatments differed from each other.

FIGS. 2A-2F depict exemplary results for mRNA data SIRT6, SIRT1, NRF2, p2'7, CDKN2B, ATG12, LCB3, NLRP3, PGC1α, Tomm40, and SIRT4, as indicated, for 24-hr treatments with Group A, B, C, or D treatments as indicated and as described herein. One-way ANOVAs were performed to determine if treatments significantly differed, and LSD post hoc tests were performed in order to determine where the significance occurred. Treatments with different superscript letters (a, b, c, or d) indicate treatments differed from each other.

Figure 1A:
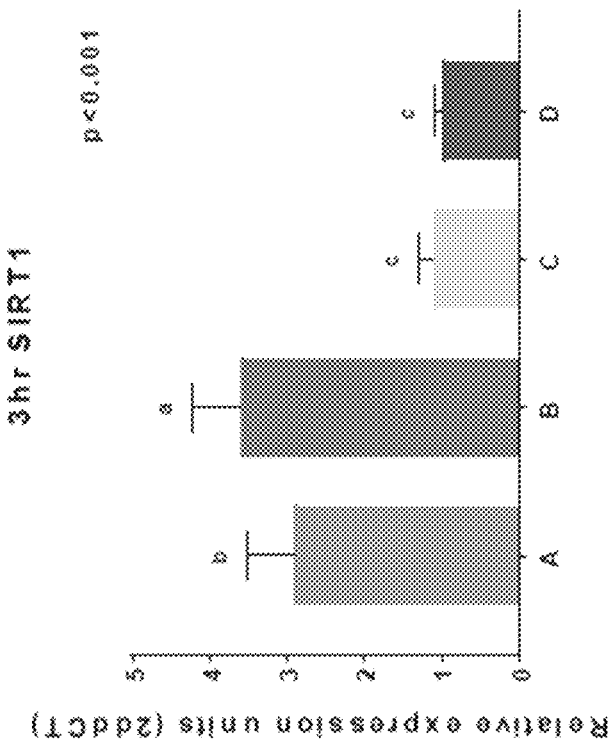
FIGS. 1A-1F depict exemplary results for mRNA data of SIRT6, SIRT1, NRF2, p27, CDKN2B, ATG12, LCB3, NLRP3, PGC1α, Tomm40, and SIRT4, as indicated, for 3-hour (hr) treatments with Group A, B, C, or D treatments as indicated and as described herein. One-way analysis of variances (ANOVAs) were performed to determine if the treatments significantly differed, and least significant difference (LSD) post hoc tests were performed in order to determine where the significance occurred. Treatments with different superscript letters (a, b, c, or d) indicate treatments differed from each other.
Figure 1A:
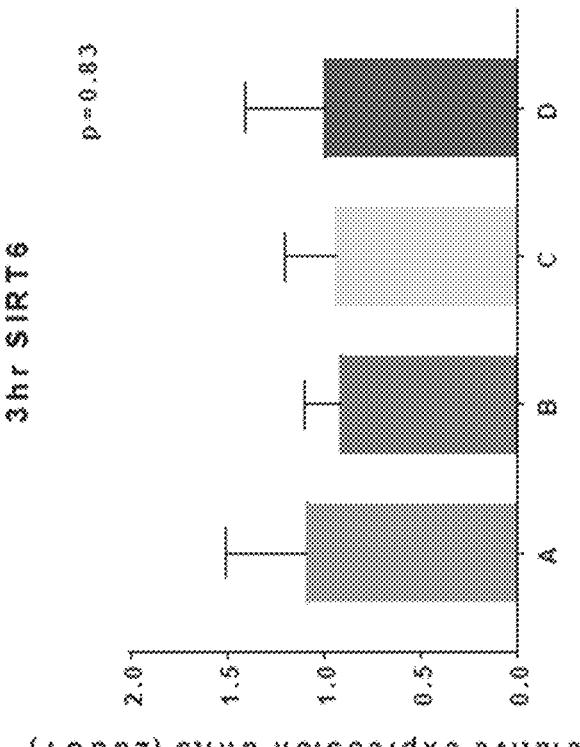
Figure 1B:
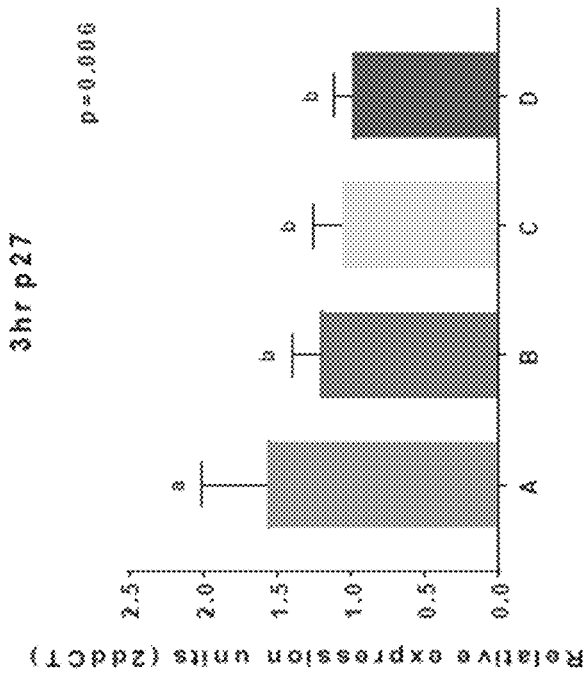
Figure 1B:
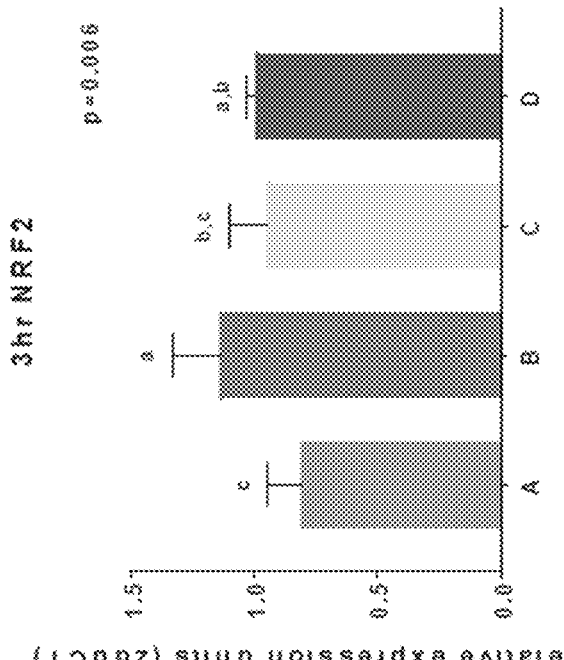
Figure 1C:
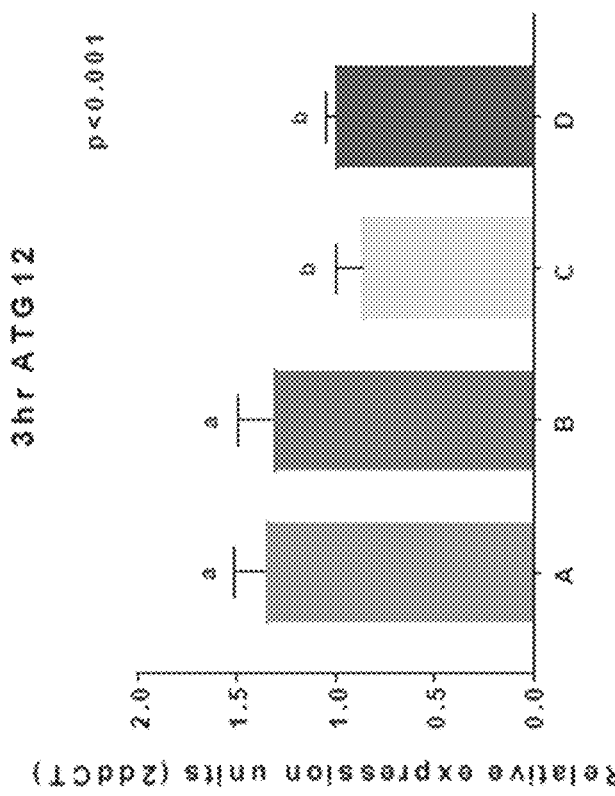
Figure 1C:
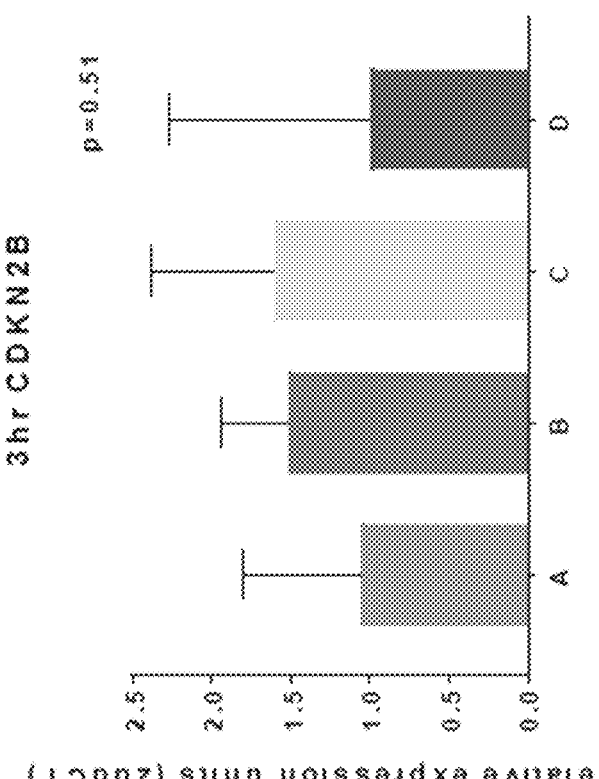
Figure 1D:
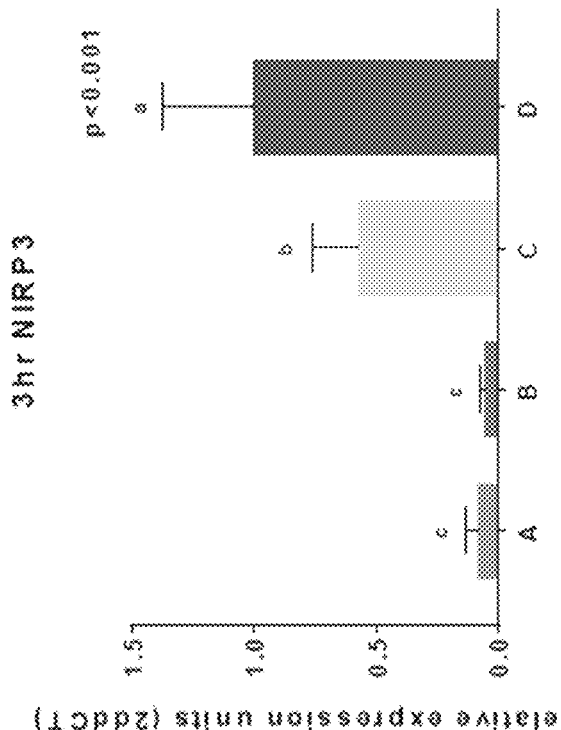
Figure 1D:
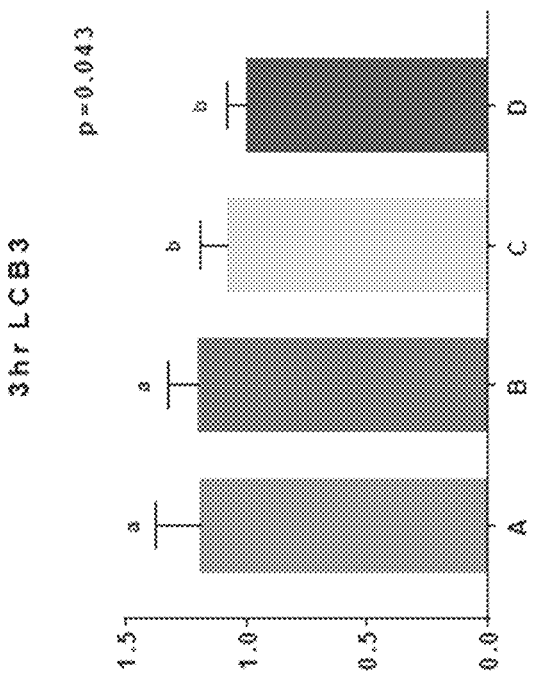
Figure 1E:
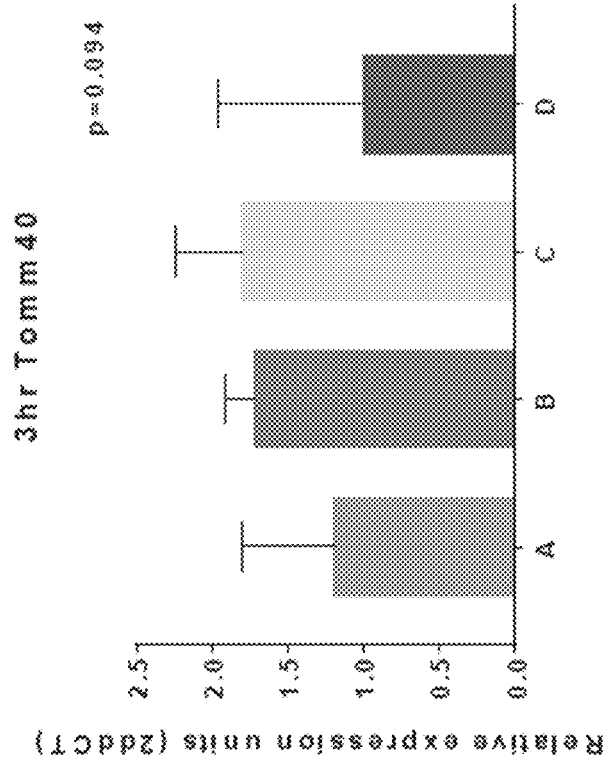
Figure 1E:
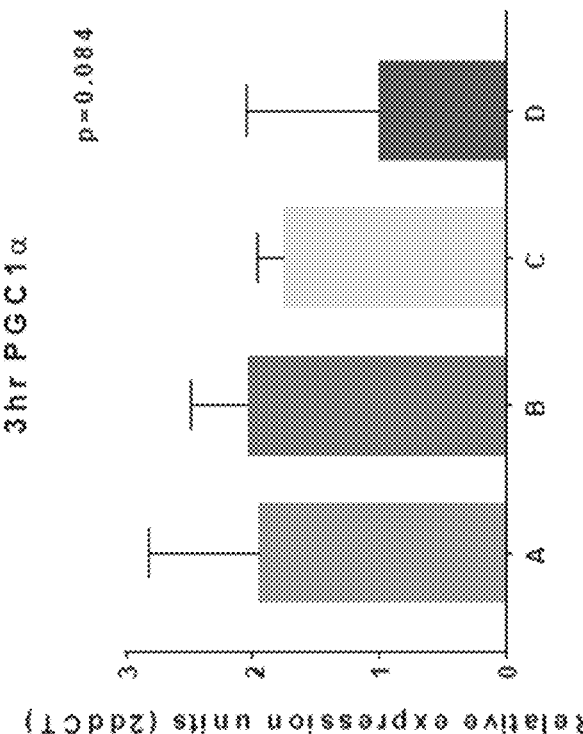
Figure 1F:
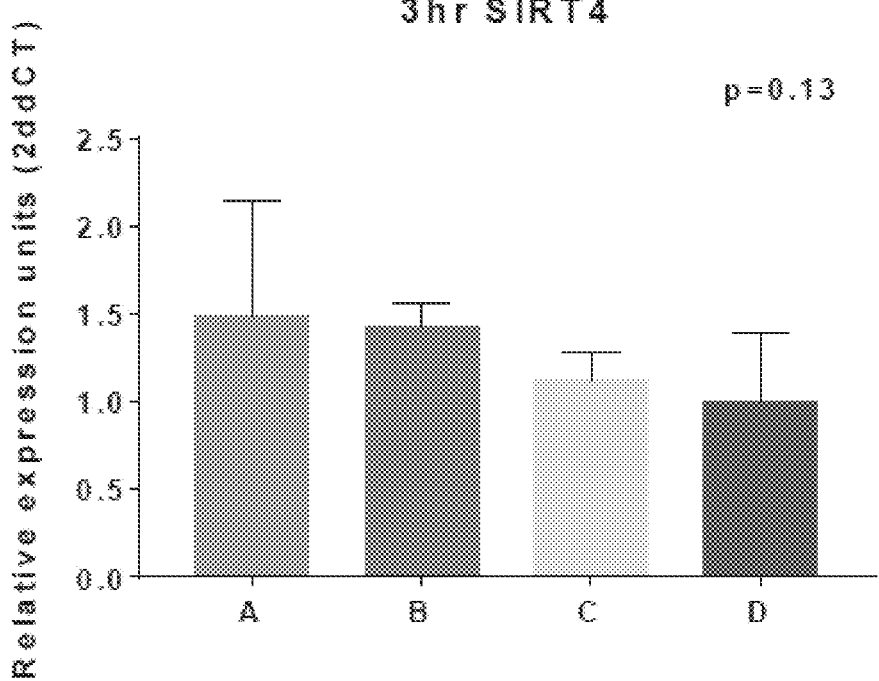
Figure 2A:
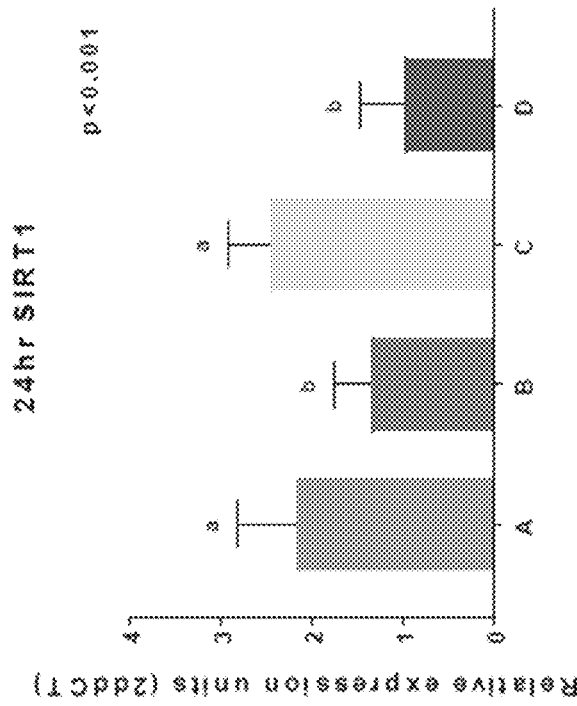
FIGS. 2A-2F depict exemplary results for mRNA data SIRT6, SIRT1, NRF2, p2'7, CDKN2B, ATG12, LCB3, NLRP3, PGC1α, Tomm40, and SIRT4, as indicated, for 24-hr treatments with Group A, B, C, or D treatments as indicated and as described herein. One-way ANOVAs were performed to determine if treatments significantly differed, and LSD post hoc tests were performed in order to determine where the significance occurred. Treatments with different superscript letters (a, b, c, or d) indicate treatments differed from each other.
Figure 2A:
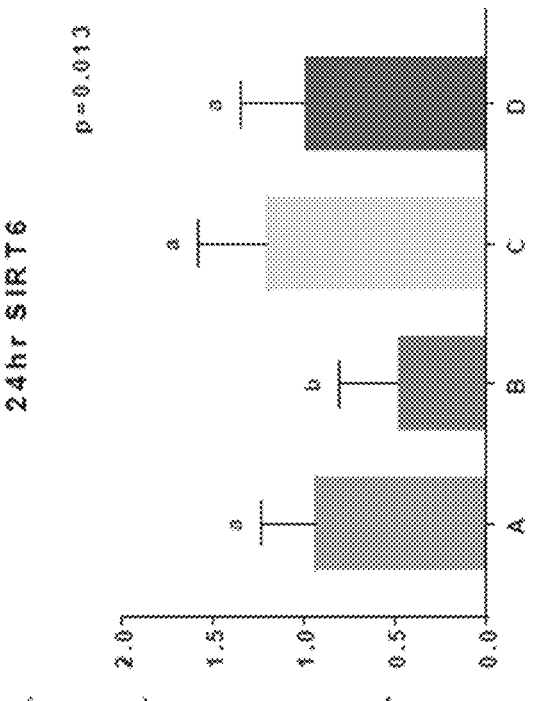
Figure 2B:
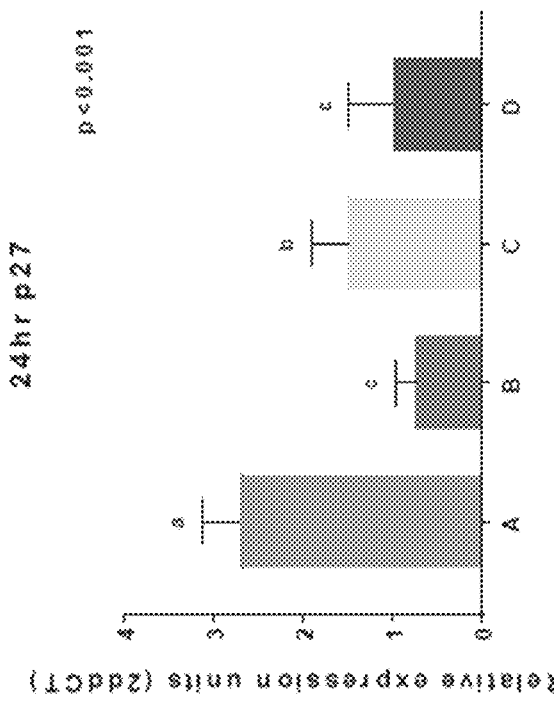
Figure 2B:
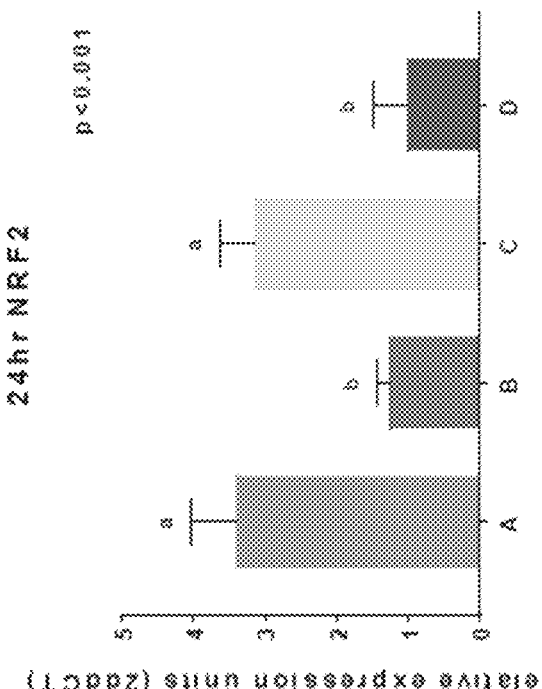
Figure 2C:
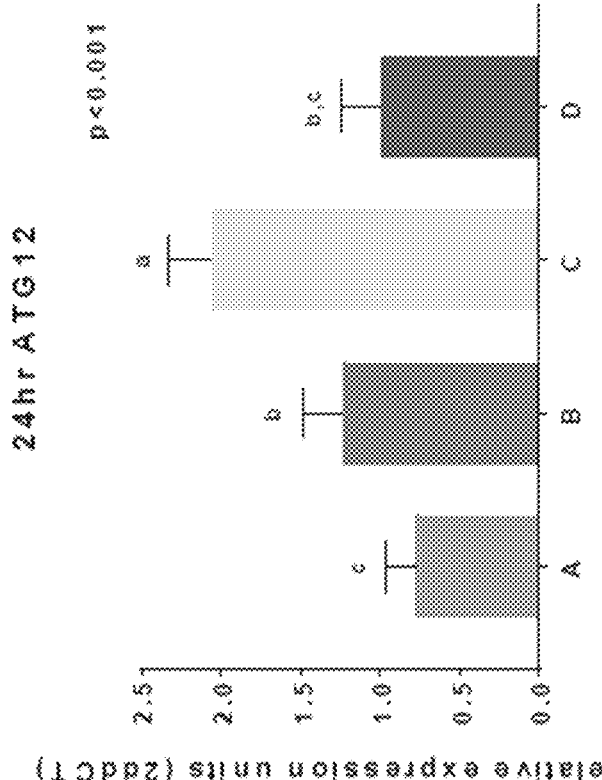
Figure 2C:
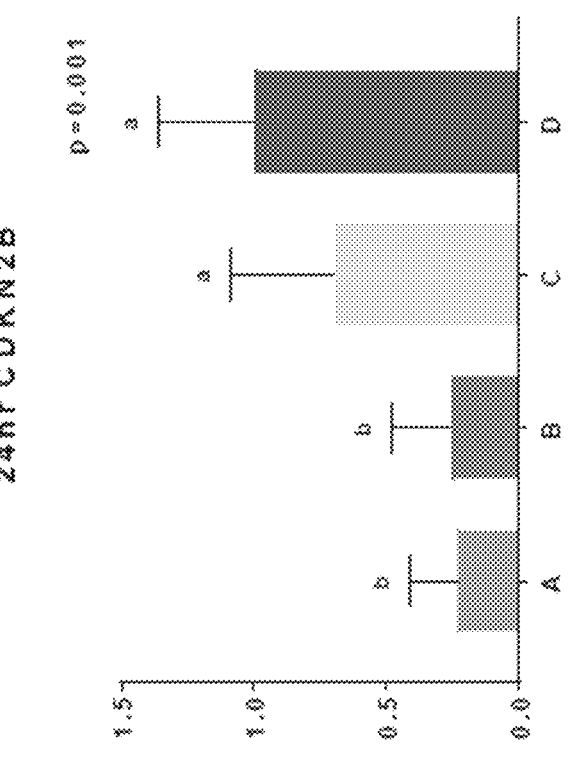
Figure 2D:
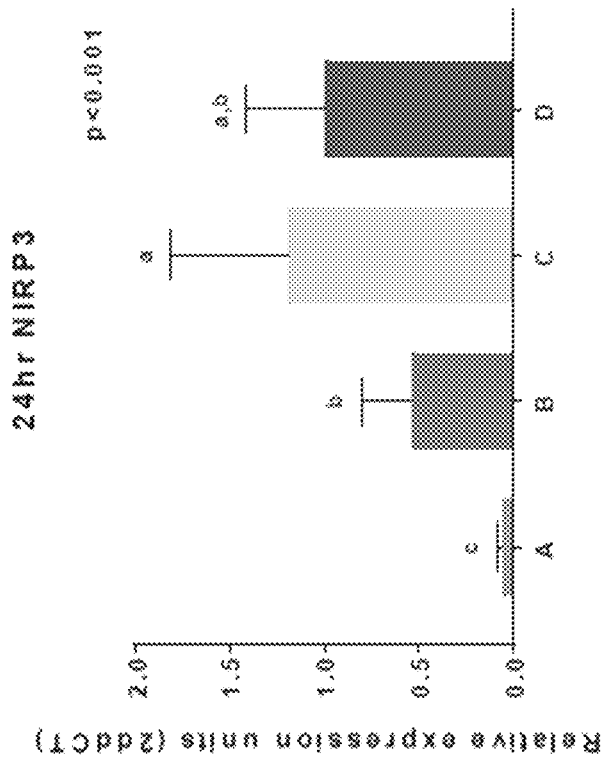
Figure 2D:
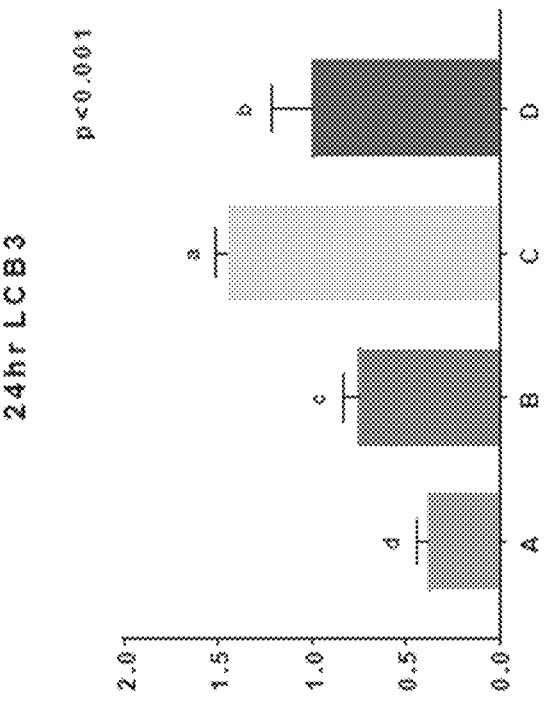
Figure 2E:
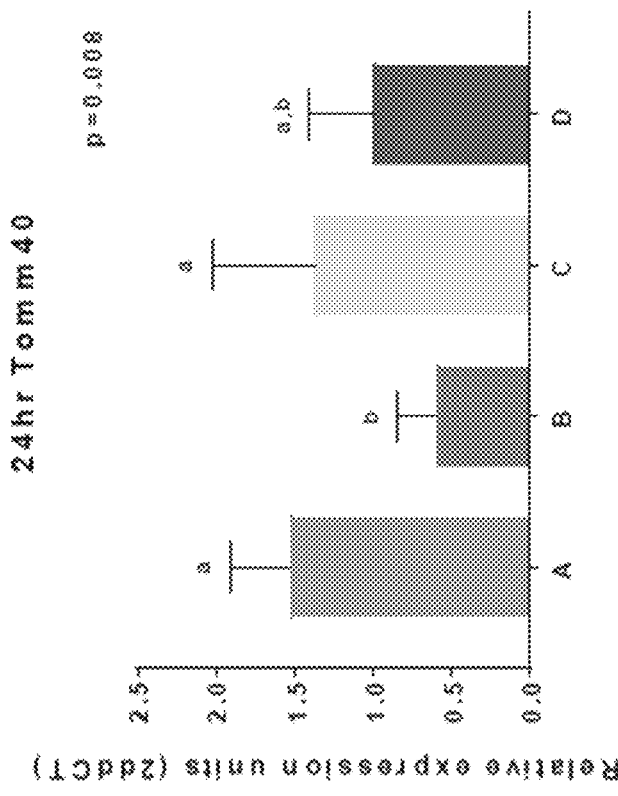
Figure 2E:
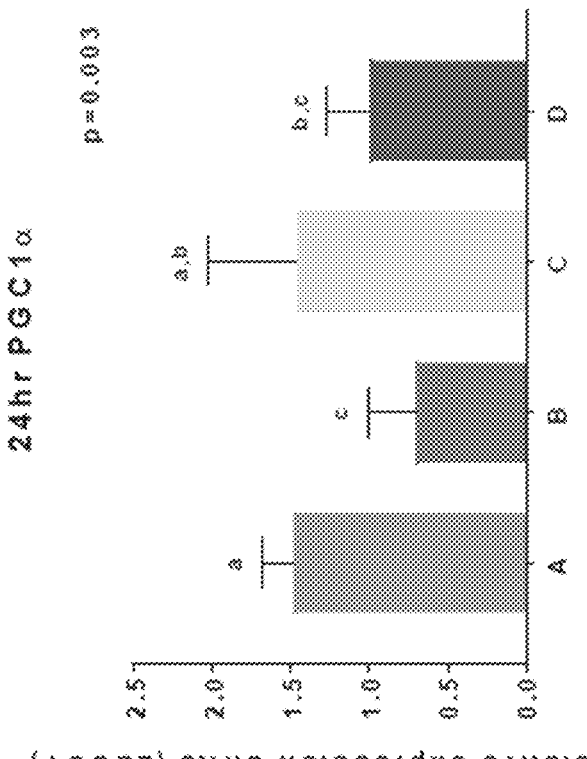
Figure 2F:
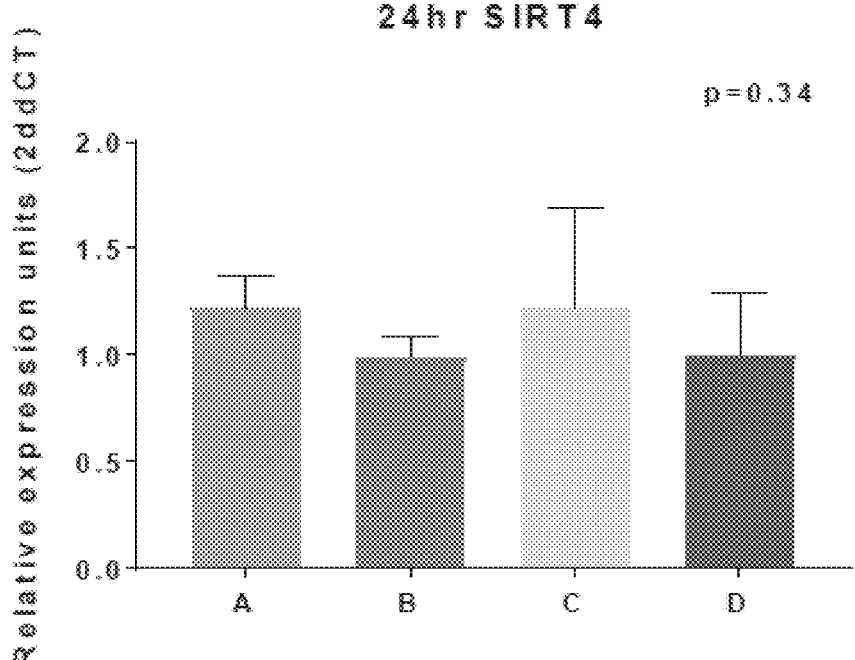
Figure 3:
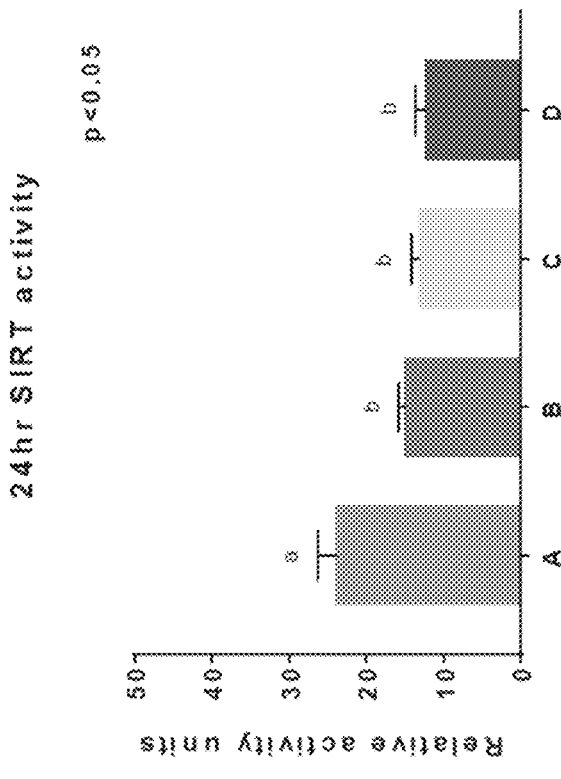
FIG. 3 depicts exemplary results for SIRT activity for 3 hour and 24 hour treatments with Group A, B, C, or D, as indicated and as described herein. One-way ANOVAs were performed to determine if treatments significantly differed, and LSD post hoc tests were performed in order to determine where the significance occurred. Treatments with different superscript letters indicates treatments differed from each other.
Figure 3:
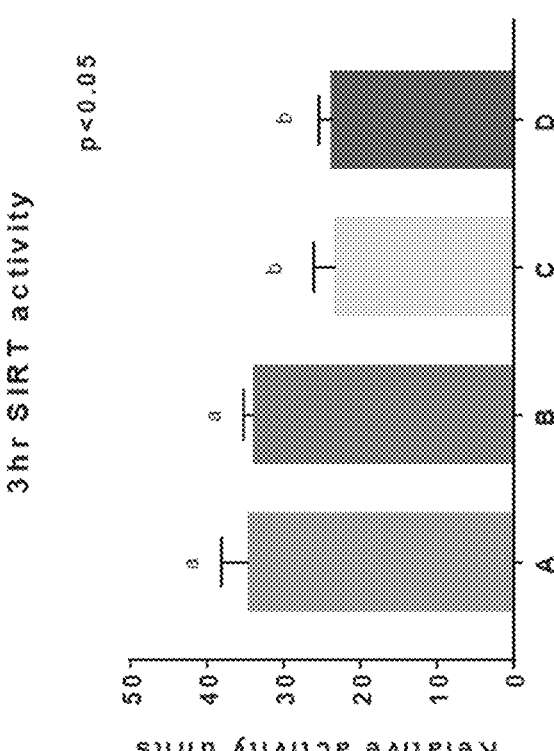

FIG. 3 depicts exemplary results for SIRT activity for 3 hour and 24 hour treatments with Group A, B, C, or D, as indicated and as described herein. One-way ANOVAs were performed to determine if treatments significantly differed, and LSD post hoc tests were performed in order to determine where the significance occurred. Treatments with different superscript letters indicates treatments differed from each other.

Figure 4:
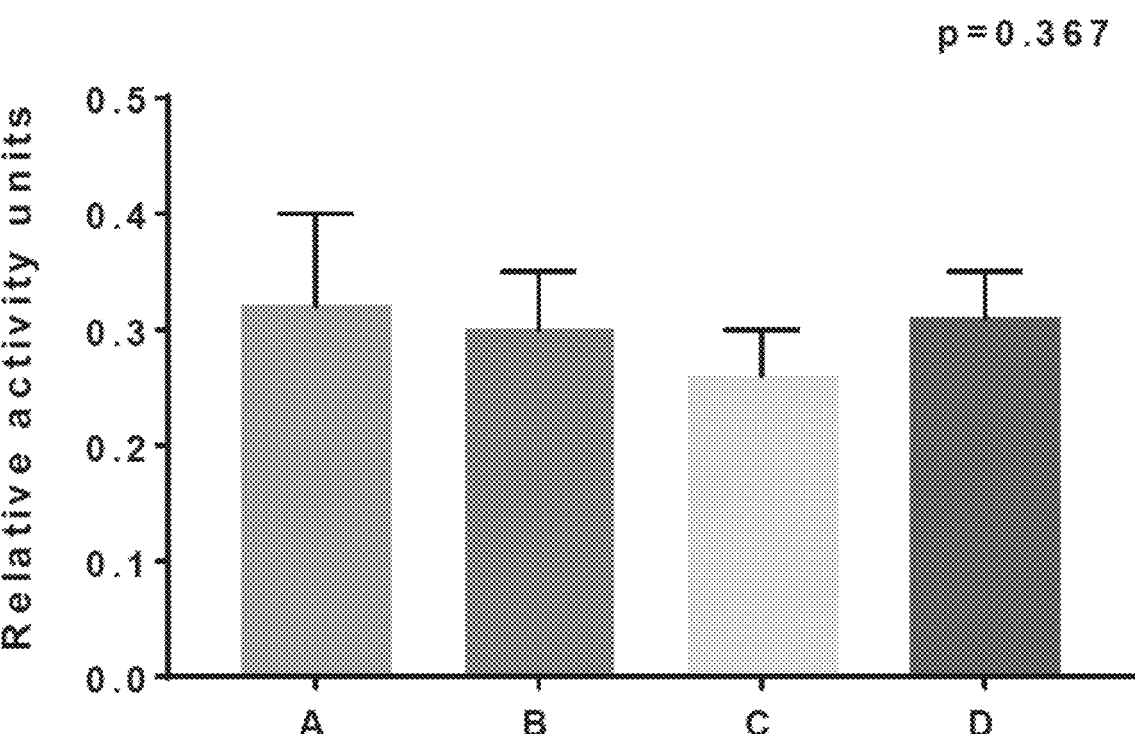
FIG. 4 depicts exemplary results for citrate synthase activity (mitochondrial capacity marker) following 24 h treatments with Group A, B, C, or D, as indicated and as described herein. One-way ANOVAs were performed to determine if treatments significantly differed, but the ANOVA yielded p=0.367.

FIG. 4 depicts exemplary results for citrate synthase activity (mitochondrial capacity marker) following 24 h treatments with Group A, B, C, or D, as indicated and as described herein. One-way ANOVAs were performed to determine if treatments significantly differed, but the ANOVA yielded p=0.367.

Figure 5A:
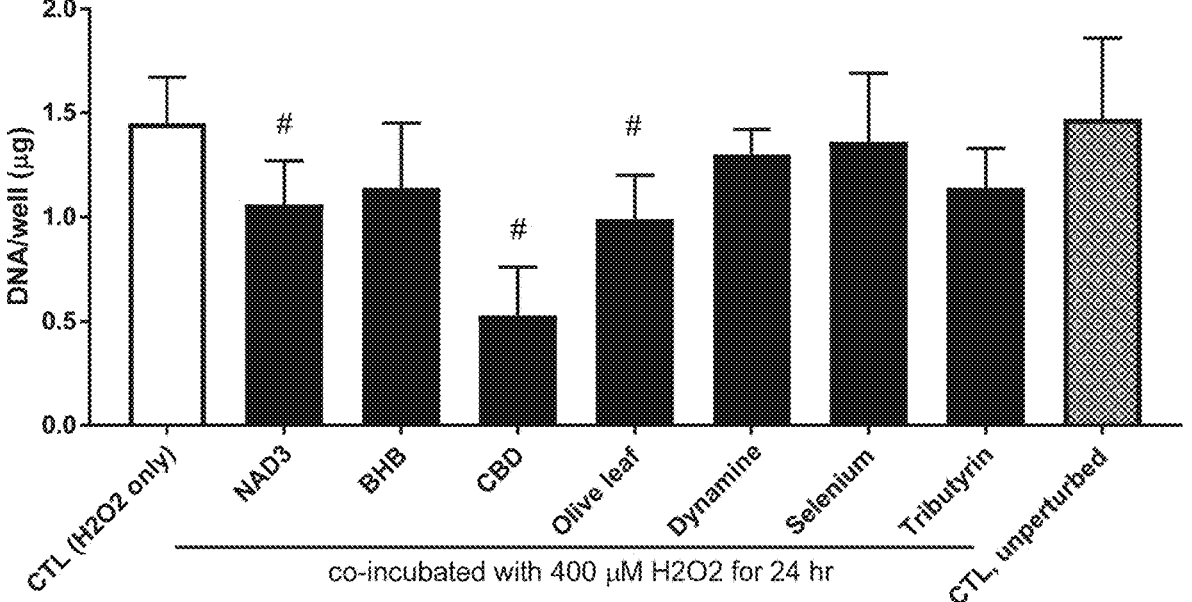
FIG. 5A depicts exemplary results for cell viability (DNA/well (ug)) for cells incubated without hydrogen peroxide (CTL, unperturbed), cells incubated with hydrogen peroxide (H2O2), and cells co-incubated with NAD3, BHB, CBD, olive leaf, dynamine, selenium, or tributyrin as indicated.

FIG. 5A depicts exemplary results for cell viability (DNA/well (ug)) for cells incubated without hydrogen per-oxide (CTL, unperturbed), cells incubated with hydrogen peroxide (H2O2), and cells co-incubated with NAD3, BHB, CBD, olive leaf, dynamine, selenium, or tributyrin as indi-cated.

Figure 5B:
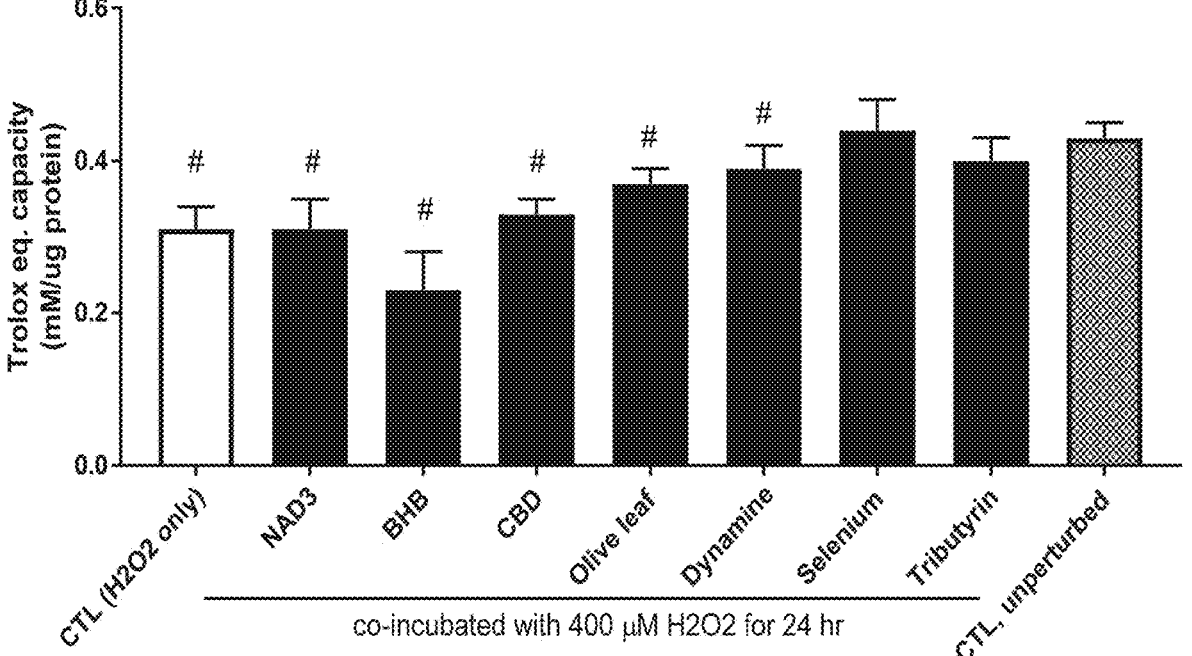
FIG. 5B depicts exemplary results for total antioxidant capacity (Trolox) for cells incubated without hydrogen peroxide (H2O2) (CTL, unperturbed), cells incubated with H2O2, and cells co-incubated with NAD3, BHB, CBD, olive leaf, dynamine, selenium, or tributyrin as indicated.

FIG. 5B depicts exemplary results for total antioxidant capacity (Trolox) for cells incubated without hydrogen per-oxide (H2O2) (CTL, unperturbed), cells incubated with H2O2, and cells co-incubated with NAD3, BHB, CBD, olive leaf, dynamine, selenium, or tributyrin as indicated. As shown, Selenium as well as Tributyrin increase or restore antioxidant capacity in the presence of H2O2.

FIG. 6A depicts exemplary results for autophagy for cells incubated without hydrogen peroxide (H2O2) (CTL, unper-turbed), cells incubated with H2O2, and cells co-incubated with NAD3, BHB, CBD, olive leaf, dynamine, selenium, or tributyrin as indicated.

FIG. 6B depicts exemplary results for DNA damage for cells incubated without hydrogen peroxide (H2O2) (CTL, unperturbed), cells incubated with H2O2, and cells co-incubated with NAD3, BHB, CBD, olive leaf, dynamine, selenium, or tributyrin as indicated.

FIG. 6C depicts exemplary results for cellular oxidative stress for cells incubated without hydrogen peroxide (H2O2) (CTL, unperturbed), cells incubated with H2O2, and cells co-incubated with NAD3, BHB, CBD, olive leaf, dynamine, selenium, or tributyrin as indicated.

FIG. 7A depicts exemplary results for autophagy for cells incubated for 6 hours without hydrogen peroxide (H2O2) (CTL, vehicle (veh) only), and cells incubated with NAD3, BHB, CBD, olive leaf, dynamine, selenium, or tributyrin as indicated.

FIG. 7B depicts exemplary results for quantifying NAMPT protein levels in cells incubated for 6 hours without hydrogen peroxide (H2O2) (CTL, vehicle (veh) only), and cells incubated with NAD3, BHB, CBD, olive leaf, dynamine, selenium, or tributyrin as indicated.

FIG. 7C depicts exemplary results for quantifying PGC1α protein levels in cells incubated for 6 hours without hydrogen peroxide (H2O2) (CTL, vehicle (veh) only), and cells incubated with NAD3, BHB, CBD, olive leaf, dynamine, selenium, or tributyrin as indicated.

FIG. 8A depicts exemplary results for cell viability (DNA/well (ug)) for cells incubated without hydrogen peroxide (CTL, unperturbed), cells incubated with hydrogen peroxide (H2O2), and cells co-incubated with NAD3, NAD3+CBD, NAD3+olive leaf, NAD3+BHB, NAD3+dynamine, NAD3+selenium, or NAD3+grape seed, as indicated.

FIG. 8B depicts exemplary results for total antioxidant capacity (Trolox) for cells incubated without hydrogen peroxide (H2O2) (CTL, unperturbed), cells incubated with H2O2, and cells co-incubated with NAD3, NAD3+CBD, NAD3+olive leaf, NAD3+BHB, NAD3+dynamine, NAD3+selenium, or NAD3+grape seed, as indicated.

FIG. 9A depicts exemplary results for autophagy for cells incubated without hydrogen peroxide (H2O2) (CTL, unperturbed), cells incubated with H2O2, and cells co-incubated with NAD3, NAD3+CBD, NAD3+olive leaf, NAD3+BHB, NAD3+dynamine, NAD3+selenium, or NAD3+grape seed, as indicated.

FIG. 9B depicts exemplary results for DNA damage for cells incubated without hydrogen peroxide (H2O2) (CTL, unperturbed), cells incubated with H2O2, and cells co-incubated with NAD3, NAD3+CBD, NAD3+olive leaf, NAD3+BHB, NAD3+dynamine, NAD3+selenium, or NAD3+grape seed, as indicated.

FIG. 9C depicts exemplary results for quantifying inflammasome induction by measuring the amount of NLRP3 protein in cells incubated without hydrogen peroxide (H2O2) (CTL, unperturbed), cells incubated with H2O2, and cells co-incubated with NAD3, NAD3+CBD, NAD3+olive leaf, NAD3+BHB, NAD3+dynamine, NAD3+selenium, or NAD3+grape seed, as indicated.

FIG. 10A depicts exemplary results for autophagy for cells incubated for 6 hours without hydrogen peroxide (H2O2) (CTL), and cells incubated with NAD3, NAD3+CBD, NAD3+olive leaf, NAD3+BHB, NAD3+dynamine, NAD3+selenium, or NAD3+grape seed, as indicated.

FIG. 10B depicts exemplary results for quantifying NAMPT protein levels in cells incubated for 6 hours without hydrogen peroxide (H2O2) (CTL), and cells incubated with NAD3, NAD3+CBD, NAD3+olive leaf, NAD3+BHB, NAD3+dynamine, NAD3+selenium, or NAD3+grape seed, as indicated.

FIG. 10C depicts exemplary results for quantifying PGC1α protein levels in cells incubated for 6 hours without hydrogen peroxide (H2O2) (CTL), and cells incubated with NAD3, NAD3+CBD, NAD3+olive leaf, NAD3+BHB, NAD3+dynamine, NAD3+selenium, or NAD3+grape seed, as indicated.

FIG. 10D depicts exemplary results for quantifying total SIRT activity in cells incubated for 6 hours without hydrogen peroxide (H2O2) (CTL), and cells incubated with NAD3, NAD3+CBD, NAD3+olive leaf, NAD3+BHB, NAD3+dynamine, NAD3+selenium, or NAD3+grape seed, as indicated.

FIG. 11A depicts representative protein gels of C2C12 (muscle cells) with Western blotting analysis shown for p-H2AX, LC3I, LC3II, 4HNE, and NLRP3, and Ponceau protein staining, as indicated.

FIG. 11B depicts representative protein gels of EOMA (endothelial cells) with Western blotting analysis shown for p-H2AX, LC3I, LC3II, 4HNE, and NLRP3, and Ponceau protein staining, as indicated.

As can be readily taken form the results, acute (3 hrs) and longer term (24 hrs) effects on various markers were observed for contemplated combinations. For example, acute differences were, inter alia, observable for SIRT 1, SIRT6, and SIRT4, as well as for p2'7, PGC1α, and NLRP3, while longer term results were apparent for p2'7, CDKN2B, LCB3, NLRP3, and TOMM40.

Furthermore, with specific reference to FIG. 5B, tributyrin and selenium were observed to increase (e.g., restore) total antioxidant activity when cells were co-incubated with either tributyrin or selenium and H2O2. Similarly, with reference to FIG. 8B, NAD3 and Olive leaf, NAD3 and BHB, NAD3 and Selenium, and NAD3 and Grape Seed extract all increase total antioxidant capacity over cells treated with H2O2.

Additionally, with specific reference to FIG. 6C, beta hydroxybutyrate (BHB) was observed to decrease cellular oxidative stress in cells co-incubated with H2O2 and BHB. And notably, with reference to FIG. 9C, NAD3 in combination with olive leaf, BHB, dynamine, selenium, and grape seed extract decreased the induction of NLRP3 in the present of H2O2 (oxidative stress).

In summary, as introduced above, the inventors sought to examine how NAD3 affects molecular markers in skeletal muscle cells. Notably, NAD3 treatments increased Sirt1 mRNA levels as well as global sirtuin activity relative to CTL-treated cells. Follow-up experiments on 24 h treated cells indicated NAD3 treatments increased SIRT1 protein levels, NAMPT protein levels, and cellular NAD+ concentrations. However, while certain mRNA markers related to mitochondrial biogenesis were altered with NAD3 treatments, citrate synthase activity levels (a surrogate of mitochondrial volume) were not affected with 24 h NAD3 treatments.

In particular, the study showed that NAD3 treatments upregulate the mRNA and protein levels of SIRT1 suggest that enhanced global sirtuin activity levels may occur through an increase in this specific sirtuin. The NAD3-induced increase in NAMPT protein levels is interesting given that NAD+ biosynthesis can be catalyzed through the salvage/recycling pathway and NAMPT is the rate-limiting enzyme in this pathway. The two-fold increase in cellular NAD+ concentrations after 24 h of NAD3 treatment may be related to the aforementioned effect and critically, this too may be a mechanism that is involved with the robust increase in sirtuin activity observed herein.

In spite of the NAD3-induced increase in global sirtuin activity as well as the NAD3-induced increase in Nfe212 mRNA levels, protein levels of NRF2 as well as mitochondrial biogenesis (as assessed through citrate synthase activity) remained unaltered. Although this finding is difficult to reconcile, it may be possible that NAD3, rather than appreciably affecting mitochondrial biogenesis, enhanced mitochondrial function.

Example Set 2: In Vivo Analysis

Example Protocols for In Vivo Analysis

The inventors examined how 12 weeks of daily supplementation of human subjects with a control composition including cellulose pills, an exemplary cytoprotective composition I including 311 mg of combined *Wasabia japonica*, theacrine, and cuprous niacin (also referred to herein as "NAD3"), and an exemplary cytoprotective composition II including 311 mg of combined *Wasabia japonica*, theacrine, cuprous niacin, and tributyrin (also referred to herein as "NAD3+TB") altered biomarkers, a variety of biological variables, gene expression, NAD+ metabolites in PBMCs, and serum lipids in the human subjects. Eligible subjects were between the ages of 40-65 years, have a BMI between 18.5-34.9 kg/m2, and were free from cardio-metabolic diseases (e.g., morbid obesity, type II diabetes, severe hypertension) as determined via questionnaires.

Baseline (Pre) testing occurred following an overnight fast. During this test, subjects had their body mass obtained using a digital column scale (Seca 769; Hanover, MD, USA) with height and body mass collected to the nearest 0.5 cm and 0.1 kg, respectively. Thereafter, subjects were seated and blood pressure was obtained from the right arm following a five-minute wait period using an automated sphygmomanometer. Venous blood was then obtained by a research nurse in a 5 mL serum separator tube (BD Vacutainer, Franklin Lakes, NJ, USA). Approximately 30 minutes following collection, tubes were centrifuged at 3,500 g for 5 minutes at room temperature. Serum aliquots were placed in 1.7 mL polypropylene tubes and stored at −80° C. until batch-processing for serum analyses. A second 4 mL tube of blood (CPT Cell Preparation Tube; BD Vacutainer) was collected for the fresh isolation of PBMCs. Briefly, upon blood collection into these tubes, tubes were inverted ~8 times and set to incubate at room temperature for approximately 30 minutes. Thereafter, tubes were centrifuged at 1500 g for 20 minutes at room temperature. Buffy coat aliquots were obtained following centrifugation, placed in 1.7 mL polypropylene tubes and stored at −80° C. until batch-processing for PBMC analyses.

mercial vendor (Creative Proteomics; Shirley, NY, USA). Standard substances of three targeted compounds (NAD+, NADH, NAAD) were used to prepare a stock standard solution freshly in a 13C10-GTP internal standard-Tris buffer solution. This solution was serially diluted to prepare calibration solutions. The concentration range was 0.0025 to 40 nM for each compound. After thawing PBMC lysates on ice, the volume of the liquid in each sample was topped to 100 μL with Tris buffer. 400 μL of deoxygenated ethanol was then added to each tube. Samples were vortexed for 1 minute and sonicated for 30 seconds, followed by centrifugal clarification for 10 minutes at 5° C. The pellets were used for protein assays in order to normalize values. 150 μL of the clear supernatant of each sample was dried at room temperature under a nitrogen gas flow in the dark. The residue was reconstituted in 100 μL of the internal standard solution. 20-μL aliquots of the resultant sample solutions and the calibration solutions were injected for liquid chromatography-mass spectrometric multiple reaction monitoring (LC-MS/MRM) on a Waters Acquity UPLC coupled to a Sciex QTRAP 6500 Plus mass spectrometer with (−) ion detection. A reversed-phase C18 column (2.1*100 mm, 1.8 μm) was used for LC separation, with a tributylamine buffer (solvent A) and methanol (solvent B) as the mobile phase for binary solvent gradient elution of 5% to 90% B over 25 min at 50° C. and 0.25 mL/min. Calibration curves of individual metabolites were constructed with internal calibration. Concentrations of individual metabolites detected in each sample were calculated by interpolating the calibration curves with the peak area ratios measured from injections of sample solutions.

In Vivo Analysis I

In an in vivo study, the inventors assessed the impact of supplementing the diet of several subjects with the control composition (referenced in the Tables below as "101"), the exemplary cytoprotective composition I (referenced in the Tables below as "201") and the exemplary cytoprotective composition II (referenced in the Tables below as "301") on changes in biomarkers for a 12-week period. The study design is shown below in Table 1.

TABLE 1

| Example Set 2 Study Design | | | | | | |
| --- | --- | --- | --- | --- | --- | --- |
| Procedure | Screening | Visit 2 (week 0) | Visit 3 (week 1) | Visit 4 (week 4) | Visit 5 (week 8) | Visit 6 (week 12) |
| Informed Consent | X | | | | | |
| Inclusion/Exclusion Criteria | X | | | | | |
| Medical History | X | | | | | |
| Medication and Supplement History | X | X | | | | |
| Physical Exam | X | | | | | |
| Hgt, weight (BMI), and vitals (BP and HR) | X | X | X | X | X | X |
| CMP, LP, CBC, and insulin, * | X | | | X | X | X |
| c-Reactive Protein | X | | X | X | X | X |
| HbA1C | X | | | | X | X |
| Natural Killer Cells & Activated T-cell profile | | X | | | | X |
| Randomization | X | | | | | |
| VAS questionnaire | | X | X | X | X | X |
| Diet Records/Analysis | X | X | | X | X | X |
| Physical Activity Questionnaire | | X | X | X | X | X |
| Protocol Compliance (pill counts and log check) | | X | X | X | X | X |
| Dispense Test Product | | X | X | X | X | |
| Concomitant Medication Review | X | X | X | X | X | X |
| Adverse Events Monitoring | | X | X | X | X | X |

Serum markers were analyzed using through LabCorp (Dublin, OH). Targeted NAD+ metabolomics was performed on PBMC lysates in a blinded fashion by a com- In particular, the inventors assessed the following biomarkers and variables of the subjects: Body Mass, Systolic Blood Pressure, Diastolic Blood Pressure, Heart Rate, Energy Visual Analog Scale (VAS), Mood VAS, Low Fatigue VAS, Clear Mind VAS, Handle Difficult Projects VAS, Ability to Concentrate VAS, Willing to Perform Exercise VAS, Willing to Perform Mental Tasks VAS, Enthusiasm VAS, State of Well-Being VAS, Ability to Handle Stress VAS, Productivity VAS, Quality of Sleep VAS, Digestive Health VAS, Quality of Bowel Movements VAS, Abdominal Bloating VAS, White Blood Cell Count, Red Blood Cell Count, White Blood Cell Count, Red Blood Cell Count, Hemoglobin, Hematocrit, Mean Corpuscle Volume, Mean Corpuscle Hemoglobin, Mean Corpuscle Hemoglobin Content, Red Cell Dimension Width, Platelets, Neutrophils (Absolute & %), Lymphocytes (Absolute & %), Monocytes (Absolute & %), Eosinophils (Absolute & %), Basophils (Absolute & %), Immature Granulocytes (Abs & %), Glucose, Blood Urea Nitrogen (BUN), Creatinine, BUN: Creatinine ratio, Sodium, Potassium, Chloride, Carbon Dioxide, Calcium, Protein, Albumin, Globulin, Albumin: Globulin Ratio, Bilirubin, Alkaline Phosphatase, AST, ALT, Total Cholesterol, Triglycerides, HDL cholesterol, VLDL cholesterol, LDL cholesterol, LDL: HDL Ratio, Hemoglobin A1C, Insulin, and C-Reactive Protein. Unless otherwise noted and according to Table 1 above, all outlined biomarkers and variables were collected on visit 2 (day 7), visit 4 (week 4), visit 5 (week 8), and visit 6 (week 12).

Anthropometric and hemodynamic variables were assessed for each subject at 0 weeks, 4 weeks, 8 weeks, and 12 weeks. A summary of the results is shown in Table 2 below. These results were analyzed at 4 weeks, 8 weeks, and 12 weeks relative to the baseline, which is shown in Tables 3-5 below. 95% CI=95% Confidence Interval of the observed difference between groups. ES=Effect size computation of change between groups.

TABLE 2

| | | Anthropometric and Hemodynamic Variables | | | | | | |
|---|---|---|---|---|---|---|---|---|
| Variables | Group | Visit 2 (Week 0) | Visit 4 (Week 4) | Visit 5 (Week 8) | Visit 6 (Week 12) | Within-Group | | p |
| Body Mass | 101 | 176.1 ± 33.4 | 176.5 ± 33.3 | 176.7 ± 34.5 | 177.0 ± 34.4 | 0.47 | Group | 0.51 |
| (lbs) | 201 | 191.8 ± 46.0 | 191.5 ± 45.9 | 191.5 ± 45.9 | 192.7 ± 48.2 | 0.66 | Time | 0.52 |
| | 301 | 192.5 ± 41.5 | 191.7 ± 42.4 | 191.7 ± 32.4 | 191.2 ± 41.0 | 0.21 | G × T | 0.26 |
| | | | | | | | ANCOVA | 0.20 |
| Body Mass | 101 | 80.0 ± 15.2 | 80.2 ± 15.1 | 80.3 ± 15.7 | 80.4 ± 15.7 | 0.50 | Group | 0.51 |
| (kg) | 201 | 87.2 ± 20.9 | 87.1 ± 20.9 | 87.2 ± 21.8 | 87.6 ± 21.9 | 0.66 | Time | 0.50 |
| | 301 | 87.5 ± 18.8 | 87.2 ± 19.3 | 86.5 ± 18.8 | 86.9 ± 18.6 | 0.20 | G × T | 0.27 |
| | | | | | | | ANCOVA | 0.19 |
| Heart Rate | 101 | 67.7 ± 6.4 | 70.1 ± 7.6 | 68.1 ± 4.7 | 70.7 ± 7.4 | 0.15 | Group | 0.56 |
| (bpm) | 201 | 69.2 ± 9.0 | 70.0 ± 9.3 | 69.8 ± 8.6 | 71.2 ± 8.8 | 0.90 | Time | 0.43 |
| | 301 | 66.5 ± 8.4 | 68.5 ± 11.7 | 67.5 ± 10.5 | 66.1 ± 9.1 | 0.50 | G × T | 0.77 |
| | | | | | | | ANCOVA | 0.28 |
| Systolic | 101 | 127.7 ± 14.9 | 125.7 ± 9.6 | 128.3 ± 10.7 | 126.8 ± 9.4 | 0.79 | Group | 0.70 |
| Blood | 201 | 126.9 ± 11.2 | 123.1 ± 13.3 | 126.7 ± 11.6 | 128.7 ± 7.9 | 0.23 | Time | 0.07 |
| Pressure | 301 | 130.0 ± 16.2 | 126.7 ± 12.7 | 132.1 ± 12.9 | 128.9 ± 11.1 | 0.24 | G × T | 0.86 |
| (mm Hg) | | | | | | | ANCOVA | 0.73 |
| Diastolic | 101 | 79.8 ± 7.4 | 80.9 ± 9.0 | 80.7 ± 6.7 | 80.4 ± 7.9 | 0.94 | Group | 0.90 |
| Blood | 201 | 78.2 ± 10.4 | 78.5 ± 9.0 | 80.2 ± 7.2 | 80.0 ± 6.9 | 0.57 | Time | 0.98 |
| Pressure | 301 | 80.5 ± 10.7 | 79.7 ± 10.7 | 78.9 ± 10.0 | 78.3 ± 9.8 | 0.70 | G × T | 0.73 |
| (mm Hg) | | | | | | | ANCOVA | 0.25 |

TABLE 3

| | | 4-Week Changes from Baseline (Anthropometric and Hemodynamic Variables) | | | | | | |
|---|---|---|---|---|---|---|---|
| Variables | Group | Week 4 Delta | p-value | | 95% CI | p-value | ES |
| Body Mass | 101 | 0.45 ± 2.00 | 0.37 | 101 vs. 201 | (−1.11, 2.66) | 0.41 | −0.34 |
| (lbs) | 201 | −0.32 ± 2.54 | | 101 vs. 301 | (−0.51, 3.01) | 0.16 | −0.52 |
| | 301 | −0.79 ± 2.75 | | 201 vs. 301 | (−1.36, 2.30) | 0.61 | −0.18 |
| Body Mass | 101 | 0.21 ± 0.91 | 0.35 | 101 vs. 201 | (−0.51, 1.19) | 0.43 | −0.33 |
| (kg) | 201 | −0.13 ± 1.16 | | 101 vs. 301 | (−0.22, 1.37) | 0.15 | −0.54 |
| | 301 | −0.37 ± 1.23 | | 201 vs. 301 | (−0.59, 1.07) | 0.56 | −0.20 |
| Systolic | 101 | 2.4 ± 6.0 | 0.87 | 101 vs. 201 | (−5.82, 9.51) | 0.63 | −0.18 |
| Blood | 201 | 0.8 ± 12.5 | | 101 vs. 301 | (−6.11, 8.22) | 0.77 | −0.10 |
| Pressure | 301 | 2.2. ± 7.1 | | 201 vs. 301 | (−8.24, 6.66) | 0.83 | 0.08 |
| (mm Hg) | | | | | | | |
| Diastolic | 101 | −2.0 ± 10.5 | 0.89 | 101 vs. 201 | (−5.50, 6.86) | 0.83 | −0.10 |
| Blood | 201 | −3.8 ± 9.6 | | 101 vs. 301 | (−4.48, 7.08) | 0.65 | −0.16 |
| Pressure | 301 | −3.1 ± 9.9 | | 201 vs. 301 | (−5.39, 6.63) | 0.84 | −0.07 |
| (mm Hg) | | | | | | | |
| Heart Rate | 101 | 1.1 ± 6.3 | 0.90 | 101 vs. 201 | (−5.03, 8.29) | 0.62 | −0.18 |
| (bpm) | 201 | 0.4 ± 6.9 | | 101 vs. 301 | (−6.01, 6.45) | 0.94 | −0.10 |
| | 301 | −0.2 ± 10.0 | | 201 vs. 301 | (−7.89, 5.07) | 0.66 | 0.08 |

TABLE 4

| 8-Week Changes from Baseline (Anthropometric and Hemodynamic Variables) | | | | | | | |
|---|---|---|---|---|---|---|---|
| Variables | Group | Week 8 Delta | p-value | | 95% CI | p-value | ES |
| Body Mass | 101 | 0.60 ± 2.19 | 0.06 | 101 vs. 201 | (−2.00, 3.10) | 0.66 | −0.18 |
| (lbs) | 201 | 0.05 ± 3.83 | | 101 vs. 301 | (0.36, 5.20) | 0.03 | −0.90 |
| | 301 | −2.18 ± 3.76† | | 201 vs. 301 | (−0.29, 4.74) | 0.08 | −0.59 |
| Body Mass | 101 | 0.25 ± 0.98 | 0.06 | 101 vs. 201 | (−0.91, 1.40) | 0.67 | −0.17 |
| (kg) | 201 | 0.01 ± 1.75 | | 101 vs. 301 | (0.16, 2.35) | 0.03 | −0.90 |
| | 301 | −1.00 ± 1.69† | | 201 vs. 301 | (−0.13, 2.15) | 0.08 | −0.58 |
| Systolic | 101 | 0.40 ± 5.11 | 0.96 | 101 vs. 201 | (−7.35, 9.01) | 0.84 | −0.07 |
| Blood | 201 | 0.54 ± 6.58 | | 101 vs. 301 | (−9.42, 6.35) | 0.70 | 0.13 |
| Pressure | 301 | 1.00 ± 5.83 | | 201 vs. 301 | (−10.55, 5.82) | 0.56 | 0.29 |
| (mm Hg) | | | | | | | |
| Diastolic | 101 | 0.60 ± 14.22 | 0.84 | 101 vs. 201 | (−6.19, 4.06) | 0.68 | 0.16 |
| Blood | 201 | −0.23 ± 7.77 | | 101 vs. 301 | (−2.34, 7.54) | 0.29 | −0.40 |
| Pressure | 301 | 2.13 ± 8.49 | | 201 vs. 301 | (−1.46, 8.79) | 0.16 | −0.53 |
| (mm Hg) | | | | | | | |
| Heart Rate | 101 | 0.93 ± 6.24 | 0.33 | 101 vs. 201 | (−4.61, 4.33) | 0.95 | 0.02 |
| (bpm) | 201 | 2.00 ± 6.99 | | 101 vs. 301 | (−4.90, 3.70) | 0.78 | 0.11 |
| | 301 | −1.67 ± 6.87 | | 201 vs. 301 | (−4.93, 4.01) | 0.84 | 0.07 |

TABLE 5

| 12-Week Changes from Baseline (Anthropometric and Hemodynamic Variables) | | | | | | | |
|---|---|---|---|---|---|---|---|
| Variables | Group | Week 12 Delta | p-value | | 95% CI | p-value | ES |
| Body Mass | 101 | 0.97 ± 2.54 | 0.24 | 101 vs. 201 | (−3.08, 3.30) | 0.94 | −0.03 |
| (lbs) | 201 | 0.86 ± 4.27 | | 101 vs. 301 | (−0.72, 5.34) | 0.13 | −0.57 |
| | 301 | −1.34 ± 5.19 | | 201 vs. 301 | (−0.95, 5.34) | 0.17 | −0.46 |
| Body Mass | 101 | 0.43 ± 1.16 | 0.23 | 101 vs. 201 | (−1.42, 1.48) | 0.96 | −0.02 |
| (kg) | 201 | 0.40 ± 1.95 | | 101 vs. 301 | (−0.33, 2.42) | 0.13 | −0.56 |
| | 301 | −0.61 ± 2.35 | | 201 vs. 301 | (−0.41, 2.44) | 0.16 | −0.47 |
| Systolic | 101 | 2.93 ± 5.35 | 0.49 | 101 vs. 201 | (−11.0, 5.7) | 0.53 | 0.25 |
| Blood | 201 | 2.00 ± 10.95 | | 101 vs. 301 | (−8.1, 7.8) | 0.98 | 0.01 |
| Pressure | 301 | −0.13 ± 4.41 | | 201 vs. 301 | (−5.7, 10.8) | 0.54 | −0.25 |
| (mm Hg) | | | | | | | |
| Diastolic | 101 | −0.87 ± 12.0 | 0.78 | 101 vs. 201 | (−6.74, 4.25) | 0.65 | 0.17 |
| Blood | 201 | 1.77 ± 8.82 | | 101 vs. 301 | (−2.24, 8.19) | 0.26 | −0.41 |
| Pressure | 301 | −0.75 ± 11.5 | | 201 vs. 301 | (−1.20, 9.64) | 0.12 | −0.60 |
| (mm Hg) | | | | | | | |
| Heart Rate | 101 | 0.60 ± 7.35 | 0.27 | 101 vs. 201 | (−4.58, 6.45) | 0.73 | −0.11 |
| (bpm) | 201 | 1.85 ± 7.20 | | 101 vs. 301 | (−2.17, 8.29) | 0.25 | −0.62 |
| | 301 | −2.38 ± 7.01 | | 201 vs. 301 | (−3.31, 7.56) | 0.43 | −0.26 |

It was surprisingly discovered that the exemplary cytoprotective composition II provided a significant decrease in body mass to the subjects after 8 weeks and 12 weeks.

Blood lipids, inflammation, and glucose homeostasis variables were assessed for each subject at 0 weeks, 4 weeks, 8 weeks, and 12 weeks. A summary of the results is shown in Table 6 below and FIGS. 12A-12D. These results were analyzed at 4 weeks, 8 weeks, and 12 weeks relative to the baseline, which is shown in Tables 7-9 below. 95% CI=95% Confidence Interval of the observed difference between groups. ES=Effect size computation of change between groups.

TABLE 6

| Blood Lipids, Inflammation, and Glucose Homeostasis Variables | | | | | | | | |
|---|---|---|---|---|---|---|---|---|
| Variables | Group | Visit 2 (Week 0) | Visit 4 (Week 4) | Visit 5 (Week 8) | Visit 6 (Week 12) | Within-Group | | p |
| Total | 101 | 198.3 ± 34.3 | 199.8 ± 41.6 | 204.9 ± 37.8 | 201.9 ± 33.8 | 0.39 | Group | 0.88 |
| Cholesterol | 201 | 208.8 ± 33.4 | 193.8 ± 28.9§ | 194.6 ± 27.5§ | 185.7 ± 31.2 | 0.04 | Time | 0.16 |
| (mg/dL) | 301 | 198.8 ± 23.4 | 194.4 ± 25.0 | 194.9 ± 36.7 | 198.2 ± 28.6 | 0.79 | G × T | 0.04 |
| | | | | | | | ANCOVA | 0.03 |
| Triglycerides | 101 | 122.7 ± 64.1 | 113.2 ± 45.3 | 141.0 ± 89.0 | 128.8 ± 59.1 | 0.26 | Group | 0.60 |
| (mg/dL) | 201 | 115.8 ± 63.7 | 110.9 ± 63.6 | 107.6 ± 52.7 | 97.9 ± 44.7 | 0.34 | Time | 0.21 |
| | 301 | 145.3 ± 73.8 | 115.3 ± 54.8§ | 118.4 ± 56.6 | 138.4 ± 90.1 | 0.06 | G × T | 0.06 |
| | | | | | | | ANCOVA | 0.37 |
| HDL | 101 | 57.0 ± 25.2 | 57.6 ± 26.8 | 56.7 ± 24.4 | 58.2 ± 24.8 | 0.85 | Group | 0.98 |
| Cholesterol | 201 | 57.8 ± 17.0 | 58.6 ± 15.8 | 57.6 ± 15.4 | 58.4 ± 15.4 | 0.92 | Time | 0.83 |
| (mg/dL) | 301 | 59.2 ± 23.9 | 58.4 ± 23.1 | 59.2 ± 24.3 | 59.4 ± 22.8 | 0.91 | G × T | 0.98 |
| | | | | | | | ANCOVA | 0.94 |
| VLDL | 101 | 23.3 ± 11.8 | 21.2 ± 8.9 | 25.7 ± 18.0 | 22.8 ± 10.0 | 0.44 | Group | 0.60 |
| Cholesterol | 201 | 22.0 ± 11.9 | 21.2 ± 12.5 | 19.5 ± 9.3 | 17.9 ± 7.8 | 0.14 | Time | 0.08 |

TABLE 6-continued

Blood Lipids, Inflammation, and Glucose Homeostasis Variables

| Variables | Group | Visit 2 (Week 0) | Visit 4 (Week 4) | Visit 5 (Week 8) | Visit 6 (Week 12) | Within-Group | | p |
|---|---|---|---|---|---|---|---|---|
| (mg/dL) | 301 | 28.3 ± 13.6 | 22.2 ± 10.4§ | 21.7 ± 9.8§ | 24.7 ± 15.2 | 0.007 | G × T | 0.05 |
| | | | | | | | ANCOVA | 0.44 |
| LDL | 101 | 118.0 ± 26.2 | 121.0 ± 30.8 | 122.5 ± 30.6 | 120.9 ± 26.4 | 0.55 | Group | 0.78 |
| Cholesterol | 201 | 129.0 ± 33.5 | 114.0 ± 30.5§ | 117.5 ± 28.8§ | 109.4 ± 30.8 | 0.03 | Time | 0.33 |
| (mg/dL) | 301 | 111.3 ± 23.3 | 113.8 ± 27.0 | 114.0 ± 34.3 | 114.1 ± 30.8 | 0.84 | G × T | 0.02 |
| | | | | | | | ANCOVA | 0.03 |
| LDL:HDL | 101 | 2.44 ± 1.12 | 2.51 ± 1.25 | 2.53 ± 1.23 | 2.45 ± 1.22 | 0.76 | Group | 0.75 |
| Ratio | 201 | 2.49 ± 1.08 | 2.15 ± 0.97§ | 2.22 ± 0.88§ | 2.02 ± 0.73 | 0.03 | Time | 0.20 |
| | 301 | 2.17 ± 0.88 | 2.27 ± 1.03 | 2.23 ± 1.03 | 2.23 ± 1.06 | 0.67 | G × T | 0.02 |
| | | | | | | | ANCOVA | 0.03 |
| Insulin | 101 | 14.5 ± 15.8 | 14.9 ± 12.1 | 14.8 ± 12.2 | 17.0 ± 16.7 | 0.67 | Group | 0.15 |
| (μIU/mL) | 201 | 8.7 ± 5.1 | 7.9 ± 3.9 | 8.7 ± 4.3 | 8.8 ± 4.3 | 0.77 | Time | 0.37 |
| | 301 | 11.2 ± 6.9 | 11.1 ± 7.8 | 11.6 ± 10.1 | 13.8 ± 8.4 | 0.36 | G × T | 0.94 |
| | | | | | | | ANCOVA | 0.38 |
| Hb A1C | 101 | 5.25 ± 0.40 | — | 5.25 ± 0.46 | 5.25 ± 0.44 | 0.99 | Group | 0.20 |
| | 201 | 5.38 ± 0.35 | | 5.31 ± 0.43 | 5.33 ± 0.38 | 0.35 | Time | 0.70 |
| | 301 | 5.50 ± 0.25 | | 5.50 ± 0.27 | 5.47 ± 0.29 | 0.83 | G × T | 0.83 |
| | | | | | | | ANCOVA | 0.73 |
| HOMA-IR | 101 | 3.47 ± 4.13 | 3.79 ± 3.57 | 3.93 ± 3.78 | 4.49 ± 4.99 | 0.55 | Group | 0.16 |
| | 201 | 2.15 ± 1.38 | 1.96 ± 1.12 | 2.09 ± 1.04 | 2.15 ± 1.10 | 0.87 | Time | 0.35 |
| | 301 | 2.72 ± 1.80 | 2.83 ± 2.19 | 2.75 ± 2.45 | 3.40 ± 2.11 | 0.40 | G × T | 0.87 |
| | | | | | | | ANCOVA | 0.35 |
| C-Reactive | 101 | 3.75 ± 4.00 | 4.63 ± 4.53 | 3.75 ± 3.15 | 4.50 ± 4.87 | 0.65 | Group | 0.33 |
| Protein | 201 | 2.50 ± 1.41 | 3.75 ± 2.49 | 3.75 ± 2.66 | 3.38 ± 2.97 | 0.74 | Time | 0.27 |
| | 301 | 1.20 ± 0.42 | 2.20 ± 1.32 | 3.89 ± 5.81 | 2.20 ± 1.40 | 0.13 | G × T | 0.68 |
| | | | | | | | ANCOVA | 0.24 |

TABLE 7

4-Week Changes from Baseline (Blood Lipids, Inflammation, and Glucose Homeostasis Variables)

| Variables | Group | Week 4 Delta | p-value | | 95% CI | p-value | ES |
|---|---|---|---|---|---|---|---|
| Total | 101 | −0.5 ± 13.8‡ | 0.02 | 101 vs. 201 | (4.3, 24.6) | 0.006 | −1.18 |
| Cholesterol | 201 | −15.0 ± 10.0 | | 101 vs. 301 | (−4.4, 14.6) | 0.28 | −1.20 |
| (mg/dL) | 301 | −5.6 ± 14.9 | | 201 vs. 301 | (−19.2, 0.5) | 0.06 | −0.36 |
| Triglycerides | 101 | −9.2 ± 37.9 | 0.15 | 101 vs. 201 | (−32.7, 24.0) | 0.76 | 0.11 |
| (mg/dL) | 201 | −4.8 ± 43.3 | | 101 vs. 301 | (−5.9, 47.1) | 0.12 | −0.60 |
| | 301 | −29.8 ± 30.9 | | 201 vs. 301 | (−2.6, 52.6) | 0.08 | −0.66 |
| HDL | 101 | 1.0 ± 6.5 | 0.62 | 101 vs. 201 | (−3.8, 4.1) | 0.94 | −1.23 |
| Cholesterol | 201 | 0.8 ± 4.7 | | 101 vs. 301 | (−2.1, 5.4) | 0.38 | −0.11 |
| (mg/dL) | 301 | −0.6 ± 4.1 | | 201 vs. 301 | (−2.4, 5.3) | 0.44 | 1.62 |
| VLDL | 101 | −1.93 ± 5.98 | 0.08 | 101 vs. 201 | (−6.2, 4.1) | 0.67 | 0.15 |
| Cholesterol | 201 | −0.85 ± 8.13 | | 101 vs. 301 | (−0.6, 9.1) | 0.08 | −0.70 |
| (mg/dL) | 301 | −6.18 ± 6.22 | | 201 vs. 301 | (0.3, 10.3) | 0.04 | −0.74 |
| LDL | 101 | 0.4 ± 13.2‡ | 0.004 | 101 vs. 201 | (5.0, 25.8) | 0.005 | −1.23 |
| Cholesterol | 201 | −15.0 ± 11.8 | | 101 vs. 301 | (−10.5, 8.9) | 0.87 | −0.11 |
| (mg/dL) | 301 | 1.2 ± 15.0‡ | | 201 vs. 301 | (−26.3, 6.1) | 0.002 | 1.62 |
| LDL:HDL | 101 | 0.03 ± 0.4‡ | 0.002 | 101 vs. 201 | (0.12, 0.62) | 0.004 | −1.08 |
| Ratio | 201 | −0.35 ± 0.33 | | 101 vs. 301 | (−0.28, 0.18) | 0.67 | 0.15 |
| | 301 | 0.08 ± 0.29‡ | | 201 vs. 301 | (−0.67, −0.18) | 0.001 | 1.35 |
| Insulin | 101 | 0.43 ± 6.86 | 0.80 | 101 vs. 201 | (−2.5, 4.9) | 0.50 | −0.23 |
| (μIU/mL) | 201 | −0.81 ± 3.70 | | 101 vs. 301 | (−2.8, 4.1) | 0.71 | −0.12 |
| | 301 | −0.20 ± 3.16 | | 201 vs. 301 | (−4.2, 3.0) | 0.74 | 0.18 |
| HOMA-IR | 101 | 0.30 ± 1.42 | 0.54 | 101 vs. 201 | (−0.39, 1.35) | 0.27 | −0.39 |
| | 201 | −0.18 ± 0.98 | | 101 vs. 301 | (−0.56, 1.08) | 0.52 | −0.21 |
| | 301 | 0.04 ± 0.96 | | 201 vs. 301 | (1.07, 0.63) | 0.60 | 0.23 |
| C-Reactive | 101 | 1.17 ± 5.49 | 0.98 | 101 vs. 201 | (−4.3, 3.8) | 0.89 | 0.06 |
| Protein | 201 | 1.43 ± 3.15 | | 101 vs. 301 | (−3.8, 3.9) | 0.98 | −0.01 |
| | 301 | 1.11 ± 1.54 | | 201 vs. 301 | (−3.3, 4.0) | 0.86 | −0.13 |

TABLE 8

8-Week Changes from Baseline (Blood Lipids, Inflammation, and Glucose Homeostasis Variables)

| Variables | Group | Week 8 Delta | p-value | | 95% CI | p-value | ES |
|---|---|---|---|---|---|---|---|
| Total | 101 | 3.7 ± 16.4‡ | 0.08 | 101 vs. 201 | (2.2, 33.4) | 0.03 | −1.12 |
| Cholesterol | 201 | −14.2 ± 15.4 | | 101 vs. 301 | (−7.4, 22.6) | 0.31 | −0.34 |
| (mg/dL) | 301 | −3.9 ± 26.7 | | 201 vs. 301 | (−25.8, 5.4) | 0.19 | 0.47 |
| Triglycerides | 101 | 14.6 ± 47.0† | 0.04 | 101 vs. 201 | (−10.6, 56.1) | 0.18 | −0.51 |
| (mg/dL) | 201 | −8.2 ± 41.3 | | 101 vs. 301 | (9.3, 73.6) | 0.01 | −0.93 |
| | 301 | −26.9 ± 41.9 | | 201 vs. 301 | (−14.7, 52.1) | 0.26 | −0.45 |
| HDL | 101 | 0.13 ± 6.74 | 0.99 | 101 vs. 201 | (−4.5, 5.1) | 0.91 | −0.05 |
| Cholesterol | 201 | −0.15 ± 4.47 | | 101 vs. 301 | (−4.5, 4.8) | 0.95 | −0.02 |
| (mg/dL) | 301 | 0.00 ± 7.09 | | 201 vs. 301 | (−5.0, 4.7) | 0.95 | 0.03 |
| VLDL | 101 | 1.80 ± 9.27† | 0.02 | 101 vs. 201 | (−1.9, 10.4) | 0.17 | −0.52 |
| Cholesterol | 201 | −2.46 ± 6.81 | | 101 vs. 301 | (2.5, 14.3) | 0.006 | −1.00 |
| (mg/dL) | 301 | −6.60 ± 7.51 | | 201 vs. 301 | (−2.0, 10.3) | 0.18 | −0.58 |
| LDL | 101 | 1.7 ± 11.6 | 0.07 | 101 vs. 201 | (0.1, 26.5) | 0.05 | −1.07 |
| Cholesterol | 201 | −11.5 ± 13.1† | | 101 vs. 301 | (−13.7, 11.8) | 0.88 | 0.05 |
| (mg/dL) | 301 | 2.7 ± 23.8‡ | | 201 vs. 301 | (−27.4, −1.0) | 0.04 | 0.74 |
| LDL:HDL | 101 | 0.05 ± 0.3 | 0.02 | 101 vs. 201 | (0.07, 0.58) | 0.02 | −1.07 |
| Ratio | 201 | −0.27 ± 0.29† | | 101 vs. 301 | (−0.25, 0.24) | 0.96 | 0.02 |
| | 301 | 0.06 ± 0.39‡ | | 201 vs. 301 | (−0.58, −0.07) | 0.01 | 0.97 |
| Insulin | 101 | 0.12 ± 9.42 | 0.98 | 101 vs. 201 | (−5.2, 5.6) | 0.94 | −0.03 |
| (μIU/mL) | 201 | −0.10 ± 3.30 | | 101 vs. 301 | (−5.5, 4.9) | 0.91 | 0.04 |
| | 301 | 0.41 ± 6.71 | | 201 vs. 301 | (−5.9, 4.9) | 0.85 | 0.10 |
| Hb A1C | 101 | −0.03 ± 0.22 | 0.68 | 101 vs. 201 | (−0.12, 0.19) | 0.66 | −0.16 |
| | 201 | −0.07 ± 0.19 | | 101 vs. 301 | (−0.18, 0.11) | 0.64 | 0.17 |
| | 301 | 0.00 ± 0.17 | | 201 vs. 301 | (−0.22, 0.09) | 0.39 | 0.37 |
| HOMA-IR | 101 | 0.39 ± 2.08 | 0.76 | 101 vs. 201 | (−0.87, 1.75) | 0.50 | −0.27 |
| | 201 | −0.05 ± 0.93 | | 101 vs. 301 | (−0.90, 1.62) | 0.57 | −0.18 |
| | 301 | 0.02 ± 1.80 | | 201 vs. 301 | (−1.39, 1.23) | 0.90 | 0.05 |
| C-Reactive | 101 | 0.00 ± 1.31 | 0.37 | 101 vs. 201 | (−1.9, 1.3) | 0.67 | 0.28 |
| Protein | 201 | 0.33 ± 1.69 | | 101 vs. 301 | (−2.5, 0.5) | 0.17 | 0.66 |
| | 301 | 1.00 ± 1.69 | | 201 vs. 301 | (−2.3, 0.9) | 0.39 | 0.48 |

TABLE 9

12-Week Changes from Baseline (Blood Lipids, Inflammation, and Glucose Homeostasis Variables)

| Variables | Group | Week 12 Delta | p-value | | 95% CI | p-value | ES |
|---|---|---|---|---|---|---|---|
| Total | 101 | 3.6 ± 13.8‡ | 0.02 | 101 vs. 201 | (7.5, 45.9) | 0.008 | −1.11 |
| Cholesterol | 201 | −23.1 ± 31.2 | | 101 vs. 301 | (−13.2, 23.3) | 0.58 | −0.26 |
| (mg/dL) | 301 | −1.4 ± 24.3‡ | | 201 vs. 301 | (−39.9, −3.4) | 0.02 | 0.77 |
| Triglycerides | 101 | 6.2 ± 35.1 | 0.45 | 101 vs. 201 | (−14.4, 62.4) | 0.21 | −0.63 |
| (mg/dL) | 201 | −17.8 ± 41.1 | | 101 vs. 301 | (−22.1, 51.0) | 0.43 | −0.29 |
| | 301 | −8.3 ± 61.3 | | 201 vs. 301 | (−46.1, 27.0) | 0.60 | 0.18 |
| HDL | 101 | 1.23 ± 5.29 | 0.92 | 101 vs. 201 | (−4.2, 5.4) | 0.80 | −0.10 |
| Cholesterol | 201 | 0.62 ± 6.86 | | 101 vs. 301 | (−3.6, 5.5) | 0.69 | −0.16 |
| (mg/dL) | 301 | 0.31 ± 5.85 | | 201 vs. 301 | (−4.2, 4.9) | 0.89 | −0.05 |
| VLDL | 101 | −0.54 ± 7.43 | 0.48 | 101 vs. 201 | (−3.2, 10.2) | 0.29 | −0.48 |
| Cholesterol | 201 | −4.08 ± 7.20 | | 101 vs. 301 | (−3.0, 9.8) | 0.29 | −0.81 |
| (mg/dL) | 301 | −3.94 ± 9.96 | | 201 vs. 301 | (−6.5, 6.2) | 0.97 | −0.34 |
| LDL | 101 | 2.9 ± 12.9‡ | 0.01 | 101 vs. 201 | (5.7, 39.4) | 0.01 | −1.08 |
| Cholesterol | 201 | −19.6 ± 26.6 | | 101 vs. 301 | (−15.3, 16.8) | 0.93 | −0.04 |
| (mg/dL) | 301 | 2.2 ± 21.8‡ | | 201 vs. 301 | (−37.8, −5.8) | 0.009 | 0.90 |
| LDL:HDL | 101 | 0.02 ± 0.49‡ | 0.02 | 101 vs. 201 | (0.08, 0.89) | 0.02 | −0.84 |
| Ratio | 201 | −0.47 ± 0.65 | | 101 vs. 301 | (−0.42, 0.35) | 0.86 | 0.08 |
| | 301 | 0.05 ± 0.39‡ | | 201 vs. 301 | (−0.91, −0.13) | 0.01 | 0.97 |
| Insulin | 101 | 2.50 ± 18.63 | 0.80 | 101 vs. 201 | (−6.4, 11.2) | 0.58 | −0.18 |
| (μIU/mL) | 201 | 0.09 ± 3.09 | | 101 vs. 301 | (−8.5, 8.3) | 0.98 | 0.01 |
| | 301 | 2.61 ± 5.77 | | 201 vs. 301 | (−10.9, 5.8) | 0.55 | 0.54 |
| Hb A1C | 101 | 0.01 ± 0.15 | 0.82 | 101 vs. 201 | (−0.11, 0.15) | 0.72 | −0.14 |
| | 201 | −0.47 ± 0.65 | | 101 vs. 301 | (−0.09, 0.16) | 0.53 | −0.24 |
| | 301 | 0.05 ± 0.39 | | 201 vs. 301 | (−0.11, 0.14) | 0.80 | −0.09 |
| HOMA-IR | 101 | 1.02 ± 5.32 | 0.70 | 101 vs. 201 | (−1.44, 3.48) | 0.41 | −0.27 |
| | 201 | 0.00 ± 0.79 | | 101 vs. 301 | (−1.99, 2.69) | 0.76 | −0.09 |
| | 301 | 0.67 ± 1.36 | | 201 vs. 301 | (−3.01, 1.67) | 0.57 | 0.60 |
| C-Reactive | 101 | 0.75 ± 1.28 | 0.32 | 101 vs. 201 | (−0.85, 2.68) | 0.29 | −0.54 |
| Protein | 201 | −0.17 ± 2.04 | | 101 vs. 301 | (−1.95, 1.23) | 0.64 | 0.26 |
| | 301 | 1.11 ± 1.45 | | 201 vs. 301 | (−3.00, 0.45) | 0.14 | 0.72 |

It was surprisingly discovered that the exemplary cyto-protective composition I provided a significant decrease in total cholesterol, VLDL cholesterol, LDL cholesterol, and LDL:HDL to the subjects after 4 weeks, 8 weeks, and 12 weeks.

Visual Analog Scales (VAS) variables were assessed for each subject using a line scale with the ends of the line scale representing the most extreme sensations ever felt for the variable. A listing of the variables along with the corresponding sensations are provided in Table 10 below.

TABLE 10

VAS Sensation Key

| Variable | Sensation at Left End of Line Scale Represented by a Lower Numerical Value | Sensation at Right End of Line Scale Represented by a Higher Numerical Value |
|---|---|---|
| I feel vigorous and energetic: | Strongly Disagree | Strongly Agree |
| My mood today is: | Worst Possible | Best Possible |
| My current level of fatigue is low (I'm not tired): | Strongly Disagree | Strongly Agree |
| I have a clear mind today: | Strongly Disagree | Strongly Agree |
| My ability to handle difficult projects is high today: | Strongly Disagree | Strongly Agree |
| My ability to concentrate today is: | Worst Possible | Best Possible |
| My willingness to perform | Lowest Possible | Highest Possible |

TABLE 10-continued

VAS Sensation Key

| Variable | Sensation at Left End of Line Scale Represented by a Lower Numerical Value | Sensation at Right End of Line Scale Represented by a Higher Numerical Value |
|---|---|---|
| physical exercise is: | | |
| My willingness to perform mental tasks is: | Lowest Possible | Highest Possible |
| My current state of enthusiasm is: | Lowest Possible | Highest Possible |
| My current state of well-being is: | Worst Possible | Best Possible |
| My ability to handle stress is: | Worse than usual | Better than usual |
| My overall productivity is high: | Strongly Disagree | Strongly Agree |
| My current quality of sleep is: | More restless than usual | More restful than usual |
| My current overall digestive & gut health is: | Worse than usual | Better than usual |
| My current quality of bowel movements is: | Less than usual | More than usual |
| My level of abdominal bloating is: | Less than usual | More than usual |

A summary of the results for the VAS Variables is shown in Table 11 below. These results were analyzed at 4 weeks, 8 weeks, and 12 weeks relative to the baseline, which is shown in Tables 12-14 below. 95% CI=95% Confidence Interval of the observed difference between groups. ES=Effect size computation of change between groups.

TABLE 11

Visual Analog Scales Variables

| Variables | Group | Visit 2 (Week 0) | Visit 4 (Week 4) | Visit 5 (Week 8) | Visit 6 (Week 12) | Within-Group | | p |
|---|---|---|---|---|---|---|---|---|
| Energetic | 101 | 52.1 ± 19.9 | 66.5 ± 18.9 | 65.5 ± 20.3 | 72.2 ± 16.3§ | 0.005 | Group | 0.06 |
| | 201 | 58.8 ± 23.6 | 69.5 ± 23.4 | 70.3 ± 23.9 | 69.1 ± 21.6 | 0.27 | Time | <0.001 |
| | 301 | 67.5 ± 20.5 | 78.5 ± 15.0 | 79.1 ± 19.0 | 84.4 ± 17.4 | 0.02 | G × T | 0.93 |
| | | | | | | | ANCOVA | 0.21 |
| Mood | 101 | 73.5 ± 16.2 | 78.7 ± 11.6 | 81.4 ± 11.2 | 79.1 ± 12.3 | 0.28 | Group | 0.57 |
| | 201 | 77.4 ± 19.4 | 82.0 ± 13.3 | 78.3 ± 19.2 | 75.7 ± 19.4 | 0.47 | Time | 0.27 |
| | 301 | 81.2 ± 17.4 | 85.1 ± 18.6 | 81.9 ± 17.9 | 83.7 ± 18.0 | 0.69 | G × T | 0.71 |
| | | | | | | | ANCOVA | 0.47 |
| Fatigue | 101 | 51.2 ± 25.8 | 71.0 ± 19.4 | 61.4 ± 25.6 | 61.4 ± 29.2 | 0.13 | Group | 0.19 |
| | 201 | 73.4 ± 25.1 | 68.8 ± 31.1 | 65.8 ± 27.0 | 76.9 ± 21.0 | 0.53 | Time | 0.45 |
| | 301 | 71.6 ± 28.7 | 77.9 ± 24.2 | 73.7 ± 30.8 | 72.2 ± 34.1 | 0.82 | G × T | 0.46 |
| | | | | | | | ANCOVA | 0.83 |
| Clear Mind | 101 | 77.0 ± 23.2 | 81.6 ± 13.4 | 82.9 ± 12.4 | 80.5 ± 14.2 | 0.63 | Group | 0.69 |
| | 201 | 82.9 ± 18.2 | 84.6 ± 12.7 | 79.1 ± 25.1 | 83.8 ± 19.1 | 0.68 | Time | 0.58 |
| | 301 | 82.5 ± 19.8 | 85.4 ± 16.5 | 85.8 ± 16.3 | 87.2 ± 18.9 | 0.56 | G × T | 0.79 |
| | | | | | | | ANCOVA | 0.78 |
| Difficult Projects | 101 | 70.7 ± 19.2 | 78.3 ± 16.7 | 74.9 ± 22.6 | 82.1 ± 13.3 | 0.20 | Group | 0.47 |
| | 201 | 78.1 ± 26.3 | 85.7 ± 12.4 | 80.3 ± 22.6 | 79.8 ± 19.9 | 0.42 | Time | 0.12 |
| | 301 | 80.3 ± 19.9 | 83.8 ± 16.8 | 83.6 ± 16.8 | 86.0 ± 17.3 | 0.55 | G × T | 0.76 |
| | | | | | | | ANCOVA | 0.62 |
| Concentration | 101 | 70.5 ± 18.3 | 77.6 ± 14.5 | 80.8 ± 14.5 | 81.3 ± 10.6§ | 0.04 | Group | 0.50 |
| | 201 | 72.3 ± 25.6 | 82.5 ± 11.8 | 79.5 ± 25.0 | 78.1 ± 20.7 | 0.42 | Time | 0.02 |
| | 301 | 80.1 ± 20.0 | 87.1 ± 16.0 | 87.1 ± 13.5 | 83.9 ± 18.9 | 0.31 | G × T | 0.84 |
| | | | | | | | ANCOVA | 0.78 |
| Perform Exercise | 101 | 71.1 ± 18.9 | 78.0 ± 15.7 | 76.7 ± 12.5 | 78.1 ± 15.2 | 0.29 | Group | 0.55 |
| | 201 | 75.1 ± 16.2 | 81.0 ± 16.3 | 68.9 ± 27.3 | 71.5 ± 24.2 | 0.13 | Time | 0.03 |
| | 301 | 72.4 ± 25.0 | 85.4 ± 17.3 | 82.9 ± 20.5 | 82.1 ± 23.6 | 0.12 | G × T | 0.27 |
| | | | | | | | ANCOVA | 0.30 |
| Mental Tasks | 101 | 72.9 ± 18.4 | 77.2 ± 16.9 | 81.8 ± 12.3 | 80.6 ± 11.6 | 0.18 | Group | 0.37 |
| | 201 | 81.4 ± 15.2 | 83.0 ± 13.2 | 75.7 ± 27.3 | 77.4 ± 22.8 | 0.31 | Time | 0.20 |
| | 301 | 78.9 ± 22.4 | 87.7 ± 12.2 | 87.2 ± 18.4 | 87.9 ± 13.2 | 0.13 | G × T | 0.13 |
| | | | | | | | ANCOVA | 0.10 |
| Enthusiasm | 101 | 68.3 ± 17.4 | 79.0 ± 13.7 | 79.7 ± 12.8 | 80.1 ± 13.5§ | 0.006 | Group | 0.49 |
| | 201 | 73.0 ± 25.1 | 77.7 ± 21.8 | 75.2 ± 28.0 | 75.9 ± 25.7 | 0.66 | Time | 0.007 |
| | 301 | 77.4 ± 19.2 | 84.4 ± 14.0 | 83.4 ± 17.3 | 85.3 ± 13.4 | 0.30 | G × T | 0.70 |
| | | | | | | | ANCOVA | 0.25 |
| Well Being | 101 | 74.7 ± 19.9 | 81.3 ± 11.8 | 79.7 ± 14.9 | 82.3 ± 10.5 | 0.23 | Group | 0.64 |
| | 201 | 80.8 ± 19.1 | 83.7 ± 15.4 | 77.8 ± 22.7 | 76.5 ± 24.1 | 0.10 | Time | 0.19 |
| | 301 | 81.1 ± 15.3 | 84.0 ± 13.8 | 83.6 ± 17.4 | 88.3 ± 15.3 | 0.30 | G × T | 0.20 |
| | | | | | | | ANCOVA | 0.06 |

TABLE 11-continued

Visual Analog Scales Variables

| Variables | Group | Visit 2 (Week 0) | Visit 4 (Week 4) | Visit 5 (Week 8) | Visit 6 (Week 12) | Within-Group | | p |
|---|---|---|---|---|---|---|---|---|
| Ability to | 101 | 70.7 ± 20.8 | 79.3 ± 13.7 | 77.3 ± 10.7 | 76.4 ± 9.8 | 0.41 | Group | 0.90 |
| Handle Stress | 201 | 76.1 ± 22.5 | 75.5 ± 20.1 | 77.0 ± 24.4 | 75.5 ± 22.9 | 0.99 | Time | 0.22 |
| | 301 | 70.9 ± 19.3 | 78.6 ± 20.6 | 79.7 ± 16.7 | 82.9 ± 19.1 | 0.21 | G × T | 0.70 |
| | | | | | | | ANCOVA | 0.33 |
| Productivity | 101 | 73.0 ± 15.6 | 80.3 ± 14.0 | 71.1 ± 21.4 | 79.4 ± 10.7 | 0.17 | Group | 0.42 |
| | 201 | 75.2 ± 21.8 | 84.1 ± 17.6 | 74.5 ± 24.9 | 79.5 ± 23.1 | 0.17 | Time | 0.008 |
| | 301 | 77.7 ± 16.7 | 84.6 ± 15.0 | 82.8 ± 16.7 | 87.5 ± 15.4 | 0.15 | G × T | 0.79 |
| | | | | | | | ANCOVA | 0.45 |
| Sleep Quality | 101 | 45.9 ± 25.8 | 62.3 ± 19.9 | 58.7 ± 15.7 | 59.3 ± 20.6 | 0.06 | Group | 0.17 |
| | 201 | 53.0 ± 26.9 | 61.3 ± 21.3 | 68.2 ± 19.6 | 61.1 ± 20.8 | 0.16 | Time | 0.006 |
| | 301 | 61.1 ± 16.8 | 66.3 ± 12.1 | 67.8 ± 19.3 | 72.9 ± 18.8 | 0.19 | G × T | 0.64 |
| | | | | | | | ANCOVA | 0.51 |
| Gut Health | 101 | 58.8 ± 19.3 | 71.8 ± 21.1 | 70.1 ± 19.1 | 70.9 ± 17.0 | 0.18 | Group | 0.99 |
| | 201 | 63.8 ± 25.6 | 73.6 ± 15.0 | 69.7 ± 22.7 | 66.5 ± 16.5 | 0.32 | Time | 0.20 |
| | 301 | 67.9 ± 22.4 | 68.1 ± 20.6 | 66.1 ± 32.9 | 73.3 ± 20.2 | 0.78 | G × T | 0.61 |
| | | | | | | | ANCOVA | 0.55 |
| Bowel Quality | 101 | 61.4 ± 17.1 | 65.1 ± 19.3 | 64.7 ± 21.3 | 64.5 ± 15.4 | 0.94 | Group | 0.82 |
| | 201 | 57.8 ± 17.2 | 66.5 ± 17.2 | 59.0 ± 12.5 | 59.2 ± 14.2 | 0.30 | Time | 0.34 |
| | 301 | 59.0 ± 17.9 | 63.8 ± 23.1 | 59.0 ± 30.1 | 67.0 ± 22.5 | 0.49 | G × T | 0.86 |
| | | | | | | | ANCOVA | 0.42 |
| Abdominal | 101 | 52.8 ± 26.7 | 34.7 ± 18.2S | 42.8 ± 21.0 | 39.2 ± 21.1 | 0.03 | Group | 0.30 |
| Bloating | 201 | 55.8 ± 23.0 | 45.2 ± 20.9 | 51.6 ± 22.3 | 53.2 ± 21.2* | 0.44 | Time | <0.001 |
| | 301 | 55.4 ± 16.4 | 40.4 ± 22.4§ | 52.1 ± 32.2 | 28.9 ± 18.2§ | 0.005 | G × T | 0.15 |
| | | | | | | | ANCOVA | 0.008 |

TABLE 12

4-Week Changes from Baseline (Visual Analog Scales)

| Variables | Group | Week 4 Delta | p-value | | 95% CI | p-value | ES |
|---|---|---|---|---|---|---|---|
| Energy | 101 | 14.4 ± 22.0 | 0.84 | 101 vs. 201 | (−13.7, 21.3) | 1.00 | −0.15 |
| | 201 | 10.6 ± 27.4 | | 101 vs. 301 | (−12.0, 21.2) | 0.66 | −0.22 |
| | 301 | 9.8 ± 19.4 | | 201 vs. 301 | (−16.4, 18.0) | 0.93 | −0.03 |
| Mood | 101 | 5.1 ± 16.2 | 0.95 | 101 vs. 201 | (−11.9, 12.9) | 0.93 | −0.03 |
| | 201 | 4.6 ± 13.0 | | 101 vs. 301 | (−9.9, 13.7) | 0.75 | −0.11 |
| | 301 | 3.3 ± 18.5 | | 201 vs. 301 | (−10.9, 13.6) | 0.82 | −0.09 |
| Fatigue | 101 | 19.8 ± 30.2 | 0.15 | 101 vs. 201 | (−1.05, 49.9) | 0.06 | −0.75 |
| | 201 | −4.6 ± 34.8 | | 101 vs. 301 | (−8.6, 39.7) | 0.20 | −0.48 |
| | 301 | 4.3 ± 34.8 | | 201 vs. 301 | (−34.0, 16.2) | 0.48 | 0.26 |
| Clear Mind | 101 | 4.6 ± 24.4 | 0.88 | 101 vs. 201 | (−10.8, 16.7) | 0.67 | −0.15 |
| | 201 | 1.7 ± 13.0 | | 101 vs. 301 | (−10.2, 15.9) | 0.66 | −0.14 |
| | 301 | 1.8 ± 13.7 | | 201 vs. 301 | (−13.6, 13.5) | 0.99 | 0.00 |
| Difficult | 101 | 7.6 ± 17.8 | 0.74 | 101 vs. 201 | (−14.5, 14.5) | 0.99 | 0.00 |
| Projects | 201 | 7.6 ± 20.1 | | 101 vs. 301 | (−9.1, 18.3) | 0.50 | −0.25 |
| | 301 | 3.0 ± 19.1 | | 201 vs. 301 | (−9.7, 18.9) | 0.52 | −0.24 |
| Concentrate | 101 | 7.1 ± 18.5 | 0.83 | 101 vs. 201 | (−18.7, 12.6) | 0.69 | 0.14 |
| | 201 | 10.2 ± 25.1 | | 101 vs. 301 | (−13.3, 16.4) | 0.83 | −0.09 |
| | 301 | 5.6 ± 17.9 | | 201 vs. 301 | (−10.8, 20.1) | 0.54 | −0.21 |
| Perform | 101 | 6.9 ± 19.0 | 0.55 | 101 vs. 201 | (−13.0, 14.9) | 0.58 | −0.06 |
| Exercise | 201 | 5.9 ± 11.0 | | 101 vs. 301 | (−19.0, 7.4) | 0.89 | 0.29 |
| | 301 | 12.7 ± 21.6 | | 201 vs. 301 | (−20.5, 6.9) | 0.33 | 0.39 |
| Mental Tasks | 101 | 4.3 ± 21.1 | 0.63 | 101 vs. 201 | (−10.5, 15.9) | 0.68 | −0.16 |
| | 201 | 1.6 ± 10.7 | | 101 vs. 301 | (−15.8, 9.1) | 0.59 | 0.17 |
| | 301 | 7.7 ± 17.4 | | 201 vs. 301 | (−19.1, 6.9) | 0.35 | 0.42 |
| Enthusiasm | 101 | 10.7 ± 16.8 | 0.57 | 101 vs. 201 | (−6.2, 18.2) | 0.33 | −0.40 |
| | 201 | 4.7 ± 12.9 | | 101 vs. 301 | (−6.8, 16.3) | 0.41 | −0.28 |
| | 301 | 5.9 ± 17.1 | | 201 vs. 301 | (−13.3, 10.8) | 0.84 | 0.08 |
| Well Being | 101 | 6.6 ± 20.7 | 0.74 | 101 vs. 201 | (−7.8, 15.1) | 0.52 | −0.23 |
| | 201 | 2.9 ± 8.0 | | 101 vs. 301 | (−7.2, 14.5) | 0.50 | −0.21 |
| | 301 | 2.9 ± 12.6 | | 201 vs. 301 | (−11.3, 11.3) | 0.99 | 0.00 |
| Handle Stress | 101 | 8.6 ± 23.4 | 0.61 | 101 vs. 201 | (−10.0, 28.3) | 0.34 | −0.39 |
| | 201 | −0.5 ± 23.4 | | 101 vs. 301 | (−16.0, 20.4) | 0.81 | −0.09 |
| | 301 | 6.4 ± 27.7 | | 201 vs. 301 | (−25.8, 12.0) | 0.46 | 0.27 |
| Productivity | 101 | 7.3 ± 18.6 | 0.93 | 101 vs. 201 | (−16.0, 12.7) | 0.82 | 0.09 |
| | 201 | 8.9 ± 19.8 | | 101 vs. 301 | (−12.6, 14.6) | 0.88 | −0.06 |
| | 301 | 6.3 ± 18.0 | | 201 vs. 301 | (−11.5, 16.8) | 0.70 | −0.14 |
| Sleep Quality | 101 | 16.3 ± 26.8 | 0.34 | 101 vs. 201 | (−11.1, 27.2) | 0.40 | −0.29 |
| | 201 | 8.3 ± 27.6 | | 101 vs. 301 | (−4.8, 31.5) | 0.14 | −0.56 |
| | 301 | 2.9 ± 20.8 | | 201 vs. 301 | (−13.5, 24.2) | 0.57 | −0.22 |

TABLE 12-continued

| | | 4-Week Changes from Baseline (Visual Analog Scales) | | | | | |
|---|---|---|---|---|---|---|---|
| Variables | Group | Week 4 Delta | p-value | | 95% CI | p-value | ES |
| Gut Health | 101 | 13.0 ± 32.6 | 0.47 | 101 vs. 201 | (−19.0, 25.5) | 0.77 | −0.11 |
| | 201 | 9.8 ± 24.3 | | 101 vs. 301 | (−8.6, 33.5) | 0.24 | −0.40 |
| | 301 | 0.6 ± 29.0 | | 201 vs. 301 | (−12.7, 31.1) | 0.40 | −0.34 |
| Bowel Quality | 101 | 3.7 ± 26.9 | 0.86 | 101 vs. 201 | (−23.8, 13.7) | 0.59 | 0.20 |
| | 201 | 8.8 ± 22.4 | | 101 vs. 301 | (−19.5, 16.0) | 0.84 | 0.07 |
| | 301 | 5.5 ± 23.6 | | 201 vs. 301 | (−15.2, 21.7) | 0.72 | −0.14 |
| Abdominal | 101 | −18.1 ± 22.3 | 0.65 | 101 vs. 201 | (−26.8, 11.8) | 0.44 | 0.30 |
| Bloating | 201 | −10.6 ± 27.6 | | 101 vs. 301 | (−25.8, 10.8) | 0.41 | 0.31 |
| | 301 | −10.6 ± 25.8 | | 201 vs. 301 | (−19.0, 19.0) | 0.99 | 0.00 |

TABLE 13

| | | 8-Week Changes from Baseline (Visual Analog Scales) | | | | | |
|---|---|---|---|---|---|---|---|
| Variables | Group | Week 8 Delta | p-value | | 95% CI | p-value | ES |
| Energy | 101 | 13.5 ± 17.6 | 0.96 | 101 vs. 201 | (−15.2, 19.2) | 0.81 | −0.11 |
| | 201 | 11.5 ± 20.5 | | 101 vs. 301 | (−14.9, 18.7) | 0.82 | −0.08 |
| | 301 | 11.6 ± 28.0 | | 201 vs. 301 | (−17.6, 17.3) | 0.99 | 0.00 |
| Mood | 101 | 7.9 ± 20.4 | 0.53 | 101 vs. 201 | (−7.8, 21.7) | 0.35 | −0.36 |
| | 201 | 0.9 ± 18.6 | | 101 vs. 301 | (−7.3, 21.6) | 0.32 | −0.37 |
| | 301 | 0.7 ± 18.6 | | 201 vs. 301 | (−14.8, 15.2) | 0.98 | −0.01 |
| Fatigue | 101 | 10.2 ± 33.7 | 0.44 | 101 vs. 201 | (−10.2, 45.8) | 0.21 | −0.54 |
| | 201 | −7.6 ± 32.9 | | 101 vs. 301 | (−19.3, 35.6) | 0.55 | −0.21 |
| | 301 | 2.1 ± 42.2 | | 201 vs. 301 | (−38.1, 18.8) | 0.50 | 0.26 |
| Clear Mind | 101 | 5.9 ± 21.4 | 0.41 | 101 vs. 201 | (−5.2, 24.6) | 0.20 | −0.45 |
| | 201 | −3.8 ± 22.0 | | 101 vs. 301 | (−12.0, 17.2) | 0.72 | −0.14 |
| | 301 | 3.3 ± 13.9 | | 201 vs. 301 | (−22.3, 8.0) | 0.35 | 0.39 |
| Difficult | 101 | 4.1 ± 21.3 | 0.98 | 101 vs. 201 | (−15.6, 19.4) | 0.83 | −0.08 |
| Projects | 201 | 2.2 ± 25.7 | | 101 vs. 301 | (−16.4, 17.9) | 0.93 | −0.04 |
| | 301 | 3.4 ± 21.5 | | 201 vs. 301 | (−18.9, 16.6) | 0.90 | 0.05 |
| Concentrate | 101 | 10.3 ± 19.4 | 0.91 | 101 vs. 201 | (−14.2, 20.6) | 0.71 | −0.13 |
| | 201 | 7.2 ± 29.7 | | 101 vs. 301 | (−13.8, 20.4) | 0.70 | −0.18 |
| | 301 | 7.0 ± 18.2 | | 201 vs. 301 | (−17.6, 17.9) | 0.99 | −0.01 |
| Perform | 101 | 5.6 ± 18.0 | 0.13 | 101 vs. 201 | (−4.7, 28.2) | 0.16 | −0.61 |
| Exercise | 201 | −6.2 ± 20.5 | | 101 vs. 301 | (−21.1, 11.3) | 0.54 | 0.22 |
| | 301 | 10.5 ± 25.5‡ | | 201 vs. 301 | (−33.4, 0.1) | 0.05 | 0.72 |
| Mental Tasks | 101 | 8.9 ± 19.1‡ | 0.09 | 101 vs. 201 | (0.02, 29.2) | 0.05 | −0.78 |
| | 201 | −5.7 ± 18.6 | | 101 vs. 301 | (−13.7, 15.0) | 0.93 | −0.03 |
| | 301 | 8.3 ± 19.4 | | 201 vs. 301 | (−28.8, 0.9) | 0.06 | 0.74 |
| Enthusiasm | 101 | 11.4 ± 16.7 | 0.47 | 101 vs. 201 | (−5.9, 24.2) | 0.22 | −0.59 |
| | 201 | 2.2 ± 14.3 | | 101 vs. 301 | (−9.4, 20.1) | 0.47 | −0.25 |
| | 301 | 6.1 ± 25.8 | | 201 vs. 301 | (−19.1, 11.4) | 0.61 | 0.18 |
| Well Being | 101 | 4.9 ± 15.8 | 0.44 | 101 vs. 201 | (−4.6, 20.3) | 0.21 | −0.58 |
| | 201 | −2.9 ± 11.0 | | 101 vs. 301 | (−9.8, 14.6) | 0.70 | −0.13 |
| | 301 | 2.6 ± 20.3 | | 201 vs. 301 | (−18.1, 7.2) | 0.39 | 0.34 |
| Handle Stress | 101 | 6.7 ± 27.2 | 0.66 | 101 vs. 201 | (−11.9, 23.4) | 0.52 | −0.25 |
| | 201 | 0.9 ± 18.5 | | 101 vs. 301 | (−19.5, 15.2) | 0.81 | 0.09 |
| | 301 | 8.8 ± 22.0 | | 201 vs. 301 | (−25.8, 10.1) | 0.38 | 0.39 |
| Productivity | 101 | −1.9 ± 19.9 | 0.65 | 101 vs. 201 | (−17.3, 14.8) | 0.88 | 0.06 |
| | 201 | −0.6 ± 19.2 | | 101 vs. 301 | (−22.7, 8.8) | 0.38 | 0.32 |
| | 301 | 5.1 ± 23.3 | | 201 vs. 301 | (−22.0, 10.6) | 0.49 | 0.27 |
| Sleep Quality | 101 | 12.7 ± 28.9 | 0.70 | 101 vs. 201 | (−23.1, 18.3) | 0.81 | 0.09 |
| | 201 | 15.2 ± 20.6 | | 101 vs. 301 | (−14.3, 26.3) | 0.55 | −0.22 |
| | 301 | 6.7 ± 25.7 | | 201 vs. 301 | (−12.6, 29.5) | 0.42 | −0.33 |
| Gut Health | 101 | 11.3 ± 28.9 | 0.51 | 101 vs. 201 | (−17.4, 28.3) | 0.63 | −0.20 |
| | 201 | 5.8 ± 24.3 | | 101 vs. 301 | (−9.4, 35.4) | 0.25 | −0.40 |
| | 301 | −1.7 ± 35.0 | | 201 vs. 301 | (−15.7, 30.8) | 0.51 | −0.25 |
| Bowel Quality | 101 | 3.3 ± 29.5 | 0.94 | 101 vs. 201 | (−18.1, 22.1) | 0.84 | −0.08 |
| | 201 | 1.2 ± 18.4 | | 101 vs. 301 | (−16.5, 23.0) | 0.74 | −0.11 |
| | 301 | 0.0 ± 28.5 | | 201 vs. 301 | (−19.2, 21.7) | 0.90 | −0.05 |
| Abdominal | 101 | −10.0 ± 4.2 | 0.76 | 101 vs. 201 | (−25.6, 14.3) | 0.57 | 0.22 |
| Bloating | 201 | −3.3 ± 26.7 | | 101 vs. 301 | (−26.4, 13.0) | 0.50 | 0.24 |
| | 301 | −6.0 ± 25.7 | | 201 vs. 301 | (−21.4, 19.5) | 0.93 | 0.04 |

TABLE 14

| | | 12-Week Changes from Baseline (Visual Analog Scales) | | | | | | |
|---|---|---|---|---|---|---|---|---|
| Variables | Group | Week 12 Delta | p-value | | | 95% CI | p-value | ES |
| Energy | 101 | 20.1 ± 24.1 | 0.52 | 101 vs. 201 | (−7.6, 27.4) | 0.26 | −0.46 |
| | 201 | 10.2 ± 19.1 | | 101 vs. 301 | (−13.0, 20.7) | 0.65 | −0.16 |
| | 301 | 16.3 ± 24.3 | | 201 vs. 301 | (−23.5, 11.4) | 0.49 | 0.28 |
| Mood | 101 | 5.6 ± 17.7 | 0.49 | 101 vs. 201 | (−5.0, 19.5) | 0.24 | −0.46 |
| | 201 | −1.7 ± 14.1 | | 101 vs. 301 | (−8.5, 15.1) | 0.57 | −0.20 |
| | 301 | 2.3 ± 15.7 | | 201 vs. 301 | (−16.2, 8.3) | 0.52 | 0.27 |
| Fatigue | 101 | 10.2 ± 32.4 | 0.64 | 101 vs. 201 | (−16.6, 29.9) | 0.57 | −0.24 |
| | 201 | 3.5 ± 21.2 | | 101 vs. 301 | (−12.1, 32.8) | 0.36 | −0.31 |
| | 301 | −0.1 ± 34.7 | | 201 vs. 301 | (−19.6, 26.9) | 0.75 | −0.13 |
| Clear Mind | 101 | 3.5 ± 19.2 | 0.91 | 101 vs. 201 | (−11.4, 16.5) | 0.72 | −0.14 |
| | 201 | 0.9 ± 17.2 | | 101 vs. 301 | (−13.6, 13.3) | 0.98 | 0.01 |
| | 301 | 3.6 ± 18.2 | | 201 vs. 301 | (−16.7, 11.3) | 0.70 | 0.15 |
| Difficult | 101 | 11.4 ± 18.1 | 0.45 | 101 vs. 201 | (−6.2, 25.5) | 0.23 | −0.50 |
| Projects | 201 | 1.8 ± 20.3 | | 101 vs. 301 | (−8.7, 21.8) | 0.39 | −0.31 |
| | 301 | 4.9 ± 23.2 | | 201 vs. 301 | (−18.9, 12.7) | 0.70 | 0.14 |
| Concentrate | 101 | 10.8 ± 13.2 | 0.57 | 101 vs. 201 | (−10.0, 20.0) | 0.50 | −0.27 |
| | 201 | 5.8 ± 23.0 | | 101 vs. 301 | (−6.9, 22.0) | 0.30 | −0.42 |
| | 301 | 3.3 ± 21.6 | | 201 vs. 301 | (−12.5, 17.5) | 0.74 | −0.11 |
| Perform | 101 | 6.9 ± 19.4 | 0.26 | 101 vs. 201 | (−5.8, 26.9) | 0.20 | −0.51 |
| Exercise | 201 | −3.6 ± 22.2 | | 101 vs. 301 | (−18.1, 13.4) | 0.77 | 0.11 |
| | 301 | 9.3 ± 22.3 | | 201 vs. 301 | (−29.2, 3.4) | 0.12 | 0.58 |
| Mental Tasks | 101 | 7.7 ± 11.1 | 0.10 | 101 vs. 201 | (−0.9, 24.3) | 0.07 | −0.83 |
| | 201 | −4.0 ± 16.7 | | 101 vs. 301 | (−13.1, 11.2) | 0.88 | 0.06 |
| | 301 | 8.7 ± 20.3‡ | | 201 vs. 301 | (−25.3, −0.06) | 0.05 | 0.68 |
| Enthusiasm | 101 | 11.7 ± 10.9 | 0.27 | 101 vs. 201 | (−2.0, 19.6) | 0.11 | −0.81 |
| | 201 | 2.9 ± 11.0 | | 101 vs. 301 | (−6.6, 14.2) | 0.47 | −0.25 |
| | 301 | 7.9 ± 18.7 | | 201 vs. 301 | (−15.8, 5.8) | 0.36 | 0.33 |
| Well Being | 101 | 7.6 ± 16.9‡ | 0.06 | 101 vs. 201 | (0.7, 23.0) | 0.04 | −0.75 |
| | 201 | −4.2 ± 10.2 | | 101 vs. 301 | (−10.5, 10.9) | 0.97 | −0.01 |
| | 301 | 7.4 ± 15.1‡ | | 201 vs. 301 | (−22.8, −0.5) | 0.04 | 0.90 |
| Handle Stress | 101 | 5.7 ± 19.5 | 0.32 | 101 vs. 201 | (−9.5, 22.1) | 0.43 | −0.36 |
| | 201 | −0.5 ± 14.9 | | 101 vs. 301 | (−20.9, 9.6) | 0.46 | 0.25 |
| | 301 | 11.4 ± 25.3 | | 201 vs. 301 | (−27.7, 3.9) | 0.14 | 0.57 |
| Productivity | 101 | 6.4 ± 11.4 | 0.70 | 101 vs. 201 | (−9.8, 14.0) | 0.72 | −0.14 |
| | 201 | 4.3 ± 17.2 | | 101 vs. 301 | (−14.3, 8.6) | 0.62 | 0.19 |
| | 301 | 9.3 ± 17.8 | | 201 vs. 301 | (−16.9, 6.9) | 0.41 | 0.29 |
| Sleep Quality | 101 | 13.4 ± 28.9 | 0.83 | 101 vs. 201 | (−12.5, 23.2) | 0.55 | −0.22 |
| | 201 | 8.1 ± 17.3 | | 101 vs. 301 | (−13.9, 20.5) | 0.70 | −0.13 |
| | 301 | 10.1 ± 21.4 | | 201 vs. 301 | (−19.9, 15.8) | 0.82 | 0.11 |
| Gut Health | 101 | 12.1 ± 26.5 | 0.63 | 101 vs. 201 | (−10.5, 29.4) | 0.35 | −0.39 |
| | 201 | 2.6 ± 21.2 | | 101 vs. 301 | (−13.7, 24.8) | 0.56 | −0.20 |
| | 301 | 6.5 ± 29.3 | | 201 vs. 301 | (−23.9, 16.1) | 0.69 | 0.15 |
| Bowel Quality | 101 | 3.1 ± 25.3 | 0.71 | 101 vs. 201 | (−17.3, 20.6) | 0.86 | −0.07 |
| | 201 | 1.5 ± 20.7 | | 101 vs. 301 | (−23.9, 12.6) | 0.53 | 0.22 |
| | 301 | 8.8 ± 27.4 | | 201 vs. 301 | (−26.3, 11.6) | 0.44 | 0.30 |
| Abdominal | 101 | −13.6 ± 28.8 | 0.08 | 101 vs. 201 | (−31.1, 9.1) | 0.28 | 0.40 |
| Bloating | 201 | −2.6 ± 26.5 | | 101 vs. 301 | (−7.6, 31.2) | 0.23 | −0.45 |
| | 301 | −25.4 ± 23.2‡ | | 201 vs. 301 | (−2.7, 42.9) | 0.03 | −0.92 |

It was surprisingly discovered that subjects of the exemplary cytoprotective composition II felt their level of abdominal bloating decreased after 12 weeks.

Complete Blood Count variables were assessed for each subject at 0 weeks, 4 weeks, 8 weeks, and 12 weeks. A summary of the results is shown in Table 15 below.

TABLE 15

| | | Complete Blood Count Variables | | | | | | |
|---|---|---|---|---|---|---|---|---|
| Variables | Group | Visit 2 (Week 0) | Visit 4 (Week 4) | Visit 5 (Week 8) | Visit 6 (Week 12) | Time | Group | Group × Time |
| White Blood | 101 | 5.6 ± 1.0 | 5.6 ± 1.7 | 5.3 ± 1.2 | 5.2 ± 1.1 | 0.47 | 0.64 | 0.25 |
| Cell Count | 201 | 5.7 ± 1.0 | 5.8 ± 1.5 | 6.0 ± 1.7 | 6.1 ± 2.3 | | | |
| (cells × $10^3$/μL) | 301 | 5.4 ± 0.8 | 5.8 ± 1.2 | 5.5 ± 0.9 | 6.0 ± 1.5 | | | |
| Red Blood | 101 | 4.61 ± 0.55 | 4.58 ± 0.50 | 4.60 ± 0.52 | 4.64 ± 0.47 | 0.03 | 0.86 | 0.77 |
| Cell Count | 201 | 4.49 ± 0.37 | 4.46 ± 0.37 | 4.53 ± 0.32 | 4.58 ± 0.39 | | | |
| (cells × $10^3$/μL) | 301 | 4.55 ± 0.40 | 4.57 ± 0.39 | 4.60 ± 0.38 | 4.61 ± 0.39 | | | |
| Hemoglobin | 101 | 14.1 ± 1.9 | 14.0 ± 1.7 | 14.1 ± 1.8 | 14.1 ± 1.5 | 0.48 | 0.92 | 0.67 |
| (g/dL) | 201 | 14.0 ± 1.4 | 13.8 ± 1.4 | 14.0 ± 1.3 | 14.1 ± 1.4 | | | |
| | 301 | 13.8 ± 1.4 | 13.8 ± 1.3 | 13.9 ± 1.4 | 13.8 ± 1.3 | | | |
| Hematocrit | 101 | 41.6 ± 4.7 | 41.1 ± 4.3 | 41.2 ± 4.4 | 42.2 ± 4.0 | <0.001 | 0.96 | 0.89 |
| (%) | 201 | 41.1 ± 3.7 | 40.3 ± 3.7 | 41.2 ± 3.9 | 41.9 ± 3.0 | | | |
| | 301 | 41.0 ± 3.8 | 40.8 ± 3.6 | 41.0 ± 3.3 | 41.7 ± 3.8 | | | |

TABLE 15-continued

| | | | | | | | | Group × |
|---|---|---|---|---|---|---|---|---|
| Variables | Group | Visit 2 (Week 0) | Visit 4 (Week 4) | Visit 5 (Week 8) | Visit 6 (Week 12) | Time | Group | Time |
| Mean | 101 | 90.3 ± 5.0 | 89.8 ± 4.4 | 89.8 ± 4.7 | 91.2 ± 4.3 | <0.001 | 0.72 | 0.71 |
| Corpuscle | 201 | 91.5 ± 4.7 | 90.4 ± 4.9 | 91.0 ± 5.8 | 91.8 ± 5.2 | | | |
| Volume | 301 | 90.1 ± 3.0 | 89.4 ± 2.4 | 89.2 ± 2.9 | 90.6 ± 2.5 | | | |
| Mean | 101 | 30.5 ± 2.0 | 30.6 ± 1.6 | 30.6 ± 1.5 | 30.4 ± 1.3 | 0.15 | 0.51 | 0.65 |
| Corpuscle | 201 | 31.1 ± 2.0 | 30.9 ± 2.0 | 30.8 ± 2.0 | 30.9 ± 2.5 | | | |
| Hemoglobin | 301 | 30.2 ± 1.2 | 30.2 ± 1.1 | 30.2 ± 1.4 | 29.9 ± 1.2 | | | |
| Mean | 101 | 33.8 ± 1.2 | 34.2 ± 0.8 | 34.1 ± 1.0 | 33.4 ± 0.8 | <0.001 | 0.63 | 0.50 |
| Corpuscle | 201 | 33.9 ± 1.0 | 34.2 ± 0.8 | 33.9 ± 0.7 | 33.6 ± 1.2 | | | |
| Hemoglobin Content | 301 | 33.6 ± 0.7 | 33.8 ± 0.8 | 33.9 ± 1.1 | 33.1 ± 0.9 | | | |
| Red Cell | 101 | 13.4 ± 1.4 | 13.4 ± 2.0 | 13.4 ± 1.4 | 13.5 ± 0.8 | 0.05 | 0.54 | 0.49 |
| Dimension | 201 | 13.1 ± 0.8 | 13.0 ± 0.7 | 13.3 ± 0.5 | 13.3 ± 0.9 | | | |
| Width | 301 | 13.4 ± 0.5 | 13.4 ± 0.7 | 13.7 ± 0.9 | 13.9 ± 0.8 | | | |
| Platelets | 101 | 253 ± 79 | 240 ± 55 | 240 ± 62 | 244 ± 60 | 0.42 | 0.22 | 0.15 |
| | 201 | 279 ± 53 | 283 ± 63 | 292 ± 57 | 285 ± 64 | | | |
| | 301 | 256 ± 51 | 256 ± 41 | 264 ± 57 | 264 ± 48 | | | |
| Neutrophils | 101 | 3.14 ± 0.61 | 3.23 ± 1.42 | 2.85 ± 0.76 | 2.83 ± 0.73 | 0.32 | 0.74 | 0.23 |
| | 201 | 2.97 ± 0.83 | 3.04 ± 1.08 | 3.17 ± 1.21 | 3.34 ± 1.86 | | | |
| | 301 | 3.03 ± 0.83 | 3.41 ± 0.98 | 3.11 ± 0.83 | 3.62 ± 1.33 | | | |
| Lymphocytes | 101 | 1.80 ± 0.44 | 1.71 ± 0.33 | 1.76 ± 0.39 | 1.75 ± 0.49 | 0.94 | 0.24 | 0.42 |
| | 201 | 2.03 ± 0.44 | 2.02 ± 0.59 | 2.08 ± 0.59 | 1.94 ± 0.62 | | | |
| | 301 | 1.66 ± 0.48 | 1.74 ± 0.47 | 1.69 ± 0.50 | 1.78 ± 0.54 | | | |
| Monocytes | 101 | 0.48 ± 0.13 | 0.51 ± 0.13 | 0.48 ± 0.15 | 0.48 ± 0.12 | 0.44 | 0.92 | 0.98 |
| | 201 | 0.46 ± 0.13 | 0.47 ± 0.16 | 0.47 ± 0.11 | 0.47 ± 0.18 | | | |
| | 301 | 0.46 ± 0.13 | 0.50 ± 0.12 | 0.46 ± 0.10 | 0.47 ± 0.14 | | | |
| Eosinophils | 101 | 0.15 ± 0.09 | 0.13 ± 0.09 | 0.15 ± 0.09 | 0.14 ± 0.09 | 0.54 | 0.25 | 0.31 |
| | 201 | 0.22 ± 0.18 | 0.20 ± 0.18 | 0.24 ± 0.18 | 0.22 ± 0.16 | | | |
| | 301 | 0.16 ± 0.07 | 0.16 ± 0.08 | 0.14 ± 0.05 | 0.17 ± 0.06 | | | |
| Basophils | 101 | 0.008 ± 0.03 | 0.000 ± 0.00 | 0.017 ± 0.04 | 0.000 ± 0.00 | 0.10 | 0.03 | 0.70 |
| | 201 | 0.036 ± 0.05 | 0.036 ± 0.05 | 0.06 ± 0.05 | 0.036 ± 0.05 | | | |
| | 301 | 0.021 ± 0.04 | 0.014 ± 0.04 | 0.01 ± 0.04 | 0.007 ± 0.03 | | | |
| Immature | 101 | 0.00 ± 0.00 | 0.00 ± 0.00 | 0.017 ± 0.04 | 0.00 ± 0.00 | 0.08 | 0.27 | 0.34 |
| Granulocytes | 201 | 0.00 ± 0.00 | 0.009 ± 0.03 | 0.009 ± 0.03 | 0.00 ± 0.00 | | | |
| | 301 | 0.00 ± 0.00 | 0.00 ± 0.00 | 0.00 ± 0.00 | 0.00 ± 0.00 | | | |
| Neutrophils | 101 | 56.3 ± 5.5 | 56.0 ± 7.6 | 53.7 ± 5.1 | 54.0 ± 6.3 | 0.34 | 0.25 | 0.52 |
| (%) | 201 | 51.6 ± 7.6 | 52.3 ± 8.1 | 51.6 ± 7.6 | 53.9 ± 9.3 | | | |
| | 301 | 56.3 ± 9.9 | 57.9 ± 8.3 | 56.4 ± 9.2 | 58.7 ± 10.3 | | | |
| Lymphocytes | 101 | 31.9 ± 5.2 | 31.8 ± 6.7 | 33.8 ± 4.8 | 33.6 ± 5.9 | 0.35 | 0.42 | 0.44 |
| (%) | 201 | 35.5 ± 5.9 | 35.1 ± 6.7 | 35.2 ± 6.5 | 33.4 ± 8.2 | | | |
| | 301 | 3.20 ± 10.7 | 30.0 ± 7.9 | 31.6 ± 9.5 | 30.0 ± 10.6 | | | |
| Monocytes | 101 | 8.75 ± 1.76 | 9.00 ± 1.76 | 9.08 ± 1.98 | 9.33 ± 2.23 | 0.74 | 0.43 | 0.44 |
| (%) | 201 | 8.09 ± 2.02 | 8.18 ± 1.99 | 8.09 ± 1.81 | 8.18 ± 3.60 | | | |
| | 301 | 8.43 ± 1.87 | 8.79 ± 1.85 | 8.57 ± 1.50 | 7.71 ± 1.64 | | | |
| Eosinophils | 101 | 2.42 ± 1.38 | 2.50 ± 1.51 | 2.83 ± 1.27 | 2.50 ± 1.31 | 0.45 | 0.19 | 0.30 |
| (%) | 201 | 4.00 ± 2.90 | 3.55 ± 2.58 | 4.18 ± 2.82 | 3.73 ± 3.00 | | | |
| | 301 | 2.86 ± 1.35 | 2.79 ± 1.37 | 2.64 ± 0.93 | 3.07 ± 1.07 | | | |
| Basophils | 101 | 0.58 ± 0.51 | 0.50 ± 0.52 | 0.50 ± 0.52 | 0.50 ± 0.52 | 0.99 | 0.15 | 0.92 |
| (%) | 201 | 0.82 ± 0.40 | 0.82 ± 0.60 | 0.73 ± 0.47 | 0.82 ± 0.75 | | | |
| | 301 | 0.43 ± 0.51 | 0.43 ± 0.51 | 0.57 ± 0.51 | 0.50 ± 0.52 | | | |
| Immature | 101 | 0.083 ± 0.29 | 0.25 ± 0.45 | 0.17 ± 0.39 | 0.08 ± 0.29 | 0.01 | 0.44 | 0.53 |
| Granulocytes | 201 | 0.00 ± 0.00 | 0.09 ± 0.03 | 0.18 ± 0.40 | 0.00 ± 0.00 | | | |
| (%) | 301 | 0.00 ± 0.00 | 0.00 ± 0.00 | 0.21 ± 0.43 | 0.00 ± 0.00 | | | |

No significant interactions were evident related to clinical safety.

Comprehensive Metabolic Panel variables were assessed for each subject at 0 weeks, 4 weeks, 8 weeks, and 12 weeks. A summary of the results is shown in Table 16 below.

TABLE 16

Comprehensive Metabolic Panel Variables

| | | | | | | | | Group × |
|---|---|---|---|---|---|---|---|---|
| Variables | Group | Visit 2 (Week 0) | Visit 4 (Week 4) | Visit 5 (Week 8) | Visit 6 (Week 12) | Time | Group | Time |
| Glucose | 101 | 91.9 ± 8.5 | 95.0 ± 12.8 | 98.2 ± 15.6 | 97.2 ± 13.2 | 0.11 | 0.92 | 0.08 |
| (mg/dL) | 201 | 96.3 ± 11.8 | 96.9 ± 13.6 | 98.6 ± 14.5 | 96.7 ± 14.2 | | | |
| | 301 | 96.5 ± 7.8 | 99.1 ± 11.6 | 95.3 ± 12.0 | 98.2 ± 12.1 | | | |
| Blood Urea | 101 | 12.8 ± 2.0 | 13.6 ± 3.5 | 13.0 ± 3.4 | 13.5 ± 2.6 | 0.85 | 0.44 | 0.30 |
| Nitrogen | 201 | 13.3 ± 2.2 | 13.8 ± 3.1 | 13.4 ± 2.3 | 14.2 ± 2.7 | | | |
| (mg/dL) | 301 | 15.1 ± 4.5 | 13.7 ± 3.2 | 15.0 ± 3.9 | 14.5 ± 3.9 | | | |

TABLE 16-continued

Comprehensive Metabolic Panel Variables

| Variables | Group | Visit 2 (Week 0) | Visit 4 (Week 4) | Visit 5 (Week 8) | Visit 6 (Week 12) | Time | Group | Group × Time |
|---|---|---|---|---|---|---|---|---|
| Creatinine | 101 | 0.81 ± 0.19 | 0.84 ± 0.21 | 0.83 ± 0.18 | 0.84 ± 0.19 | <0.001 | 0.43 | 0.12 |
| (mg/dL) | 201 | 0.86 ± 0.21 | 0.94 ± 0.19 | 0.96 ± 0.24 | 0.95 ± 0.22 | | | |
| | 301 | 0.84 ± 0.18 | 0.91 ± 0.16 | 0.89 ± 0.15 | 0.88 ± 0.17 | | | |
| BUN:Creatinine | 101 | 16.6 ± 5.2 | 17.0 ± 4.9 | 15.8 ± 3.7 | 16.6 ± 4.8 | 0.04 | 0.47 | 0.12 |
| Ratio | 201 | 16.2 ± 4.1 | 14.8 ± 2.4 | 14.3 ± 2.2 | 15.2 ± 3.1 | | | |
| | 301 | 18.3 ± 5.4 | 15.2 ± 3.7 | 17.2 ± 5.8 | 16.9 ± 5.4 | | | |
| Sodium | 101 | 138.8 ± 2.9 | 139.9 ± 1.7 | 139.1 ± 1.3 | 138.9 ± 1.7 | 0.07 | 0.80 | 0.36 |
| (mEq/mL) | 201 | 139.4 ± 3.4 | 139.5 ± 2.4 | 140.2 ± 2.0 | 139.1 ± 2.6 | | | |
| | 301 | 138.9 ± 1.9 | 139.7 ± 1.5 | 139.9 ± 1.3 | 139.9 ± 1.8 | | | |
| Potassium | 101 | 4.25 ± 0.23 | 4.25 ± 0.17 | 4.29 ± 0.25 | 4.28 ± 0.24 | 0.94 | 0.28 | 0.72 |
| (mEq/mL) | 201 | 4.27 ± 0.18 | 4.29 ± 0.23 | 4.23 ± 0.23 | 4.26 ± 0.28 | | | |
| | 301 | 4.41 ± 0.27 | 4.35 ± 0.22 | 4.37 ± 0.25 | 4.33 ± 0.23 | | | |
| Chloride | 101 | 102.4 ± 2.9 | 102.5 ± 2.5 | 102.8 ± 2.3 | 102.6 ± 2.4 | 0.41 | 0.83 | 0.57 |
| (mEq/mL) | 201 | 103.6 ± 2.9 | 102.5 ± 3.0 | 103.2 ± 2.6 | 102.7 ± 3.2 | | | |
| | 301 | 102.9 ± 1.6 | 102.5 ± 2.1 | 102.9 ± 1.9 | 103.4 ± 1.6 | | | |
| Carbon | 101 | 23.8 ± 2.0 | 24.1 ± 1.6 | 23.6 ± 2.1 | 23.4 ± 2.0 | 0.07 | 0.88 | 0.80 |
| Dioxide | 201 | 24.4 ± 1.9 | 24.4 ± 1.6 | 23.5 ± 2.4 | 23.5 ± 1.5 | | | |
| | 301 | 24.9 ± 2.4 | 24.4 ± 1.6 | 24.1 ± 2.1 | 23.5 ± 1.6 | | | |
| Calcium | 101 | 9.35 ± 0.28 | 9.36 ± 0.25 | 9.42 ± 0.26 | 9.36 ± 0.36 | 0.78 | 0.77 | 0.69 |
| (mg/dL) | 201 | 9.42 ± 0.31 | 9.42 ± 0.33 | 9.42 ± 0.42 | 9.52 ± 0.32 | | | |
| | 301 | 9.33 ± 0.45 | 9.43 ± 0.44 | 9.31 ± 0.47 | 9.37 ± 0.37 | | | |
| Total Protein | 101 | 6.92 ± 0.44 | 6.97 ± 0.39 | 6.89 ± 0.36 | 6.89 ± 0.43 | 0.80 | 0.35 | 0.44 |
| (g/dL) | 201 | 6.75 ± 0.40 | 6.69 ± 0.37 | 6.69 ± 0.41 | 6.86 ± 0.40 | | | |
| | 301 | 6.86 ± 0.33 | 6.89 ± 0.37 | 6.94 ± 0.39 | 6.90 ± 0.27 | | | |
| Albumin | 101 | 4.37 ± 0.29 | 4.38 ± 0.26 | 4.35 ± 0.24 | 4.35 ± 0.28 | 0.80 | 0.89 | 0.37 |
| (g/dL) | 201 | 4.42 ± 0.18 | 4.41 ± 0.23 | 4.32 ± 0.31 | 4.44 ± 0.25 | | | |
| | 301 | 4.36 ± 0.22 | 4.41 ± 0.25 | 4.43 ± 0.32 | 4.38 ± 0.23 | | | |
| Globulin | 101 | 2.55 ± 0.32 | 2.59 ± 0.38 | 2.55 ± 0.31 | 2.54 ± 0.31 | 0.78 | 0.14 | 0.73 |
| (g/dL) | 201 | 2.33 ± 0.32 | 2.29 ± 0.28 | 2.37 ± 0.25 | 2.42 ± 0.27 | | | |
| | 301 | 2.50 ± 0.32 | 2.48 ± 0.34 | 2.51 ± 0.26 | 2.52 ± 0.36 | | | |
| Albumin:Globulin | 101 | 1.73 ± 0.25 | 1.73 ± 0.36 | 1.73 ± 0.27 | 1.74 ± 0.23 | 0.52 | 0.17 | 0.73 |
| Ratio | 201 | 1.93 ± 0.26 | 1.96 ± 0.24 | 1.83 ± 0.24 | 1.87 ± 0.25 | | | |
| | 301 | 1.77 ± 0.24 | 1.81 ± 0.29 | 1.79 ± 0.23 | 1.79 ± 0.28 | | | |
| Bilirubin | 101 | 0.67 ± 0.25 | 0.61 ± 0.21 | 0.65 ± 0.22 | 0.58 ± 0.17 | 0.09 | 0.38 | 0.54 |
| (g/dL) | 201 | 0.59 ± 0.26 | 0.62 ± 0.24 | 0.64 ± 0.32 | 0.55 ± 0.19 | | | |
| | 301 | 0.47 ± 0.24 | 0.54 ± 0.26 | 0.51 ± 0.32 | 0.49 ± 0.27 | | | |
| Alkaline | 101 | 75.5 ± 20.7 | 75.8 ± 20.9 | 78.1 ± 22.5 | 78.7 ± 22.5 | 0.003 | 0.61 | 0.65 |
| Phosphatase | 201 | 70.2 ± 16.5 | 67.8 ± 16.1 | 68.6 ± 17.2 | 72.6 ± 21.8 | | | |
| (U/L) | 301 | 73.0 ± 15.5 | 73.3 ± 16.7 | 75.0 ± 19.3 | 77.0 ± 18.2 | | | |
| AST | 101 | 26.4 ± 18.6 | 24.2 ± 13.9 | 27.9 ± 20.6 | 26.4 ± 16.8 | 0.20 | 0.74 | 0.31 |
| (U/L) | 201 | 24.2 ± 9.0 | 22.8 ± 6.6 | 24.0 ± 9.5 | 20.6 ± 6.7 | | | |
| | 301 | 26.9 ± 10.7 | 23.4 ± 5.1 | 22.6 ± 5.6 | 23.8 ± 11.4 | | | |
| ALT | 101 | 30.8 ± 24.2 | 27.2 ± 20.1 | 32.8 ± 30.0 | 31.0 ± 24.2 | 0.02 | 0.45 | 0.29 |
| (U/L) | 201 | 27.2 ± 11.0 | 23.0 ± 9.9 | 25.4 ± 13.8 | 22.8 ± 8.7 | | | |
| | 301 | 25.5 ± 14.3 | 21.8 ± 12.1 | 21.1 ± 12.3 | 22.3 ± 14.5 | | | |

No significant interactions were evident related to clinical safety with the exception of serum creatinine levels (interaction p=0.02). Post hoc analyses indicated this value increased with NAD3 supplementation only. However, in spite of this increase with NAD3 supplementation, values were below the typical reference range (adult men: 0.74-1.35 mg/dL, adult women: 0.59-1.04 mg/dL).

In Vivo Analysis II

In another in vivo study, the inventors assessed the impact of the exemplary cytoprotective compositions on biomarkers of aging from plasma and PBMCs of several subjects. In particular, the diets of the subjects were supplemented with the control composition (referenced in FIGS. 13-28 as "CTL group"), the exemplary cytoprotective composition I (referenced in FIGS. 13-28 as "NAD3 group") and the exemplary cytoprotective composition II (referenced in FIGS. 13-28 as "NAD3+TB group"). To assess this impact, the inventors (1) isolated PBMC mRNA from each of the subjects and performed transcriptomics; (2) isolated PBMC DNA, performed a telomere length assay, and obtained Horvath data via sequencing; (3) isolated PBMC lysates, performed NAD+ assays using mass spectrometry metabolomics, and performed SIRT activity assays; and (4) performed plasma assays for IL-6, GDF-15, BDNF, Osteopontin, and Activin A.

FIGS. 13A-13D depict control and exemplary results for the assessment of telomere length for the subjects using published qPCR methods of Lin et al. (Psychoneuroendocrinology. 2019 January; 99: 271-278.). As can be seen, there was no change in telomere length in the CTL group. Dependent samples t-tests also indicated no within-group changes in the NAD3 and NAD3+TB group. However, at week 4, telomere length values were greater in the NAD3 group versus control (#, p<0.05). Additionally, at week 4, telomere length values trended greater in the NAD3+TB group versus control (#, p<0.055). These stats were performed using within-samples t-tests (for within group comparisons) as well as independent samples t-tests between groups at each time point.

FIGS. 14A-14D depict control and exemplary results for the assessment of SIRT activity for the subjects using published methods of Aging (Albany NY) 2020 May 5; 12(10):9447-9460. As can be seen, when removing outliers, there was a decrease in the CTL group by weeks 12

(*,p<0.05). No increases were observed in the other groups, though there were clearly responders in the NAD3+TB group. However, at week 12, SIRT activity values trended greater in NAD3 group versus the CTL group (#, p=0.0572). Additionally, at week 12, SIRT activity values trended greater in the NAD3+TB group versus the CTL group (#, p=0.100). These stats were performed using within-samples t-tests (for within group comparisons) as well as independent samples t-tests between groups at each time point.

FIGS. 15-19 depict control and exemplary results for the assessment of PBMC NAD+ and NADH levels for the subjects using published methods of Lamb et al. (Aging (Albany NY). 2020 May 31; 12(10): 9447-9460. In particular, an assessment of plasma IL-6 levels using an ELISA kit is shown in FIG. 15, an assessment of plasma GDF-15 levels using an ELISA kit is shown in FIG. 16, an assessment of plasma BDNF levels using an ELISA kit is shown in FIG. 17, an assessment of plasma Osteopontin levels using an ELISA kit is shown in FIG. 18, and an assessment of plasma Activin A levels using an ELISA kit is shown in FIG. 19. Unfortunately, plasma values were highly variable in some assessments and, in the other assessments, there were no changes within supplementation groups over time.

FIGS. 20-29 depict control and exemplary results for the assessment of mRNA expression patterns in PBMCs isolated from the subjects that were quantified using microarray chips (Clariom™ S Assay, human) and analyzed using Transcriptome Analysis Console (TAC) 4.0.1. In particular, an assessment of mRNA marker TERF1 is shown in FIG. 20, an assessment of mRNA marker POT1 is shown in FIG. 22, an assessment of mRNA marker SIRT6 is shown in FIG. 22, an assessment of mRNA marker NMRK1 is shown in FIG. 23, an assessment of mRNA marker NMNAT1 is shown in FIG. 24, an assessment of mRNA marker PGC-1α is shown in FIG. 25, an assessment of mRNA marker NLRP2 is shown in FIG. 26, an assessment of mRNA marker SOX2 is shown in FIG. 27, an assessment of mRNA marker SOD3 is shown in FIG. 28, and an assessment of mRNA marker KLF5 is shown in FIG. 29.

FIGS. 30-35 depict control and exemplary results for the assessment of six targets of the NAD metabolome, including NAD+, NADP+, NADH, NADPH, NAAD and NMN. The assessment was performed as follows.

Standard substances of 6 targeted compounds (NAD, NADP, NADH, NADPH, NAAD and NMN) were used to prepare a stock standard solution freshly in a 13C10-GTP internal standard-Tris buffer solution. This solution was serially diluted to prepare calibration solutions. The concentration range was 0.0025 to 40 nM for each compound.

After thawing the samples on ice, the volume of the liquid in each sample was topped to 100 μL with Tris buffer. 400 μL of deoxygenated ethanol was then added to each tube. The samples were vortexed for 1 minute and sonicated for 30 seconds, followed by centrifugal clarification for 10 min at 5° C. The pellets were used for protein assays in order to normalize values. 150 μL of the clear supernatant of each sample was dried at room temperature under a nitrogen gas flow in the dark. The residue was reconstituted in 100 μL of the internal standard solution. 20-μL aliquots of the resultant sample solutions and the calibration solutions were injected to run LC-MRM/MS on a Waters Acquity UPLC coupled to a Sciex QTRAP 6500 Plus mass spectrometer with (−) ion detection. A reversed-phase C18 column (2.1*100 mm, 1.8 μm) was used for LC separation, with a tributylamine buffer (solvent A) and methanol (solvent B) as the mobile phase for binary solvent gradient elution of 5% to 90% B over 25 min at 50° C. and 0.25 mL/min. Calibration curves of individual metabolites were constructed with internal calibration.

Concentrations of individual metabolites detected in each sample were calculated by interpolating the calibration curves with the peak area ratios measured from injections of sample solutions. Note, NMN values were too low to detect. The assay was performed on baseline, day 7, week 4, and week 12 samples (10-12 participants per group).

The assessment of NAD+ is shown in FIG. 30 and found that NAD+ concentrations were significantly greater in the NAD3 group versus CTL group at week 12. The assessment of NADP+ is shown in FIG. 31 and found that NADP+ levels increased from baseline to day 7 in the CTL group. Additionally, levels trended downward from baseline to day 7 in the NAD3 group. The assessment of NADH is shown in FIG. 32 and found that NADH concentrations significantly decreased in the CTL group at week 12. The assessment of NADPH is shown in FIG. 33 and found that NAPDH trended downward from baseline to day 7 in the CTL group. The assessment of NAAD is shown in FIG. 34 and found that NAAD concentrations significantly decreased in the CTL group at week 12, but not in other groups. An analysis of the ratio of NAD+/NADH is shown in FIG. 35 and found that NAD+/NADH values were significantly greater in the NAD3 group versus CTL group at week 12. This appeared to be due to the trending down of values in the CTL group (p=0.081) as well as the trending of values upwards in the NAD3 group (p=0.127).

In summary, as introduced above, the inventors sought to examine if 12 weeks of daily supplementation of the exemplary cytoprotective compositions I ("NAD3") or II ("NAD3-TB") altered select NAD+-associated metabolites in PBMCs as well as serum lipids in human subjects. Significant interactions (p<0.05) were observed for total and LDL cholesterol, where values significantly decreased with NAD3 supplementation. Additionally, a significant interaction was observed for PBMC NAD+/NADH values, where values trended downward from Pre to Post in the CTL group (p=0.081) and values at Post were greater in NAD3 versus CTL (p=0.023). In particular, the current study demonstrates that over a 12-week supplementation period daily supplementation with the exemplary cytoprotective composition I reduced serum total and LDL cholesterol concentrations.

Further, without being bound by theory, the inventors contemplate that maintaining PBMC NAD+/NADH levels using the exemplary cytoprotective composition I is beneficial for a variety of reasons. First, there is enthusiasm surrounding the role that tissue NAD+ concentrations play in the aging process, and some research suggests that the age-associated loss in tissue NAD+ level contributes to aging and cellular senescence (reviewed in PMID: 29514713). The de novo formation of NAD+ from the amino acid tryptophan occurs via the kynurenine pathway, albeit NAD+ biosynthesis can also occur via the salvage/recycling pathway. Nicotinamide phosphoribosyltransferase (NAMPT) is the rate-limiting enzyme in the latter of these two pathways. Nicotinamide riboside (NR) supplementation has gained recent notoriety for being capable of increasing blood and tissue NAD+ levels, and this is due to NR being a precursor substrate in the NAD+ salvage pathway. Indeed, the exemplary cytoprotective composition I contains microgram amounts of niacin, and niacin is a substrate used for NAD+ biosynthesis. Hence, our observations of the exemplary cytoprotective composition I supplementation being able to maintain PBMC NAD+/NADH levels could be related to the supplement stimulating NAD+ biosynthesis through increasing cellular NAD+ precursor concentrations.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of increasing telomere length in a cell of a mammal via SIRT1 and SIRT6 upregulation, comprising:
    administering an effective amount of a cytoprotective composition to the mammal so as to upregulate SIRT1 and SIRT6 to thereby increase telomere stability and length in the cell of the mammal;
    wherein the cytoprotective composition includes a cytoprotective formulation comprising a combination of (a) a purine alkaloid, (b) an isothiocyanate or thioglucoside, (c) a metal-containing antioxidant; and
    wherein the cytoprotective formulation is formulated for oral administration with a nutritionally or pharmaceutically acceptable carrier.

2. A method of increasing global SIRT 1-7 activity in a mammal, comprising:
    administering an effective amount of a cytoprotective composition to the mammal so as to increase global SIRT 1-7 activity in the mammal;
    wherein the cytoprotective composition includes a cytoprotective formulation comprising a combination of (a) a purine alkaloid, (b) an isothiocyanate or thioglucoside, (c) a metal-containing antioxidant; and
    wherein the cytoprotective formulation is formulated for oral administration with a nutritionally or pharmaceutically acceptable carrier.

3. A method of increasing at least one of the level of NAD+ or the ratio of NAD+/NADH via upregulation of PGC-1α, in a mammal, comprising:
    administering an effective amount of a cytoprotective composition to the mammal so as to upregulate PGC-1α to thereby increase at least one of the level of NAD+ or the ratio of NAD+/NADH, in the mammal;
    wherein the cytoprotective composition includes a cytoprotective formulation comprising a combination of (a) a purine alkaloid, (b) an isothiocyanate or thioglucoside, (c) a metal-containing antioxidant; and
    wherein the cytoprotective formulation is formulated for oral administration with a nutritionally or pharmaceutically acceptable carrier.

4. The method of claim 3, wherein the step of administering the effective amount of the cytoprotective composition is performed so as to increase the level of NAD+ in the mammal.

5. The method of claim 3, wherein the step of administering the effective amount of the cytoprotective composition is performed so as to increase the ratio of NAD+/NADH in the mammal.

6. The method of claim 3, wherein the cytoprotective composition further comprises one or more additional ingredients including selenium, a polyphenol, olive leaf extract, tributyrin, and/or BHB.

* * * * *